(12) United States Patent
Campbell et al.

(10) Patent No.: US 12,011,506 B2
(45) Date of Patent: Jun. 18, 2024

(54) COMBINATION AND USES AND TREATMENTS THEREOF

(71) Applicants: ViiV Healthcare Company, Wilmington, DE (US); Janssen Sciences Ireland Unlimited Company, County Cork (IE)

(72) Inventors: Kenneth Churchill Campbell, Ware (GB); Urbain Alfons C. Delaet, Beerse (BE); James M. Goodrich, Research Triangle Park, NC (US); Juliette Segolène Guaquière, Ware (GB); Thomas Laughery, Research Triangle Park, NC (US); Dominique J. Limet, Brentford (GB); John C. Pottage, Collegeville, PA (US); Ludovic Sylvain Marc Renou, Stevenage (GB); Trevor R. Scott, Research Triangle Park, NC (US); Christian Seiler, Brentford (GB); Mary Woodward, Ware (GB)

(73) Assignees: ViiV Healthcare Company, Wilmington, DE (US); Janssen Sciences Ireland UC, Little Island (IE)

( * ) Notice: Subject to any disclaimer, the term of this patent is extended or adjusted under 35 U.S.C. 154(b) by 70 days.

(21) Appl. No.: 16/621,309

(22) PCT Filed: Jun. 27, 2018

(86) PCT No.: PCT/IB2018/054769
§ 371 (c)(1),
(2) Date: Dec. 11, 2019

(87) PCT Pub. No.: WO2019/003150
PCT Pub. Date: Jan. 3, 2019

(65) Prior Publication Data
US 2020/0113838 A1    Apr. 16, 2020

Related U.S. Application Data

(60) Provisional application No. 62/589,576, filed on Nov. 22, 2017, provisional application No. 62/535,290, filed on Jul. 21, 2017, provisional application No. 62/527,169, filed on Jun. 30, 2017.

(30) Foreign Application Priority Data

Oct. 18, 2017 (GB) .................................. 1717131
Nov. 22, 2017 (GB) .................................. 1719377
Apr. 20, 2018 (GB) .................................. 1806490

(51) Int. Cl.
| | |
|---|---|
| A61K 9/24 | (2006.01) |
| A61K 9/20 | (2006.01) |
| A61K 9/28 | (2006.01) |
| A61K 31/505 | (2006.01) |
| A61K 31/5365 | (2006.01) |
| A61P 31/18 | (2006.01) |

(52) U.S. Cl.
CPC ............ *A61K 9/209* (2013.01); *A61K 9/2095* (2013.01); *A61K 9/28* (2013.01); *A61K 31/505* (2013.01); *A61K 31/5365* (2013.01); *A61P 31/18* (2018.01)

(58) Field of Classification Search
None
See application file for complete search history.

(56) References Cited

U.S. PATENT DOCUMENTS

| | | | |
|---|---|---|---|
| 2015/0231079 A1* | 8/2015 | Malhotra | ........... A61K 31/4178 424/452 |
| 2016/0067255 A1 | 3/2016 | Babusis et al. | |
| 2016/0347766 A1* | 12/2016 | Jetti | ....................... A61P 31/12 |
| 2020/0113838 A1 | 4/2020 | Campbell et al. | |

FOREIGN PATENT DOCUMENTS

| | | | |
|---|---|---|---|
| EP | 1632232 | * | 3/2006 |
| EP | WO 2013153161 | * | 10/2013 |
| EP | 3645003 A2 | | 5/2020 |
| IN | WO2014/184553 | * | 11/2014 |

(Continued)

OTHER PUBLICATIONS

M2 Presswire) VIIV Healthcare begins phase III programme with dolutegravir/rilpivirine combination for HIV maintenance therapy; First programme to evaluate dual HIV maintenance therapy with dolutegravir and nlplvmne M2 Presswlre May 6, 2015 p. 1, abstract.
BlueCross BlueSh1eld of Arizona JULUCA Pharmacy Coverage Guidelines Jan. 18, 2018, p. 1.
Capetti A.F. et al., "Switch to Dolutegravir plus Rilpivirine Dual Therapy in cART-Experienced Subjects: An Observational Cohort", PLoS One. vol. 11, No. 10; 2016.

(Continued)

*Primary Examiner* — Tigabu Kassa
(74) *Attorney, Agent, or Firm* — Robert J. Smith

(57) ABSTRACT

Methods are provided for treating or preventing human immunodeficiency virus-1 (HIV-1) or human immunodeficiency virus-2 (HIV-2) in a virologically suppressed patient in need thereof comprising switching the patient from an antiretroviral treatment regimen comprising at least three antiretroviral agents to a treatment regimen comprising only two antiretroviral agents. In one aspect the two treatment regimen consists of dolutegravir, rilpivirine and at least one pharmaceutically acceptable excipient, diluent or carrier. In another aspect of the invention, there is provided a multi-layer tablet comprising dolutegravir or a pharmaceutically acceptable salt thereof and rilpivirine or a pharmaceutically acceptable salt thereof.

8 Claims, 17 Drawing Sheets

(56) References Cited

FOREIGN PATENT DOCUMENTS

| JP | 2015-534973 A | 12/2001 |
|---|---|---|
| WO | 2012068535 | 5/2012 |
| WO | 2014/064409 A1 | 5/2014 |
| WO | 2015059466 A1 | 4/2015 |
| WO | WO 2015/140569 A1 | 9/2015 |
| WO | WO 2016/016279 A1 | 2/2016 |

OTHER PUBLICATIONS

Deshpande R.D. et al. Bi-layer tablets—an emerging trend: a review // IJPSR. 2011. vol. 2(10), p. 2534-2544.

Pertsev I. M. Pharmaceutical and medico-biological aspects of medicaments, vol. 1, 1999, Kharkov: UkrFa], pp. 253-254.

Gantner et al., "Efficacy and Safety of Dolutegravir and Rilpivirine Dual Therapy as a Simplification Strategy: A Cohort Study," HIV Medicine, vol. 18, (2018), pp. 704-708.

\* cited by examiner

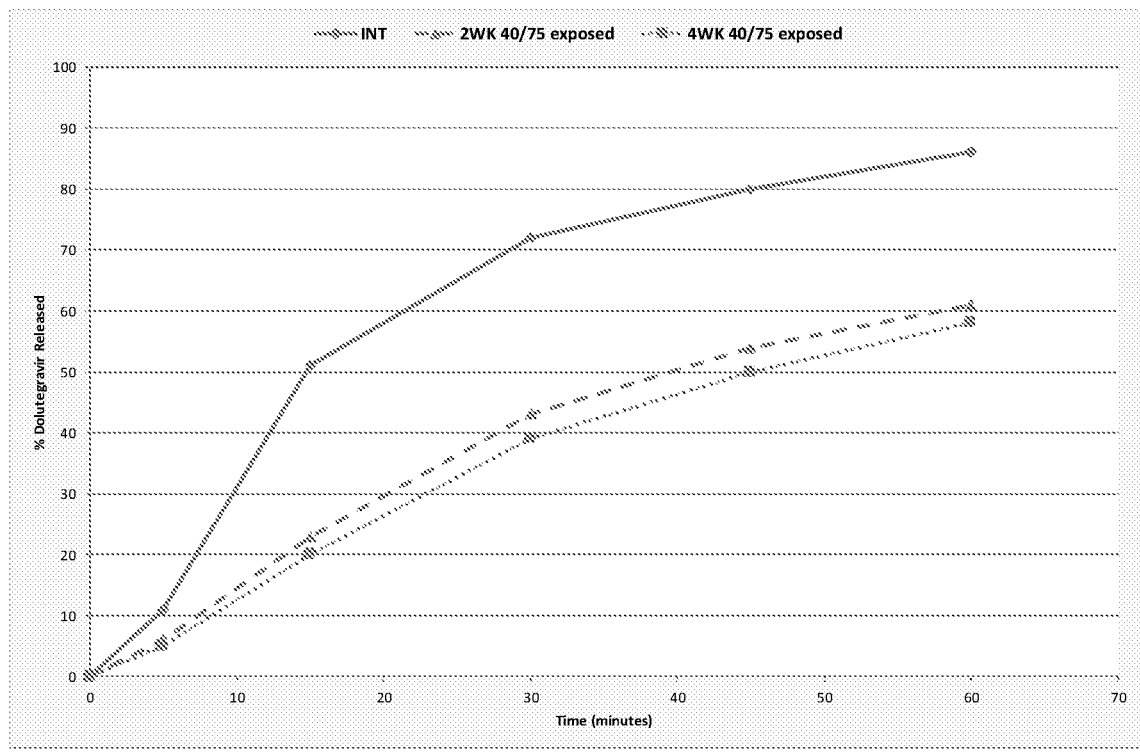
*Figure 1    Dolutegravir Release from Monolayer Tablets Following Open/Exposed Storage.   "INT" : Initial' "2WK 40/75 exposed": 40 °C, 75% RH for 2 weeks; "4WK 40/75 exposed" : 40 °C, 75% RH for 4 weeks*

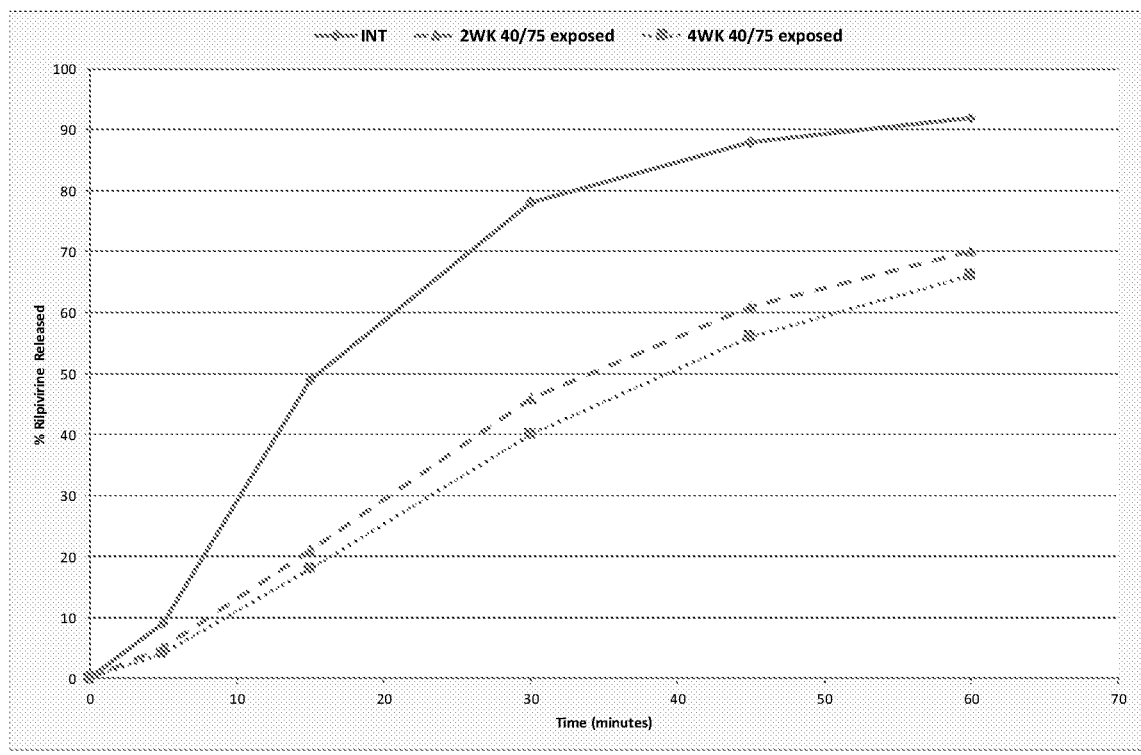
*Figure 2     Rilpivirine Release from Monolayer Tablets Following Open/Exposed Storage. "INT" : Initial' "2WK 40/75 exposed": 40 °C, 75% RH for 2 weeks; "4WK 40/75 exposed" : 40 °C, 75% RH for 4 weeks*

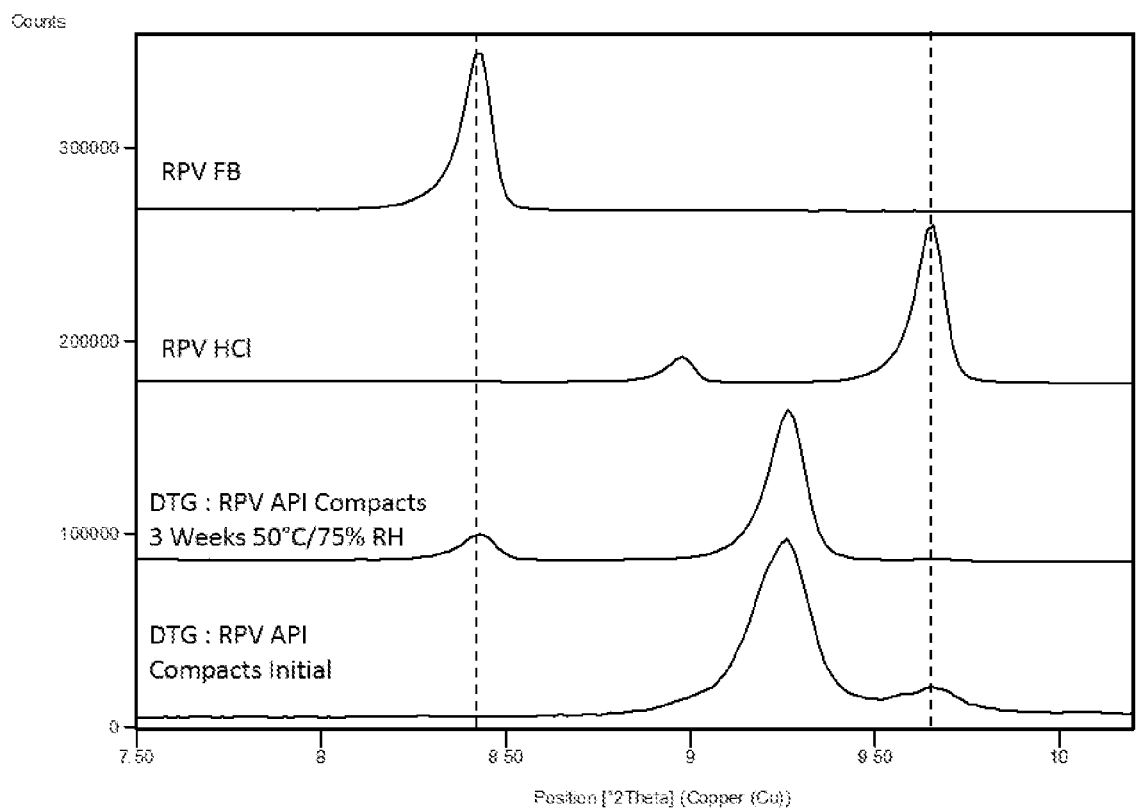
*Figure 3         XRPD spectrum of binary mixture of dolutegravir sodium and rilpivirine hydrochloride at initial time point and after 3 weeks at 50C/75% RH in comparison with rilpivirine hydrochloride salt and rilpivirine free base references*

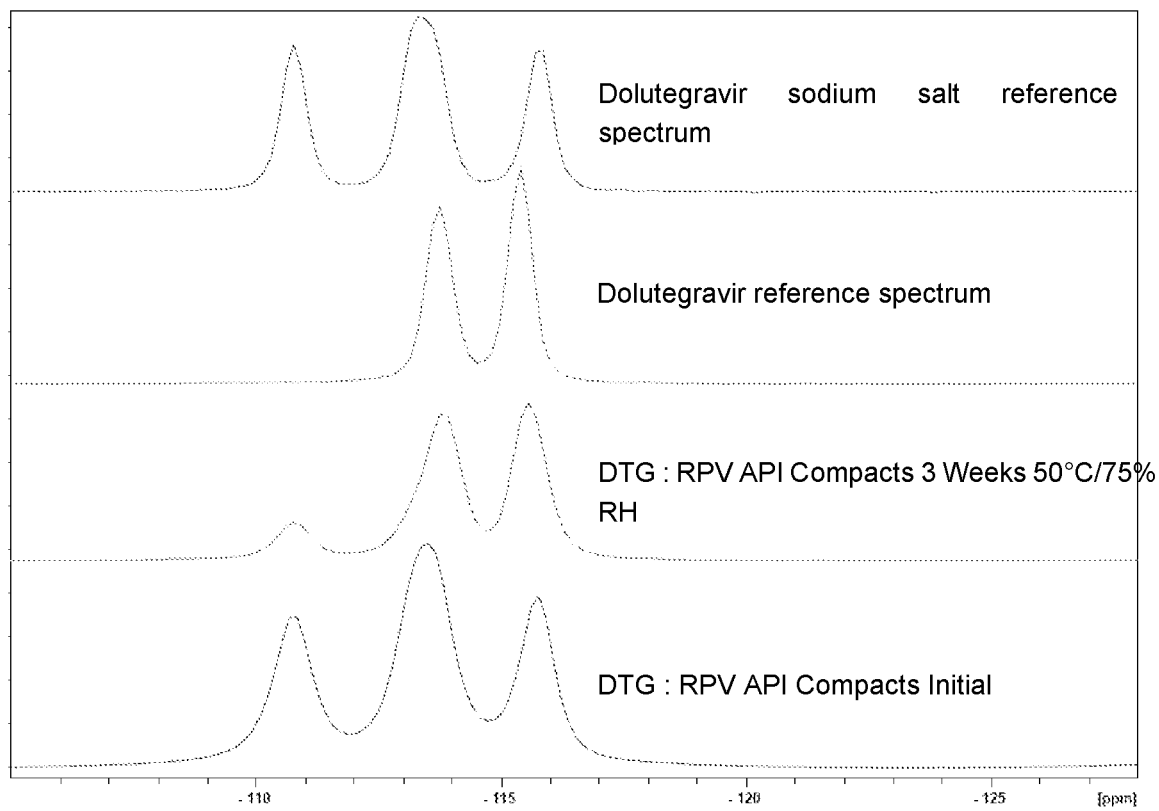
Figure 4  $^{19}F$ SSNMR spectrum of binary mixture of dolutegravir sodium and rilpivirine hydrochloride at initial time point and after 3 weeks at 50C/75% RH in comparison with dolutegravir sodium salt and dolutegravir free acid references

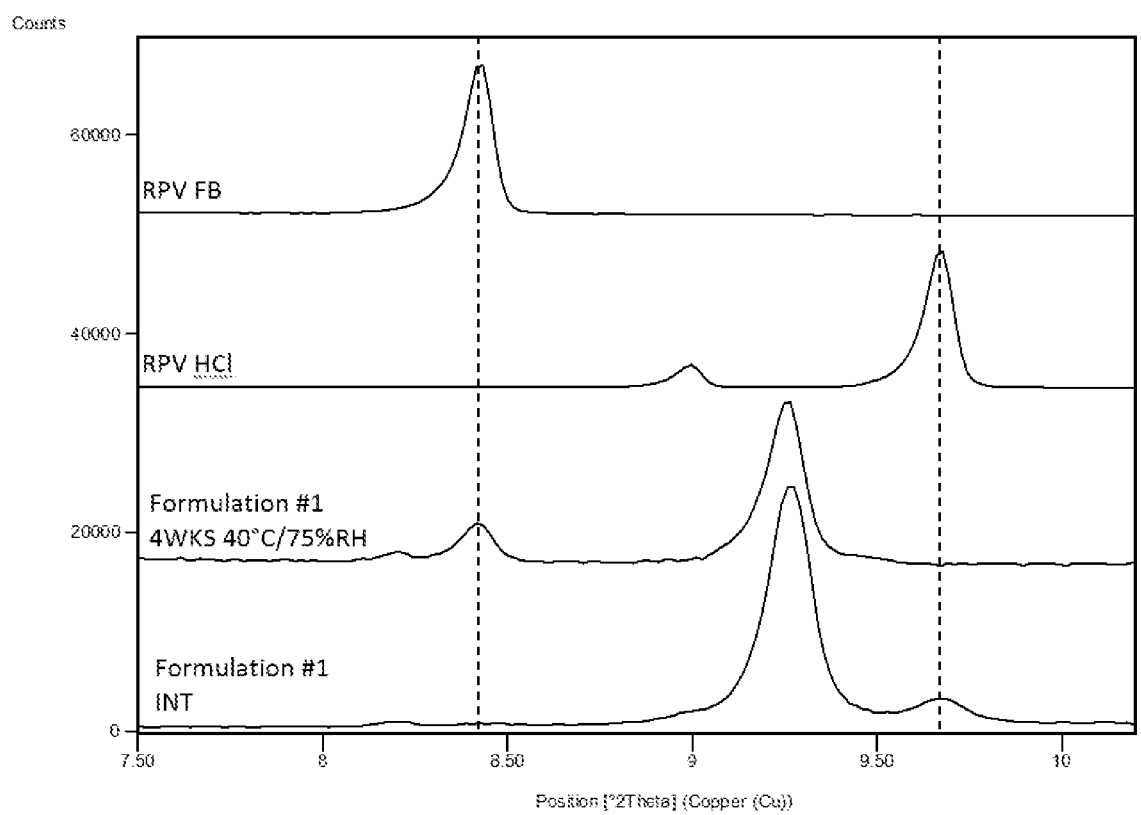
*Figure 5  XRPD spectrum of Formulation 1 at initial time point and after 4 weeks at 40°C/75% RH in comparison with rilpivirine hydrochloride salt and rilpivirine free base references*

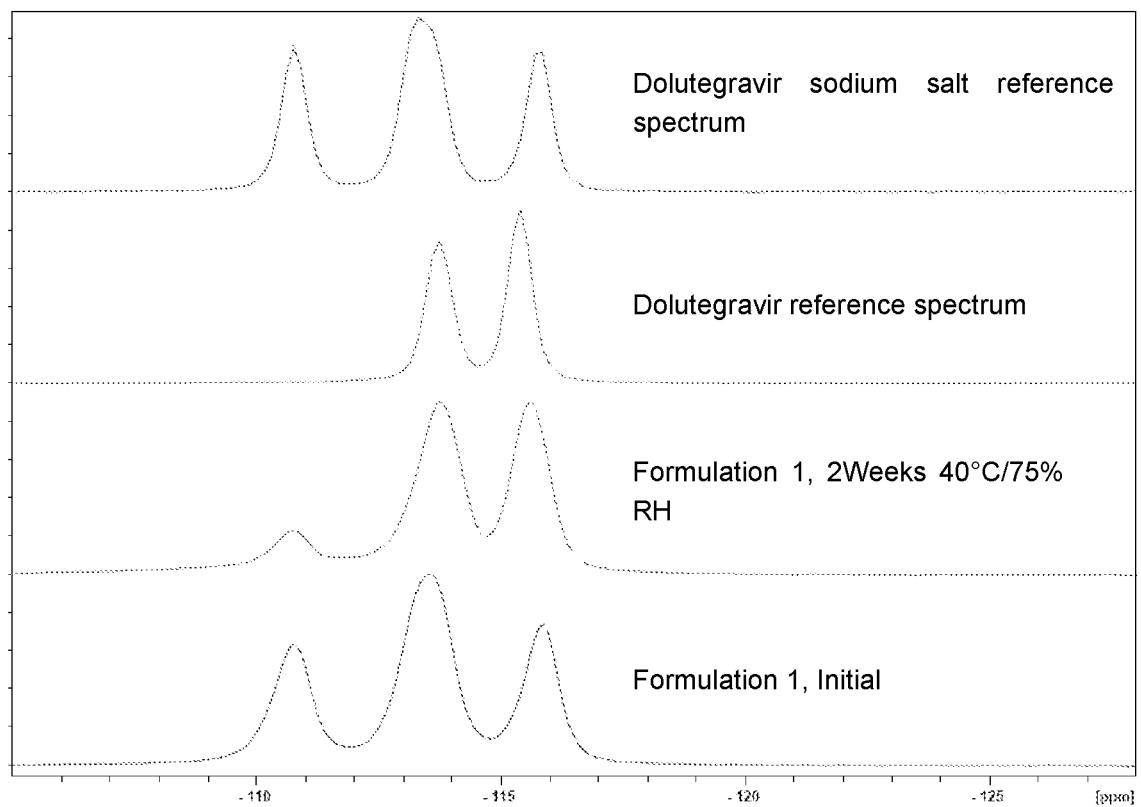
Figure 6   $^{19}F$ SSNMR spectrum of Formulation 1 at initial time point and after 2 weeks at 40°C/75% RH in comparison with dolutegravir sodium salt and dolutegravir free acid references

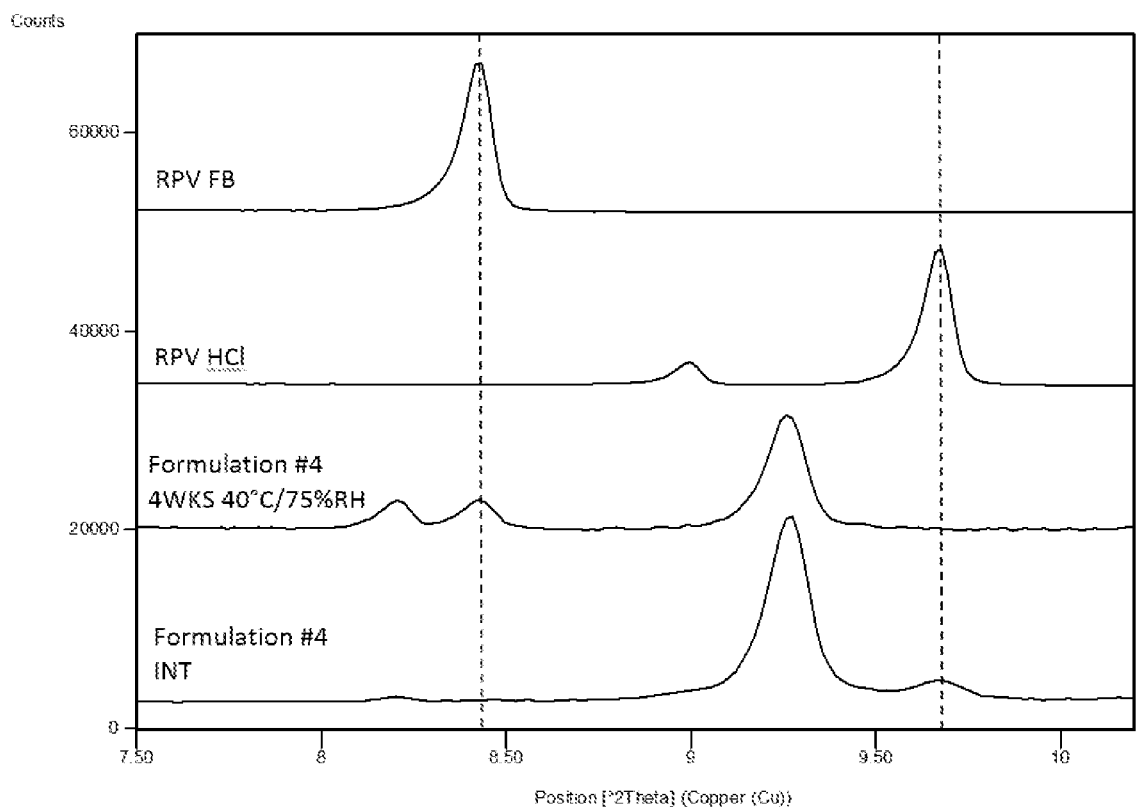
Figure 7  XRPD spectrum of Formulation 4 at initial time point and after 4 weeks at 40°C/75% RH in comparison with rilpivirine hydrochloride salt and rilpivirine free base references

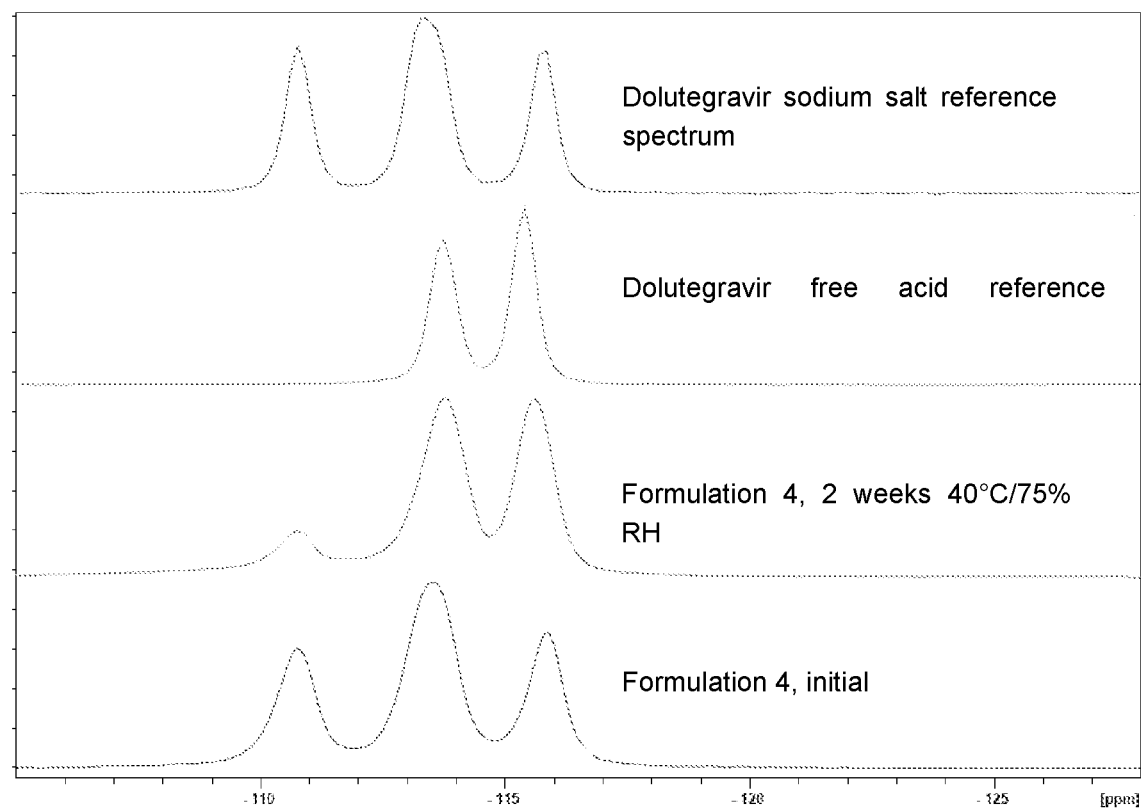
Figure 8  $^{19}F$ SSNMR spectrum of Formulation 4 at initial time point and after 2 weeks at 40°C/75% RH in comparison with dolutegravir sodium salt and dolutegravir free acid references

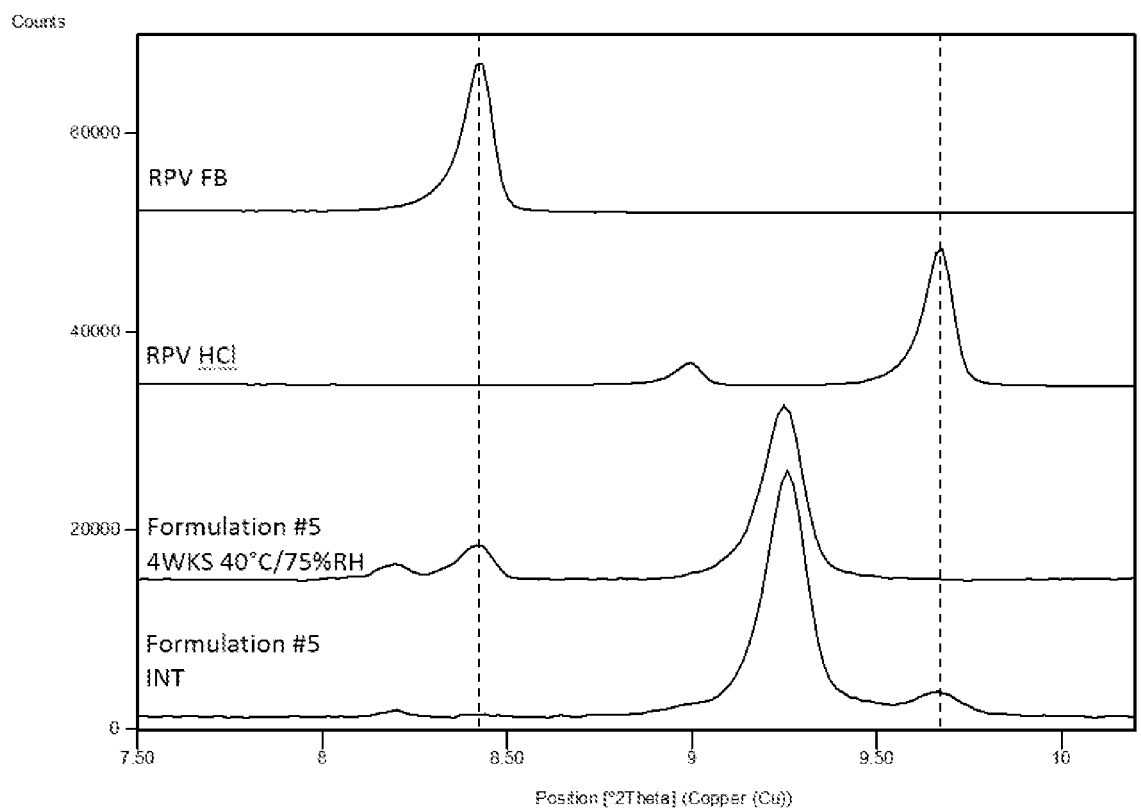
*Figure 9   XRPD spectrum of Formulation 5 at initial time point and after 4 weeks at 40°C/75% RH in comparison with dolutegravir sodium salt and dolutegravir free acid references*

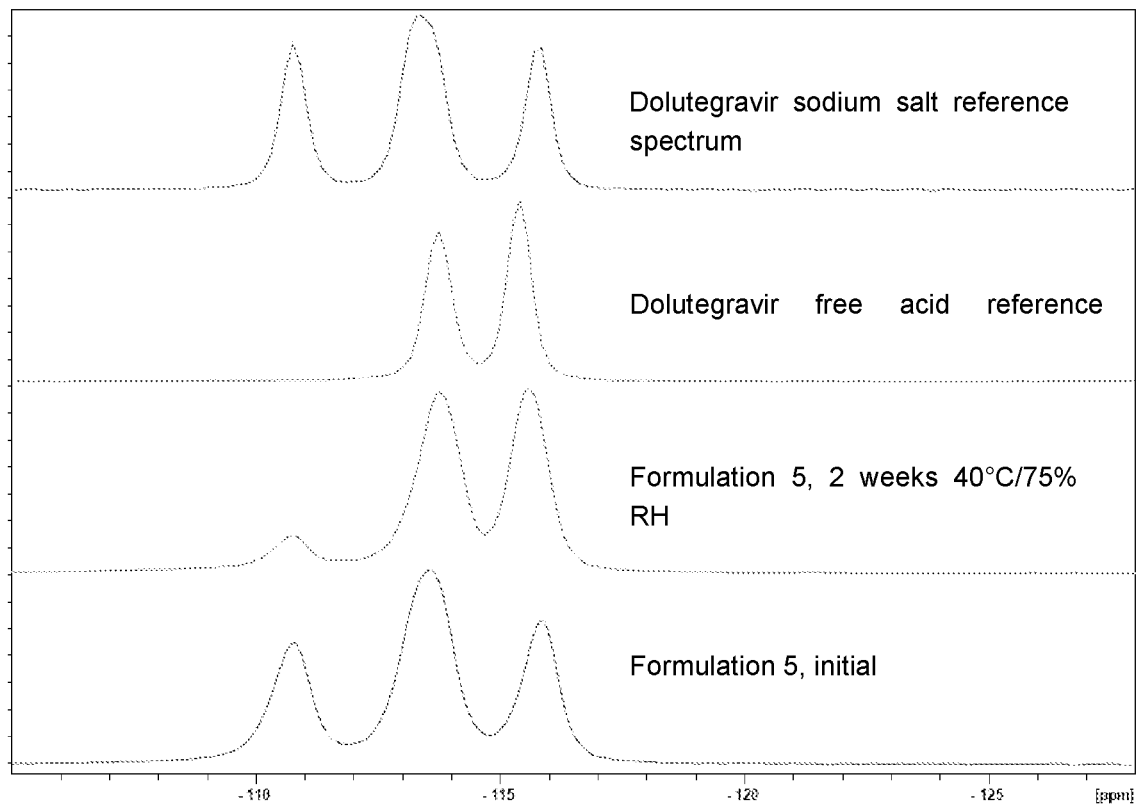
Figure 10 $^{19}F$ SSNMR spectrum of Formulation 5 at initial time point and after 2 weeks at 40°C/75% RH in comparison with dolutegravir sodium salt and dolutegravir free acid references

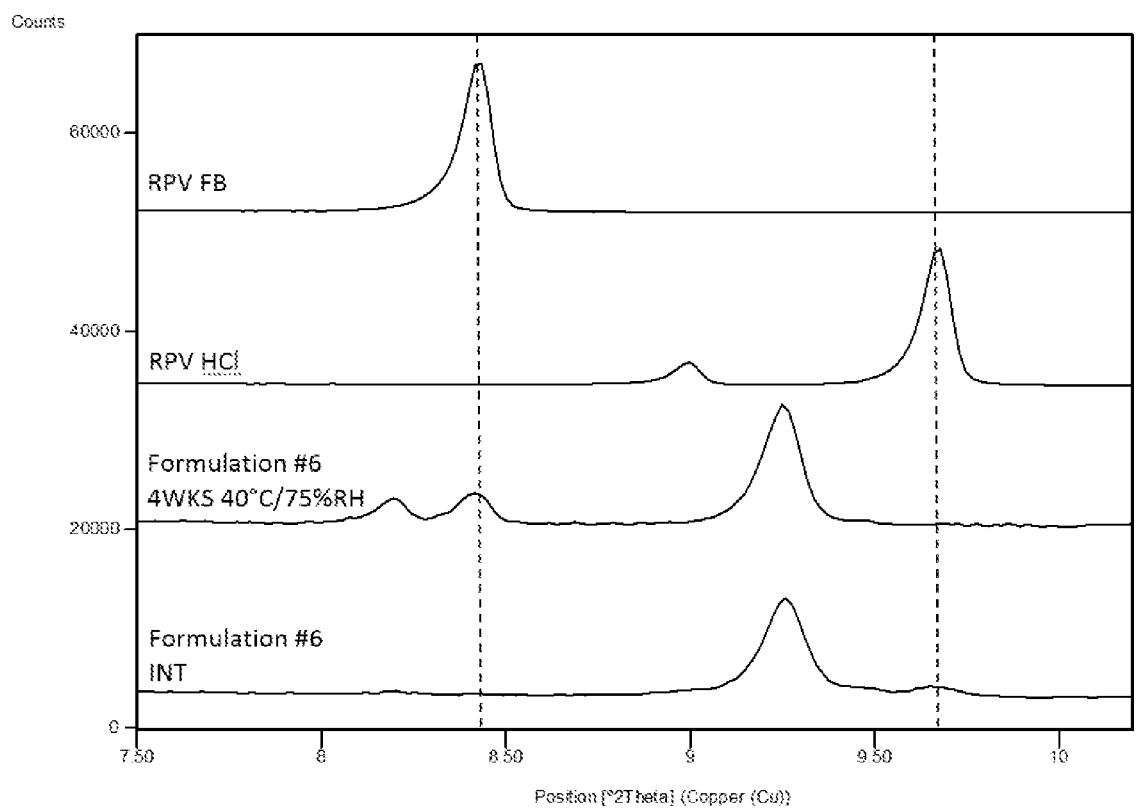
Figure 11 XRPD spectrum of Formulation 6 at initial time point and after 4 weeks at 40°C/75% RH in comparison with rilpivirine hydrochloride salt and rilpivirine free base references

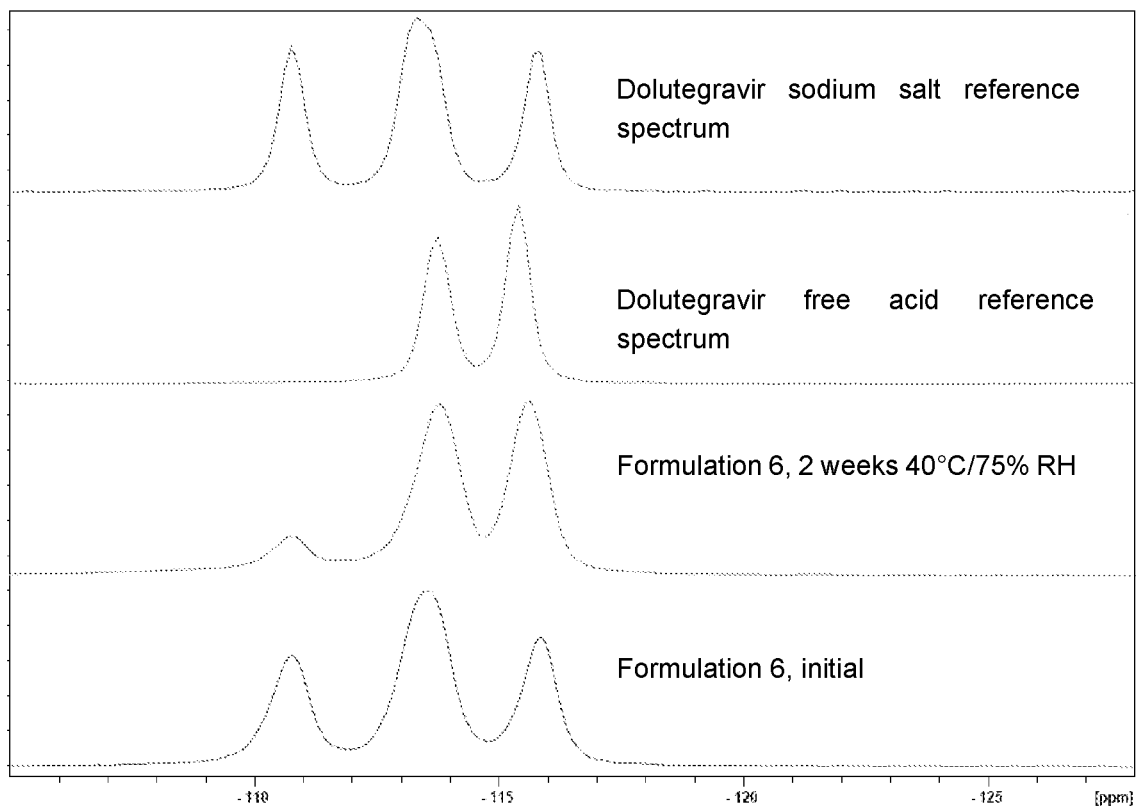
*Figure 12* $^{19}F$ *SSNMR spectrum of Formulation 6 at initial time point and after 2 weeks at 40°C/75% RH in comparison with dolutegravir sodium salt and dolutegravir free acid references*

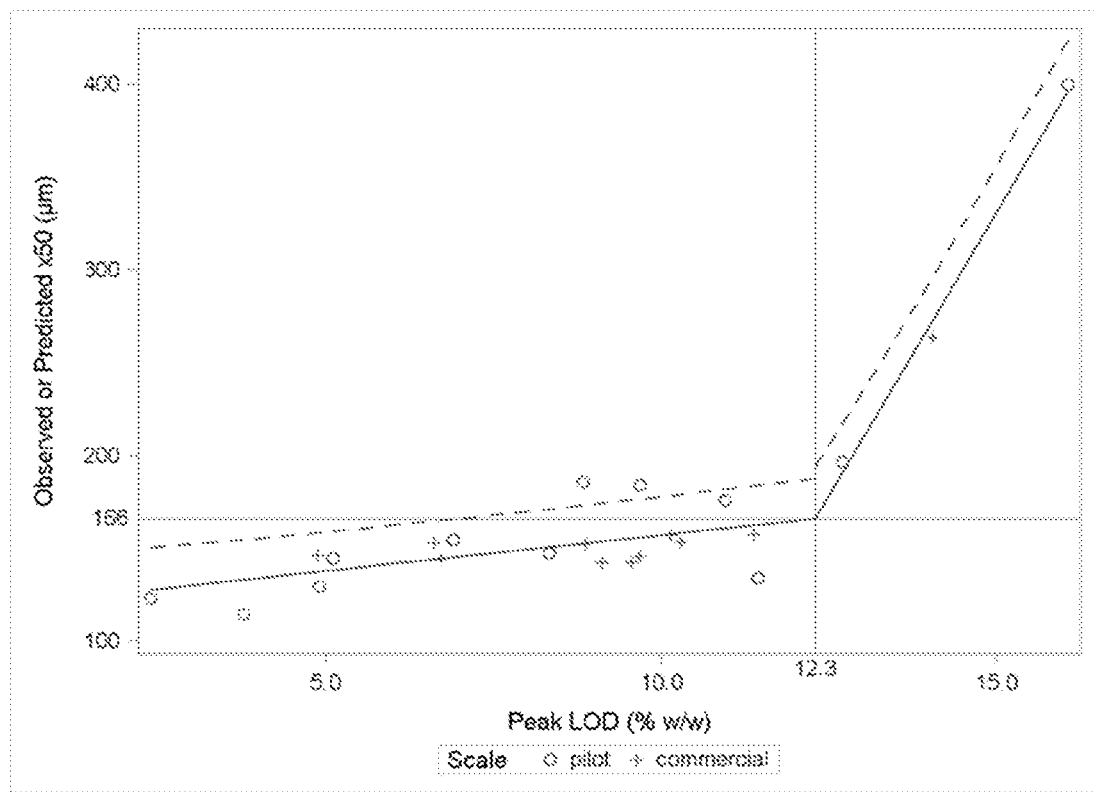
Figure 13: Observed mean size of dried particles as a function of peak LOD reached during the granulation process. "LOD" = loss on drying (the higher the peak LOD, the more liquid has been retained by the powder bed / granulation during the granulation process stage); "x50" = mean size of the resulting dried particles (also known as "d50")

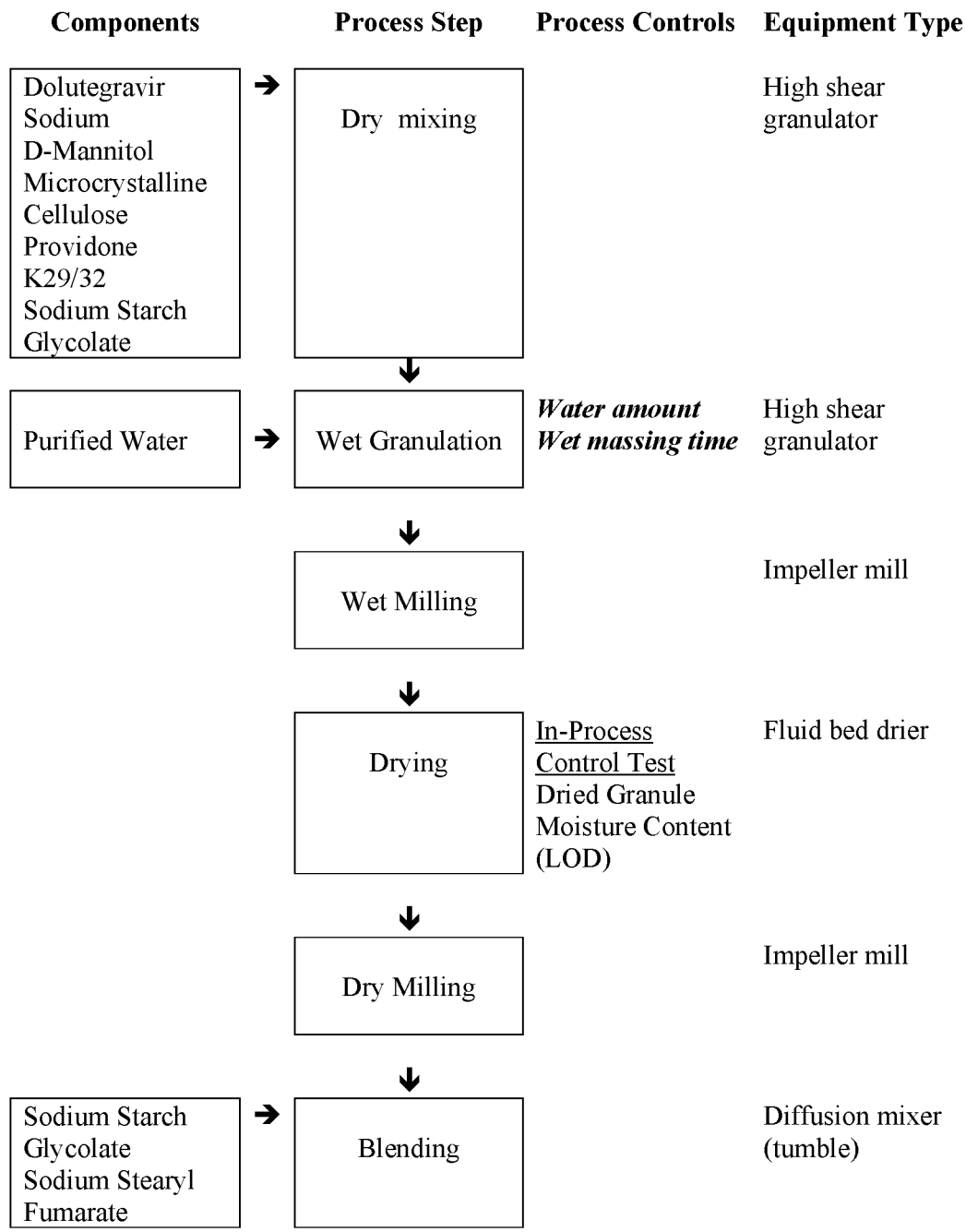
*Figure 14 Flow Diagram of the Manufacturing Process for Dolutegravir Compression Blend*

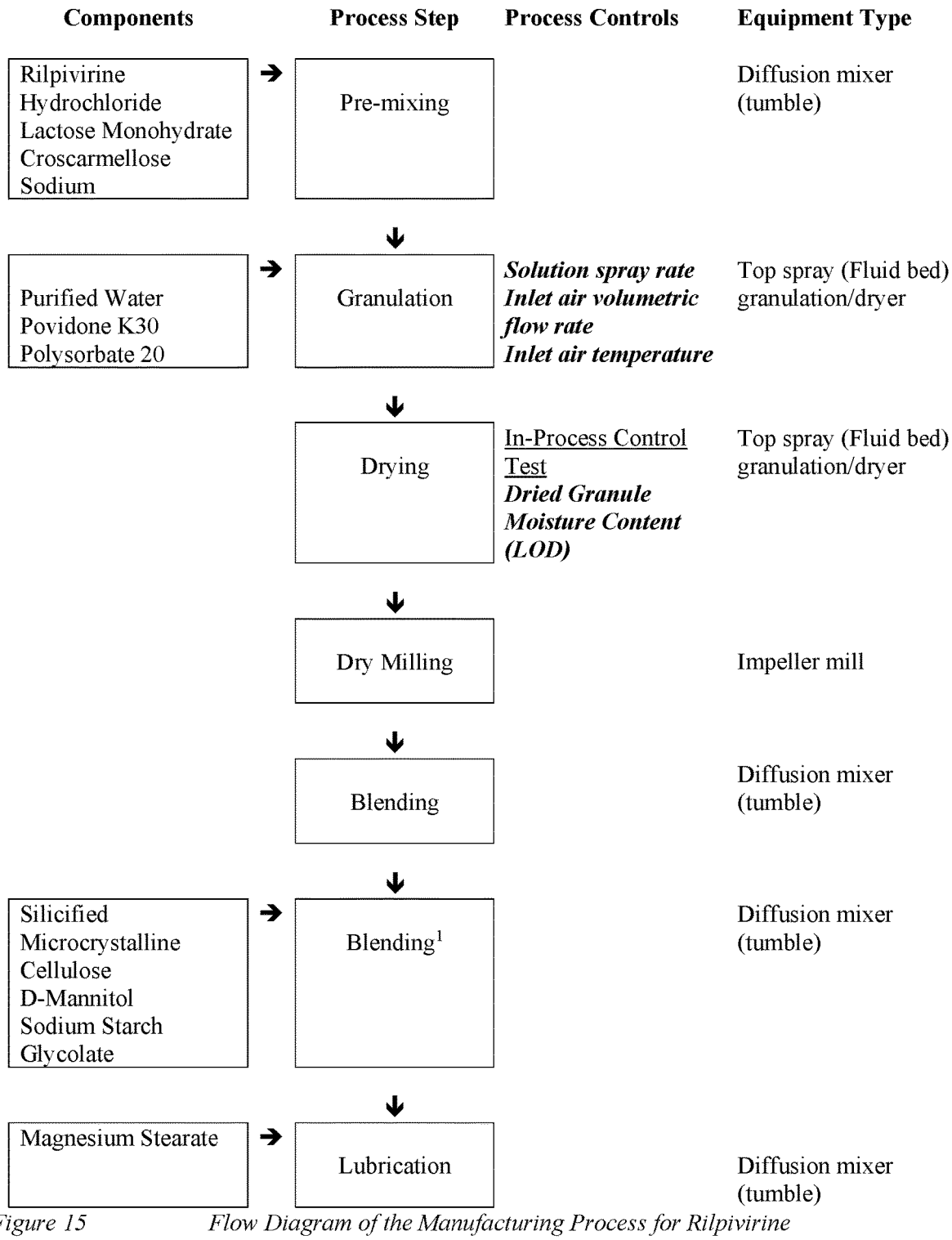
Figure 15    Flow Diagram of the Manufacturing Process for Rilpivirine Compression Blend

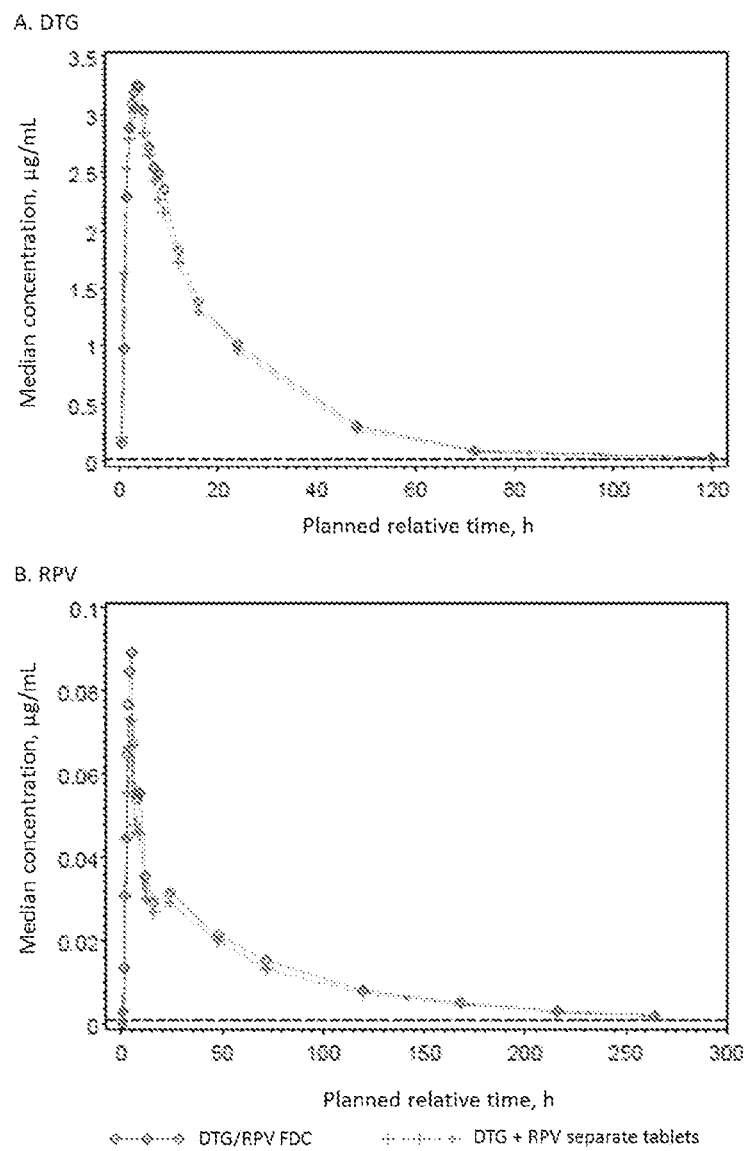
*Figure 16    Median plasma concentrations of (A) DTG and (B) RPV plotted by planned relative time after dosing. DTG, dolutegravir; RPV, rilpivirine.*

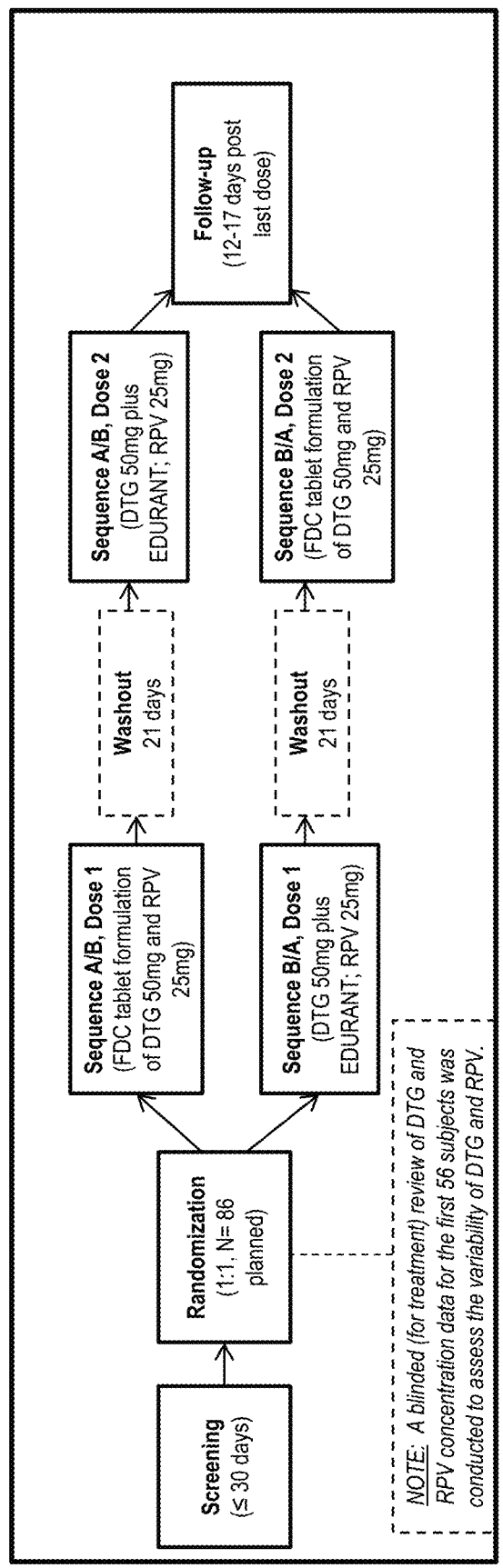
Figure 17 is a flow diagram of the bioequivalence of the fixed dose combination (FDC) tablets of Example 7 were evaluated versus co-administration of separate tablet formulations of Dolutegravir (DTG) 50mg (Tivicay) and Rilpivirine (RPV) 25mg (Edurant) in the fed state

COMBINATION AND USES AND TREATMENTS THEREOF

FIELD OF THE INVENTION

Disclosed are methods for treating human immunodeficiency virus or AIDS in a human using a combination comprising dolutegravir and rilpivirine, as well as compositions comprising dolutegravir and rilpivirine. Also, disclosed are methods for switching an antiviral regimen in a human with HIV in need thereof from a treatment regimen comprising three or more antiviral agents to a treatment regimen comprising only two antiviral agents. Further disclosed are formulations containing a two-drug combination of antiretroviral compounds useful against HIV. In particular, a bilayer combination formulation comprising dolutegravir sodium and rilpivirine hydrochloride is disclosed. In addition, the disclosed formulation is directed to a fixed dose combination tablet of dolutegravir sodium and rilpivirine hydrochloride having good physical properties, as well as efficacious delivery of the two active drug compounds.

BACKGROUND OF THE INVENTION

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al. N. Engl. J. Med. (1998) 338:853-860; Richman, D. D. Nature (2001) 410:995-1001).

A goal of antiretroviral (antiviral) therapy is to achieve viral suppression in the HIV infected patient. Treatment guidelines published by the United States Department of Health and Human Services provide that achievement of viral suppression requires the use of combination therapies, i.e., several drugs from at least two or more drug classes. (Panel on Antiretroviral Guidelines for Adults and Adolescents. Guidelines for the use of antiretroviral agents in HIV-1-infected adults and adolescents. Department of Health and Human Services. Available at http://aidsinfo.nih.gov/ContentFiles/AdultandAdolescentGL.pdf. Section accessed Mar. 14, 2013.) In addition, decisions regarding the treatment of HIV infected patients are complicated when the patient requires treatment for other medical conditions. To suppress HIV, the standard of care requires the use of multiple different drugs as well as to treat other conditions the patient may be experiencing. Therefore, the potential for drug interaction is a criterion for selection of a drug regimen. As such, there is a need for antiretroviral therapies having a decreased potential for drug interactions and with even more therapeutic potencies. A standard course of care for a patient infected with HIV is to treat them with a combination of three or more antiviral agents. Frequently, this treatment uses at least one antiretroviral agents targeting HIV reverse transcriptase (a "backbone") and/or one or more agents active against one or more different HIV targets, such as an HIV protease inhibitor, an HIV non-nucleoside or non-nucleotide inhibitor of reverse transcriptase, an HIV nucleoside or nucleotide inhibitor of reverse transcriptase, an HIV integrase inhibitor, an HIV non-catalytic site (or allosteric) integrase inhibitor, or a combination thereof. For certain patients infected with HIV or diagnosed with AIDS, there is an unmet medical need to treat them with fewer antiviral agents.

While ART has led to substantial increases in life expectancy and quality of life for HIV-infected persons, HIV infection requires lifelong treatment. This means that as HIV-infected individuals achieve life expectancies near those of persons without HIV, HIV-infected individuals are likewise starting to receive treatment for non-HIV, common conditions such as diabetes, cardiovascular disease, arthritis, osteoporosis, or other age-associated conditions and diseases. (Zhou et al., Total Daily Pill Burden in HIV-Infected Patients in the Southern United States, 2014 AIDS PATIENT CARE and STDs 28(6): 311-317.) This increased drug burden (of HIV patients also now taking medications for HIV-unrelated indications) raises risks of drug-drug interactions and overlapping toxicities, not to mention it increases the patient's healthcare costs and dosing hassle. (Zhou et al., AIDS PATIENT CARE and STDs 28(6): 311-317.) Further, increasing medication complexity may affect treatment adherence and virologic suppression. (Zhou et al., AIDS PATIENT CARE and STDs 28(6): 311-317.)

Fewer drugs in HIV infected patients are also desired for those that are likely to tolerate two drugs rather than more such as aging patients, those with advanced HIV infections or other diseases, or to avoid drug-drug interactions, and to limit side effects among patients. Thus, there is a need for new treatment regimens which suppress viral load in humans having HIV where the treatment regimen comprises only two antiviral agents.

Additionally, an issue associated with administration of HIV medications, including both dolutegravir and rilpivirine, is patient compliance. Because all HIV drugs must be taken as part of a combination regimen, there must be better ways to ensure patient compliance in taking medication as prescribed. If there are too many pills to swallow, at too many time intervals, then dosing becomes inconvenient and complicated, and patient compliance with the treatment regimen is less likely.

Thus, what is needed are new, easily administered, combination formulations containing potent antiretroviral drugs which are useful in the treatment of HIV infection. These new two drug formulations should be convenient and easy to administer, as well as showing good physical stability and low degradant levels.

In particular, stable, easily administered fixed dose combinations (FDCs) of dolutegravir and rilpivirine are desired.

SUMMARY OF THE INVENTION

In one embodiment of this invention methods are provided for treating or preventing human immunodeficiency virus (HIV) in a patient in need thereof, comprising administering to the patient a pharmaceutical composition comprising only two antiretroviral agents consisting essentially of a first antiretroviral agent and a second antiretroviral agent wherein the first antiretroviral agent is a therapeutically effective amount of a compound of Formula I:

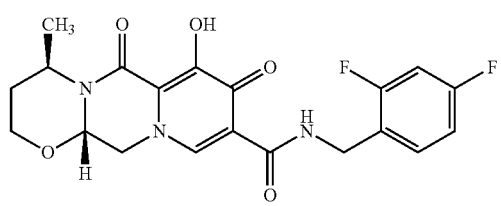

or with an additional pharmaceutically acceptable salt thereof; and
the second antiretroviral agent is a therapeutically effective amount of a compound of Formula II:

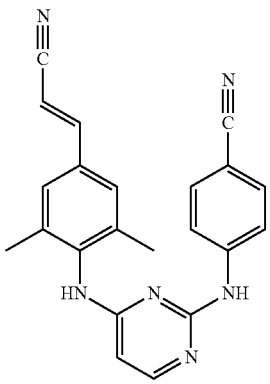

II or with an additional pharmaceutically acceptable salt thereof.

In another embodiment of this invention methods are provided for treating human immunodeficiency virus-1 (HIV-1) or human immunodeficiency virus-2 (HIV-2) (in particular for HIV-1)) in a virologically suppressed patient in need thereof comprising switching the patient from an antiretroviral treatment regimen comprising at least three antiretroviral agents to a treatment regimen comprising only two antiretroviral agents.

In one embodiment of this invention methods are provided for treating a patient infected with HIV-1 or HIV-2 (in particular for HIV-1) using a two-drug regimen essentially consisting of an integrase inhibitor and a non-nucleoside reverse transcriptase inhibitor where the patient's current antiretroviral regimen comprises three or more antiviral agents.

In yet another embodiment of this invention, kits are provided comprising:
  (1) A composition comprising a compound of Formula I, or with an additional pharmaceutically acceptable salt thereof, and a compound of Formula II, or with an additional pharmaceutically acceptable salt thereof; and
  (2) instructions for their coadministration.

In one embodiment of this invention, a combination of only two antiviral agents, those being a compound of Formula I, or a pharmaceutically acceptable salt thereof, and a compound of Formula II, or a pharmaceutically acceptable salt thereof, for use in treating HIV-1 or HIV-2 (in particular for HIV-1) in a virologically suppressed patient in need thereof comprising switching the patient from an antiretroviral treatment regimen comprising at least three antiretroviral agents to a treatment regimen comprising only two antiretroviral agents.

In another embodiment, there is provided a multilayer tablet comprising dolutegravir or a pharmaceutically acceptable salt thereof and rilpivirine or a pharmaceutically acceptable salt thereof.

In one embodiment, the tablet comprises 50 mg of dolutegravir free acid equivalent and 25 mg of rilpivirine free base equivalent.

In one embodiment, the tablet comprises 52.6 mg of dolutegravir sodium and 27.5 mg of rilpivirine hydrochloride.

In one embodiment, there is provided a multilayer tablet comprising dolutegravir or a pharmaceutically acceptable salt thereof and rilpivirine or a pharmaceutically acceptable salt thereof. In one embodiment, the tablet comprises 50 mg of dolutegravir free acid equivalent and 25 mg of rilpivirine free base equivalent. In one embodiment, the tablet comprises 52.6 mg of dolutegravir sodium and 27.5 mg of rilpivirine hydrochloride.

In one embodiment, there is provided a multilayer tablet comprising (a) dolutegravir or a pharmaceutically acceptable salt thereof and (b) rilpivirine or a pharmaceutically acceptable salt thereof, wherein (a) and (b) are present within separate layers in the multilayer tablet. In one embodiment, the multilayer tablet comprises (a) 50 mg of dolutegravir free acid equivalent and (b) 25 mg of rilpivirine free base equivalent, wherein (a) and (b) are present within separate layers in the multilayer tablet. In one embodiment, the multilayer tablet comprises (a) 52.6 mg of dolutegravir sodium and (b) 27.5 mg of rilpivirine hydrochloride, wherein (a) and (b) are present within separate layers in the multilayer tablet.

In one embodiment, there is provided a coated multilayer tablet comprising dolutegravir or a pharmaceutically acceptable salt thereof and rilpivirine or a pharmaceutically acceptable salt thereof. In one embodiment, the coated tablet comprises 50 mg of dolutegravir free acid equivalent and 25 mg of rilpivirine free base equivalent. In one embodiment, the coated tablet comprises 52.6 mg of dolutegravir sodium and 27.5 mg of rilpivirine hydrochloride.

In one embodiment, there is provided a coated multilayer tablet comprising (a) dolutegravir or a pharmaceutically acceptable salt thereof and (b) rilpivirine or a pharmaceutically acceptable salt thereof, wherein (a) and (b) are present within separate layers in the multilayer tablet. In one embodiment, the coated multilayer tablet comprises (a) 50 mg of dolutegravir free acid equivalent and (b) 25 mg of rilpivirine free base equivalent, wherein (a) and (b) are present within separate layers in the multilayer tablet. In one embodiment, the coated multilayer tablet comprises (a) 52.6 mg of dolutegravir sodium and (b) 27.5 mg of rilpivirine hydrochloride, wherein (a) and (b) are present within separate layers in the multilayer tablet.

In one embodiment the dolutegravir and rilpivirine layers are in direct contact.

It has been found that the use of a fixed dose combination may assist in achieving appropriate pharmacokinetic parameters and/or adequate tablet stability. Additionally, the use of a multilayer tablet as a fixed dose combination may also provide pharmacokinetic and/or stability benefits.

There is also provided a method of treatment of patients infected with HIV comprising administration of a multilayer tablet comprising dolutegravir or a pharmaceutically acceptable salt thereof and rilpivirine or a pharmaceutically acceptable salt thereof. In one embodiment, there is provided a method of treatment of patients infected with HIV comprising administration of a multilayer tablet comprising dolutegravir sodium and rilpivirine hydrochloride. In one embodiment, there is provided a method of treatment of patients infected with HIV comprising administration of a multilayer tablet comprising (a) 50 mg of dolutegravir free acid equivalent and (b) 25 mg of rilpivirine free base equivalent, wherein (a) and (b) are present within separate layers in the multilayer tablet. In one embodiment, there is provided a method of treatment of patients infected with HIV comprising administration of a multilayer tablet comprising (a) 52.6 mg of dolutegravir sodium and (b) 27.5 mg of rilpivirine hydrochloride, wherein (a) and (b) are present within separate layers in the multilayer tablet.

There is also provided a multilayer tablet comprising dolutegravir or a pharmaceutically acceptable salt thereof and rilpivirine or a pharmaceutically acceptable salt thereof for use in the treatment of HIV infection. In one embodiment, there is provided a multilayer tablet comprising dolutegravir sodium and rilpivirine hydrochloride for use in the treatment of HIV infection. In one embodiment, there is provided a multilayer tablet comprising (a) 50 mg of dolutegravir free acid equivalent and (b) 25 mg rilpivirine free base equivalent, wherein (a) and (b) are present within separate layers in the multilayer tablet, for use in the treatment of HIV infection. In one embodiment, there is provided a multilayer tablet comprising (a) 52.6 mg of dolutegravir sodium and (b) 27.5 mg rilpivirine hydrochloride, wherein (a) and (b) are present within separate layers in the multilayer tablet, for use in the treatment of HIV infection.

BRIEF DESCRIPTION OF THE DRAWINGS

FIG. 1 Dolutegravir Release from Monolayer Tablets Following Open/Exposed Storage.

FIG. 2 Rilpivirine Release from Monolayer Tablets Following Open/Exposed Storage.

FIG. 3 XRPD spectrum of binary mixture of dolutegravir sodium and rilpivirine hydrochloride at initial timepoint and after 3 weeks at 50° C./75% RH in comparison with rilpivirine hydrochloride salt and rilpivirine free base references.

FIG. 4 $^{19}$F SSNMR spectrum of binary mixture of dolutegravir sodium and rilpivirine hydrochloride at initial timepoint and after 3 weeks at 50° C./75% RH in comparison with dolutegravir sodium salt and dolutegravir free acid references.

FIG. 5 XRPD spectrum of monolayer formulation 1 of dolutegravir sodium and rilpivirine hydrochloride at initial timepoint and after 4 weeks at 40° C./75% RH in comparison with rilpivirine hydrochloride salt and rilpivirine free base references.

FIG. 6 $^{19}$F SSNMR spectrum of monolayer formulation 1 of dolutegravir sodium and rilpivirine hydrochloride at initial timepoint and after 2 weeks at 40° C./75% RH in comparison with dolutegravir sodium salt and dolutegravir free acid references.

FIG. 7 XRPD spectrum of monolayer formulation 4 of dolutegravir sodium and rilpivirine hydrochloride at initial timepoint and after 4 weeks at 40° C./75% RH in comparison with rilpivirine hydrochloride salt and rilpivirine free base references.

FIG. 8 $^{19}$F SSNMR spectrum of monolayer formulation 4 of dolutegravir sodium and rilpivirine hydrochloride at initial timepoint and after 2 weeks at 40° C./75% RH in comparison with dolutegravir sodium salt and dolutegravir free acid references.

FIG. 9 XRPD spectrum of monolayer formulation 5 of dolutegravir sodium and rilpivirine hydrochloride at initial timepoint and after 4 weeks at 40° C./75% RH in comparison with rilpivirine hydrochloride salt and rilpivirine free base references.

FIG. 10 $^{19}$F SSNMR spectrum of monolayer formulation 5 of dolutegravir sodium and rilpivirine hydrochloride at initial timepoint and after 2 weeks at 40° C./75% RH in comparison with dolutegravir sodium salt and dolutegravir free acid references.

FIG. 11 XRPD spectrum of monolayer formulation 6 of dolutegravir sodium and rilpivirine hydrochloride at initial timepoint and after 4 weeks at 40° C./75% RH in comparison with rilpivirine hydrochloride salt and rilpivirine free base references.

FIG. 12 $^{19}$F SSNMR spectrum of monolayer formulation 6 of dolutegravir sodium and rilpivirine hydrochloride at initial timepoint and after 2 weeks at 40° C./75% RH in comparison with dolutegravir sodium salt and dolutegravir free acid references.

FIG. 13 Observed mean size of dried particles as a function of peak LOD (loss on drying)—representing moisture content of the product at the end of fluid addition of the wet granulation process.

FIG. 14 Flow Diagram of the Manufacturing Process for Dolutegravir Compression Blend.

FIG. 15 Flow Diagram of the Manufacturing Process for Rilpivirine Compression Blend FIG. 16 Median plasma concentrations of (A) DTG and (B) RPV plotted by planned relative time after dosing. DTG, dolutegravir; RPV, rilpivirine.

FIG. 17 Flow Diagram of bioequivalence study of the bioequivalence of the fixed dose combination (FDC) tablets of Example 7 evaluated versus co-administration of separate tablet formulations of Dolutegravir (DTG) 50 mg (Tivicay) and Rilpivirine (RPV) 25 mg (Edurant) in the fed state.

DETAILED DESCRIPTION OF THE INVENTION

Definitions

The following terms in quotations used herein have the following meanings.

"% w/w" means the weight of a component as a percentage of the total weight of e.g. a layer or dosage form in which the component is present. For example, a composition comprising "5% w/w X" refers to a composition in which the weight of component X is 5% of the total weight of the composition.

The symbol "↓" means to lower a dosage or frequency of dosing.

The symbol "↑" means to raise a dosage or frequency of dosing.

The symbol "↔" means to keep a dosage and frequency of dosing the same.

"About" means within the margins of error of the field, art, or subject matter it refers to. The term "about" used in connection with a quantity is inclusive of the stated value and has the meaning dictated by the context (e.g., includes the degree of error associated with measurement of the particular quantity). For example, in certain nonlimiting example the term "about" in relation to a numerical value x refers to x±10%, x±5%, or x±1%.

The term "alkyl" refers to a saturated hydrocarbon chain having the specified number of carbon atoms. For example, "$C_{1-6}$alkyl" refers to an alkyl group having from 1 to 6 carbon atoms, for example 1 to 2 carbon atoms.

"ART-experienced" or "antiretroviral therapy-experienced" means with regards to a human, one currently, or in the past have been treated with one or more antiviral agents used to treat HIV or acquired immune deficiency syndrome (AIDS). As defined herein, "ART-experienced" includes HAART (Highly Active Anti-Retroviral Therapy) which is the use of multiple drugs that act on different viral targets.

As used herein "Area Under the Curve" or "AUC" is the area under the curve in a plot of the concentration of a substance in plasma against time. AUC can be a measure of the integral of the instantaneous concentrations during a time interval and has the units mass×time/volume, which can also be expressed as molar concentration×time, such as nM×day. AUC is typically calculated by the trapezoidal method (e.g., linear, linear-log). AUC is usually given for the time interval zero to infinity, and other time intervals are indicated (for example AUC (t1,t2) where t1 and t2 are the starting and finishing times for the interval). Thus, as used herein "AUC0-24 h" refers to an AUC over a 24-hour period, and "AUC0-4 h" refers to an AUC over a 4-hour period.

The term "between" with reference to two values includes those two values e.g. the range "between" 10 mg and 20 mg encompasses e.g. 10, 11, 12, 13, 14, 15, 16, 17, 18, 19 and 20 mg.

The term "$C_{1-6}$ alcohol" means a $C_{1-6}$alkyl group substituted by —OH.

As used herein, the term "co-administer" refers to administration of two or more agents within a 24-hour period of each other, for example, as part of a clinical treatment regimen. In other embodiments, "co-administer" refers to administration of two or more agents within 2 hours of each other. In other embodiments, "co-administer" refers to administration of two or more agents within 30 minutes of each other. In other embodiments, "co-administer" refers to administration of two or more agents within 15 minutes of each other. In other embodiments, "co-administer" refers to administration at the same time, either as part of a single formulation or as multiple formulations that are administered by the same or different routes.

The term "co-crystal" refers to a crystalline compound comprising two or more molecular components, e.g. wherein proton transfer between the molecular components is partial or incomplete.

As used herein the "coefficient of variation (CV)" is a measure of dispersion and it is defined as the ratio of the standard deviation to the mean. It is reported as a percentage (%) by multiplying the above calculation by 100 (% CV).

"Combination of the Invention" is a combination of a compound of Formula I, or with a pharmaceutically acceptable salt thereof, and a compound of Formula II, or a pharmaceutically acceptable salt thereof, wherein Formula I is dolutegravir and Formula II is rilpivirine.

"Composition(s) of the invention" means a composition(s) containing only two antiviral agents, those being a compound of Formula I, or with an additional pharmaceutically acceptable salt thereof, and a compound of Formula II, or with an additional pharmaceutically acceptable salt thereof, wherein Formula I is dolutegravir and Formula II is rilpivirine, but which composition may comprise other components.

The term "comprise" and variations thereof, such as "comprises" and "comprising", are to be construed in an open, inclusive sense, that is as "including, but not limited to".

As used herein "confidence interval" or "CI" is an interval in which a measurement or trial falls corresponding to a given probability p where p refers to a 90% or 95% CI and are calculated around either an arithmetic mean, a geometric mean, or a least squares mean. As used herein, a geometric mean is the mean of the natural log-transformed values back-transformed through exponentiation, and the least squares mean may or may not be a geometric mean as well but is derived from the analysis of variance (ANOVA) model using fixed effects.

The term "consist" and variations thereof, such as "consists" and "consisting", are to be construed narrowly, that is "including only".

The term "effective amount" refers to an amount that may be effective to elicit the desired biological or medical response, including the amount of a compound that, when administered to a subject for treating a disease, is sufficient to effect such treatment for the disease. The effective amount will vary depending on the compound, the disease and its severity and the age, weight, etc. of the subject to be treated. The effective amount can include a range of amounts.

"in one embodiment" or "in an embodiment" in various places throughout this specification are not necessarily all referring to the same embodiment. Furthermore, the particular features, structures, or characteristics may be combined in any suitable manner in one or more embodiments.

The term "fed" in relation to administration of a solid oral dosage form to a human subject means administration of the dosage form orally under fed conditions (moderate fat meal) e.g. administration within about 30 minutes of the human consuming a standardized meal of about 300 to 600 calories and about 10 to about 15 grams of fat. In some embodiments, "fed" refers to administration within about 30 minutes of the human consuming a high fat meal.

"HIV" or "human immunodeficiency virus" each means HIV-1 or HIV-2 (in particular for HIV-1), or any mutant, group, clinical isolate, subtype, or clade thereof.

"Regimen(s) of the invention" means a regimen(s) comprising an aspect of administration, formulation, route of administration, dose, dosing interval, and treatment duration using only two antiviral agents, those being a compound of Formula I, or with an additional pharmaceutically acceptable salt thereof, and a compound of Formula II, or with an additional pharmaceutically acceptable salt thereof, but which regimen may comprise or use other components.

As used herein "maximum plasma concentration" or "$C_{max}$" means the highest observed concentration of a substance (for example, dolutegravir or rilpivirine) in mammalian plasma after administration of the substance to the mammal.

As used herein, the term "patient" refers to a mammal, including a human.

The term "pharmaceutically acceptable" with respect to a substance refers to that substance which is generally regarded as safe and suitable for use without undue toxicity, irritation, allergic response, and the like, commensurate with a reasonable benefit/risk ratio. "Pharmaceutically acceptable" with regard to excipients includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzene sulfonic acid, benzoic acid, camphorsulfonic acid, citric acid, ethane sulfonic acid, fumaric acid, glucoheptonic acid, gluconic acid, lactic acid, maleic acid, malonic acid, mandelic acid, methane sulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

"Preventing" or "prevention of" a disease includes reducing the risk of developing the disease, i.e. causing the clinical symptoms of the disease not to develop in a subject that may be exposed to or predisposed to the disease but does not yet experience or display symptoms of the disease.

As used herein, the term "salts" includes co-crystals.

The term "segregated" as used in relation to certain components (e.g. A and B) within a tablet means that those components are physically discrete such that the presence of one component (e.g. A) does not substantially affect the stability in storage of the other component(s) (e.g. B) from which it is segregated. Typically, when components are segregated in a tablet then they will be present in separate layers in a multilayer tablet. By way of example, components A and B may be present in separate layers in a multilayer tablet, wherein (a) the layer containing component A is substantially free of component B and (b) the layer containing component B is substantially free of component A. The separate layers may be in contact with each other or may be separated e.g. by one or more additional layers.

As used herein "serum or plasma half-life" refers to the time required for half the quantity of a substance administered to a mammal to be metabolized or eliminated from the serum or plasma of the mammal by normal biological processes.

The term "solvate" means a molecular complex comprising a compound and one or more pharmaceutically acceptable solvent molecules. Examples of solvent molecules include water and $C_{1-6}$ alcohols, e.g. ethanol. When the solvate is water, the term "hydrate" may be used.

The term "substantially free" in relation to the presence of a given component within e.g. a composition means that less than 5% by weight of the composition (e.g. less than 1% by weight of the composition) is that given component. The word "substantially" does not exclude "completely" e.g. a composition which is "substantially free" from Y may be completely free from Y. Where necessary, the word "substantially" may be omitted from the definition of the invention.

"Therapeutically effective amount" or "effective amount" refers to that amount of the compound being administered that will prevent a condition (disorders), or will relieve to some extent one or more of the symptoms of the disorder being treated. Pharmaceutical compositions suitable for use herein include compositions wherein the active ingredients are contained in an amount sufficient to achieve the intended purpose. Determination of a therapeutically effective amount is well within the capability of those skilled in the art, especially in light of the detailed disclosure provided herein.

As used herein, "treatment", refers to inhibition, reduction, elimination or alleviation of a disease in a patient, or the improvement of an ascertainable measurement associated with a particular disorder, and may include the suppression of symptom recurrence in an asymptomatic patient such as a patient in whom a viral infection has become latent.

As used herein "$T_{max}$" refers to the observed time for reaching the maximum concentration of a substance in plasma of a mammal after administration of that substance to the mammal.

"Virologically suppressed" means detecting an HIV ribonucleic acid (RNA) copy number of less than a given number of copies per mL. For example, given number of copies is <50 c/ml. For example, using TaqMan 2.0. (Roche Diagnostics, Indianapolis, Ind., USA).

As used herein "weighted mean AUC" is the AUC divided by the time interval over which the time AUC is calculated. For instance, weighted mean AUC0-24 h would represent the AUC0-24 h divided by 24 hours.

As is understood in the art various methods may be employed to collect, measure and assess pharmacokinetic data such as active compound concentration in blood, plasma and/or other tissue.

Compounds

Dolutegravir inhibits HIV integrase by binding to the integrase active site and blocking the strand transfer step of retroviral deoxyribonucleic acid ("DNA") integration which is essential for the HIV replication cycle. DTG is an integrase strand transfer inhibitor (INSTI). Strand transfer biochemical assays using purified HIV-1 integrase and pre-processed substrate DNA resulted in $IC_{50}$ (Inhibitory Concentration at 50%) values of 2.7 nM (Kalama and Murphy, *Dolutegravir for the Treatment of HIV,* 2012 Exp. Op. Invest. Drugs 21(4): 523-530).

The chemical name of dolutegravir is (4R,12aS)—N-[(2,4-difluorophenyl)methyl]-7-hydroxy-4-methyl-6,8-dioxo-3,4,12,12a-tetrahydro-2H-pyrido[5,6]pyrazino[2,6-b][1,3]oxazine-9-carboxamide (CAS Registry Number 1051375-16-6). Certain regimens and compositions of the invention comprise a pharmaceutically acceptable form of dolutegravir, such as a pharmaceutically acceptable salt, hydrate and/or solvate thereof. An exemplary pharmaceutically acceptable salt of dolutegravir is dolutegravir sodium (marketed as "TIVICAY"). A sodium salt of dolutegravir and a specific crystalline form of this sodium salt or a hydrate thereof are disclosed in U.S. Pat. No. 8,624,023. Amorphous dolutegravir sodium is described in, for example, U.S. Pat. No. 9,206,197. Polymorphs, isomers, prodrugs, and esters of dolutegravir are also envisioned with respect to the present invention. Unless specified otherwise, the weight (mg) of dolutegravir is based on the weight of dolutegravir in its free form.

Dolutegravir has the following structural formula:

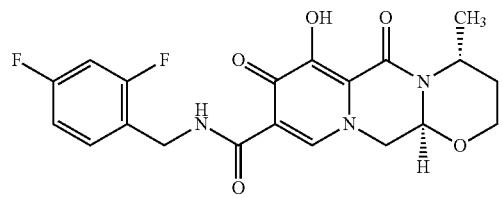 [SMILES: C[C@@H]1CCO[C@H]2Cn3cc(C(=O)NCc4ccc(F)cc4F)c(=O)c(O)c3C(=O)N12]

Dolutegravir is primarily metabolized by glucuronidation. Dolutegravir is considered to be a substrate of CYP3A4, but only to a minor extent of about 15%. Further, dolutegravir demonstrates induction or inhibition of cytochrome P450 (CYP) isozymes in vitro. See U.S. Pregrant Publication 2016/0184332.

"Dolutegravir based regimen" or "DTG based regimen" or "dolutegravir containing regimen" or "DTG containing regimen" as used herein means a regimen that includes the administration of dolutegravir or a pharmaceutically acceptable salt thereof (e.g., the administration of a pharmaceutical composition comprising dolutegravir or a pharmaceutically acceptable salt thereof).

Dolutegravir is approved for use in a broad population of HIV-infected patients. Dolutegravir was approved by the FDA in August 2013, by Health Canada in November 2013, and by the EMA in Europe in January 2014. It can be used to treat HIV-infected adults who have never taken HIV therapy (treatment-naïve) and HIV-infected adults who have previously taken HIV therapy (treatment-experienced), including those who have been treated with other integrase strand transfer inhibitors. TIVICAY is also approved for children aged 12 years and older weighing at least 40 kilograms (kg) who are treatment-naïve or treatment-experienced but have not previously taken other integrase strand transfer inhibitors.

As used herein, the term "DTG" is intended to refer to dolutegravir sodium. The chemical name of dolutegravir sodium is sodium (4R,12aS)-9-{[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate. The empirical formula is $C_{20}H_{18}F_2N_3NaO_5$ and the molecular weight is 441.36 g per mol. It has the following structural formula:

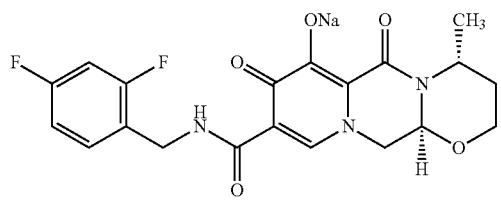

Dolutegravir sodium is a white to light yellow powder and is slightly soluble in water (Table 15).

TABLE 15

The solubilities of non-micronized dolutegravir sodium in various solvents at 25° C.

| Solvent | Solution pH | Solubility (mg/mL) | Descriptor |
|---|---|---|---|
| Water[2] | 10.1[1] | 3.176 | Slightly soluble |
| FaSSIF[2,3] | 6.5 | 0.239 | Very slightly soluble |
| FeSSIF[2,4] | 5.0 | 0.170 | Very slightly soluble |
| SGF[2,5] | 1.2 | 0.021 | Practically insoluble |

Note:
[1]Solution pH for water has been measured from a saturated solution at 21° C.
[2]Equilibrium solubility collected after 4 hours apart from SGF media which was collected at 8 hours.
[3]Fasted State Simulated Intestinal Fluid.
[4]Fed State Simulated Intestinal Fluid.
[5]Simulated Gastric Fluid.

Non-micronized dolutegravir sodium is very slightly soluble at pH 5.0 and 6.5, and practically insoluble at pH1.2 in aqueous media.

Methods of making dolutegravir have been described in, for example, U.S. Pat. No. 9,573,965. See also U.S. Pat. No. 8,217,034 and U.S. Pregrant Publication 2016/0184332.

Rilpivirine has the chemical formula $C_{22}H_{18}N_6$ and the chemical name 4-[[4-[[4-[(E)-2-cyanoethenyl]-2,6-dimethylphenyl]amino]-2-pyrimidinyl]amino]benzonitrile.

It has the structural formula set forth below:

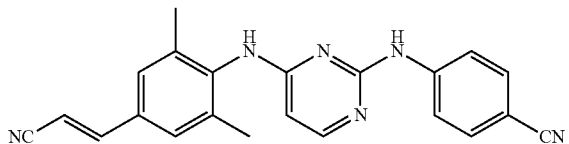 [SMILES: Cc1cc(/C=C/C#N)cc(C)c1Nc1ccnc(Nc2ccc(C#N)cc2)n1]

The compound is set forth and claimed in, inter alia, WO2003016306 and related national applications, the contents of which are incorporated herein by reference.

Rilpivirine is available from Janssen Sciences Ireland UC as EDURANT (rilpivirine hydrochloride).

As used herein, the term "RPV" is intended to refer to rilpivirine hydrochloride. The chemical name for rilpivirine hydrochloride is 4-[[4-[[4-[(E)-2-cyanoethenyl]-2,6-dimethylphenyl]amino]-2-pyrimidinyl]amino]benzonitrile hydrochloride. Its molecular formula is $C_{22}H_{18}N_6 \cdot HCl$ and its molecular weight is 402.88 g per mol. Rilpivirine hydrochloride has the following structural formula:

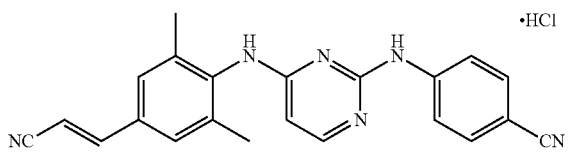 [SMILES: Cc1cc(/C=C/C#N)cc(C)c1Nc1ccnc(Nc2ccc(C#N)cc2)n1 ; Cl]

Rilpivirine hydrochloride is a white to almost white powder. It is practically insoluble in aqueous media (Table 16).

TABLE 16

The solubilities of rilpivirine hydrochloride in various aqueous media.

| Medium | Solution pH | Solubility (g/100 mL) | Descriptor |
|---|---|---|---|
| Water | 2.2 | 0.001 | Practically insoluble |
| 0.1N HCl | 1.1 | <0.001 | Practically insoluble |
| 0.01N HCl | 2.0 | 0.003 | Practically insoluble |
| Citrate-HCl | 2.0 | <0.001 | Practically insoluble |
| Citrate-NaOH | 5.0 | <0.001 | Practically insoluble |
| Phosphate Buffer | 6.9 | <0.001 | Practically insoluble |
| Borate-KCl— | 8.9 | <0.001 | Practically insoluble |
| Phosphate-NaOH | 11.9 | <0.001 | Practically insoluble |
| 0.1N NaOH | 12.9 | <0.001 | Practically insoluble |

The solubility descriptor is as defined in U.S. Pharmacopeia 27:
Practically insoluble or Insoluble: Parts of solvent required for 1 part of solute: greater than or equal to 10,000.
The solubility was determined as follows: An excess of the solute was equilibrated with the solvent at 20° C. for at least 24 hours.
After removing the undissolved compound, the concentration in solution was determined using UV spectrometry.

Method of Treating

One embodiment of the invention provides methods for treating or preventing human HIV-1 or HIV-2 (in particular for HIV-1) in a patient in need thereof, comprising administering to the patient a pharmaceutical composition comprising only two antiretroviral agents essentially consisting of a first antiretroviral agent and a second antiretroviral agent wherein the first antiretroviral agent is a therapeutically effective amount of a compound of Formula I, or with an additional pharmaceutically acceptable salt thereof; and the second antiretroviral agent is a therapeutically effective amount of a compound of Formula II, or with an additional pharmaceutically acceptable salt thereof.

Another embodiment methods are provided for treating a patient infected with human immunodeficiency virus type 1 (HIV-1) or a mutant thereof, human immunodeficiency virus type 2 (HIV-2) (in particular for HIV-1) or a mutant thereof, comprising administering to the patient a regimen comprising only two antiretroviral agents essentially consisting of a first antiretroviral agent and a second antiretroviral agent wherein the first antiretroviral agent is a therapeutically effective amount of a compound of Formula I, or with an additional pharmaceutically acceptable salt thereof; and the second antiretroviral agent is a therapeutically effective amount of a compound of Formula II, or with an additional pharmaceutically acceptable salt thereof.

In another embodiment, the pharmaceutical composition comprising only two antiretroviral agents as described herein essentially consists of a compound of Formula I, or with an additional pharmaceutically acceptable salt thereof; and a compound of Formula II, or with an additional pharmaceutically acceptable salt thereof, are provided.

In another embodiment, the pharmaceutical composition comprising two antiretroviral agents essentially consisting of a compound of Formula I, or with an additional pharmaceutically acceptable salt thereof; and a compound of Formula II, or with an additional pharmaceutically acceptable salt thereof; further comprises one or more pharmaceutically acceptable carriers, diluents or excipients.

In another embodiment, methods are provided for treating or preventing HIV in a patient comprising administering to a patient a therapeutically effective amount of a compound of Formula I, or with an additional pharmaceutically acceptable salt thereof; and the second antiretroviral agent is a therapeutically effective amount of a compound of Formula II, or with an additional pharmaceutically acceptable salt thereof, and one or more pharmaceutically acceptable carriers, diluents or excipients.

While it is possible for the active agents to be administered as a compound or as compounds, in one embodiment of the invention, they are administered as a pharmaceutical composition that can include contact with an acid or base, either in an ionic salt form or in contact with the base or acid (i.e., co-formers) without sharing ions. The salt, acid or base co-former, carrier, or diluent should be acceptable, in the sense of being compatible with the other ingredients and not deleterious to the recipient thereof. Pharmaceutically acceptable excipients for various different dosage forms are well-known in the art and include carriers, diluents, fillers, binders, lubricants, disintegrants, glidants, colorants, pigments, taste masking agents, sweeteners, flavorants, plasticizers, and any acceptable auxiliary substances such as absorption enhancers, penetration enhancers, surfactants, co-surfactants, and specialized oils. The proper excipient(s) is (are) selected based in part on the dosage form, the intended mode of administration, the intended release rate, and manufacturing reliability. Examples of carriers or diluents for oral administration include, but are not limited to: cornstarch, lactose, magnesium stearate, talc, microcrystalline cellulose, stearic acid, povidone, crospovidone, dibasic calcium phosphate, sodium starch glycolate, hydroxypropyl cellulose (e.g., low substituted hydroxypropyl cellulose), hydroxypropylmethyl cellulose (e.g., hydroxypropylmethyl cellulose 2910), sodium lauryl sulfate, mannitol, sodium stearyl fumarate, and talc. Examples of salts and acid or base co-formers include fumarate, hemifumarate, sodium, and hydrochloride.

In another embodiment, this invention provides a combination of a compound of Formula I, or with an additional pharmaceutically acceptable salt thereof, and a compound of Formula II, or with an additional pharmaceutically acceptable salt thereof, for use in medical therapy. The active agents of the disclosed combination therapy may be administered to a human in any conventional manner.

In another embodiment, the pharmaceutical composition further comprises at least one non antiretroviral (non-ARV) active agent. In another embodiment, a compound of Formula I, or with an additional pharmaceutically acceptable salt thereof, and a compound of Formula II, or with an additional pharmaceutically acceptable salt thereof, are co-administered in separate dosage forms. In another embodiment, a compound of Formula I, or with an additional pharmaceutically acceptable salt thereof, and a compound of Formula II, or with an additional pharmaceutically acceptable salt thereof, are co-administered in a single dosage form. In another embodiment, a compound of Formula I, or with an additional pharmaceutically acceptable salt thereof, and a compound of Formula II, or with an additional pharmaceutically acceptable salt thereof, are each taken once daily. In another embodiment, a compound of Formula I, or with an additional pharmaceutically acceptable salt thereof, and a compound of Formula II, or with an additional pharmaceutically acceptable salt thereof, are co-administered in a fixed dose combination. Another embodiment provides taking one or more of such combinations once, twice, three time daily or more, depending on the dose appropriate for a given patient. In another embodiment, a compound of Formula I, or with an additional pharmaceutically acceptable salt thereof, and a compound of Formula II, or with an additional pharmaceutically acceptable salt thereof, are co-administered in a single tablet. In another embodiment, a compound of Formula I, or with an additional pharmaceutically acceptable salt thereof, and a compound of Formula II, or with an additional pharmaceutically acceptable salt thereof, are orally co-administered. In another embodiment, a compound of Formula I, or with an additional pharmaceutically acceptable salt thereof, and a compound of Formula II, or with an additional pharmaceutically acceptable salt thereof, are either in liquid form or solid form or another form (e.g. a gel, sol, or emulsion) or combination of such forms suited to any of various routes of administration to a patient. In another embodiment, a compound of Formula I, or with an additional pharmaceutically acceptable salt thereof, and a compound of Formula II, or with an additional pharmaceutically acceptable salt thereof, are co-administered in a single tablet taken orally once daily. The tablet is preferably a swallowable tablet. It may optionally be coated with a film coat comprising, in essence, any suitable inert coating material known in the art.

Other embodiments comprise pharmaceutical compositions formulated into various types of dosage forms, for example as solutions or suspensions, or as tablets, capsules, granules, pellets or sachets for oral administration. The above lists of forms is not exhaustive. A pharmaceutical composition of the present invention can be manufactured according to standard methods known in the art. Granulates according to the invention can be obtained by dry compaction or wet granulation. These granulates can subsequently be mixed with e.g. suitable disintegrating agents, glidants and lubricants and the mixture can be compressed into tablets or filled into sachets or capsules of suitable size.

Tablets can also be obtained by direct compression of a suitable powder mixture, i.e. without any preceding granulation of the excipients. Suitable powder or granulate mixtures according to the invention are also obtainable by spray drying, lyophilisation, melt extrusion, pellet layering, coating of the active pharmaceutical ingredient or any other suitable method. The so obtained powders or granulates can be mixed with one or more suitable ingredients and the resulting mixtures can either be compressed to form tablets or filled into sachets or capsules. The above mentioned methods known in the art also include grinding and sieving techniques permitting the adjustment of desired particle size distributions.

In one embodiment, a single dosage form containing as the only two antiretroviral agents a compound of Formula I, or with an additional pharmaceutically acceptable salt thereof, and a compound of Formula II, or with an additional pharmaceutically acceptable salt thereof, is administered 4 hours before or 6 hours after taking antiacids, containing aluminum, magnesium hydroxide, and/or calcium carbonate. In one embodiment, a single dosage form containing a compound of Formula I, or with an additional pharmaceutically acceptable salt thereof, and a compound of Formula II, or with an additional pharmaceutically acceptable salt thereof, is administered 4 hours before or 6 hours after taking products containing polyvalent cations (eg. Mg or Al). In one embodiment, a single dosage form containing a compound of Formula I, or with an additional pharmaceutically acceptable salt thereof, and a compound of Formula II, or with an additional pharmaceutically acceptable salt thereof, is administered 4 hours before or 6 hours after taking calcium or iron supplements. Alternatively, the single dosage form containing a compound of Formula I, or with an additional pharmaceutically acceptable salt thereof, and a compound of Formula II, or with an additional pharmaceutically acceptable salt thereof, and supplements containing calcium or iron is taken with food.

In yet another embodiment, methods are provided wherein one or both of the two antiviral agents consisting of a compound of Formula I, or with an additional pharmaceutically acceptable salt thereof, and a compound of Formula II, or with an additional pharmaceutically acceptable salt thereof, is taken with food, such as a food that comprises at least a moderate or higher fat content. In one aspect, a food is considered a high fat food if it provides more than 30% of energy from fat. In some instances, high fat food provides more than 35% of energy from fat. In one aspect, a food is considered a moderate fat food if it provides between 20% to 35% or between 25% to 35% of energy from fat.

In yet another embodiment, the $AUC_{(0-\infty)}$ of the compound of Formula I, or with an additional pharmaceutically acceptable salt thereof, is increased by at least 80% and $C_{max}$ of the compound of Formula I, or with an additional pharmaceutically acceptable salt thereof, is increased by at least 70% in a patient that takes a composition of a compound of Formula I, or with an additional pharmaceutically acceptable salt thereof, and a compound of Formula II, or with an additional pharmaceutically acceptable salt thereof, with food that contains at least a moderate or higher fat content than compared with fasted conditions. In some aspects, moderate- and high-fat meals taken with the two antiretroviral agents each increased a compound of Formula I, or with an additional pharmaceutically acceptable salt thereof, $AUC_{(0-\infty)}$ by approximately 87% and $C_{max}$ by approximately 75%. In some instances, $AUC_{(0-\infty)}$ of a compound of Formula I, or with an additional pharmaceutically acceptable salt thereof is increased by approximately 70%, 75%, 80%, 85%, 90%, 95% or 100% in a patient when taken with a moderate- or high-fat food or meal compared with fasted conditions. In some instances, $C_{max}$ of a compound of Formula I, or with an additional pharmaceutically acceptable salt thereof is increased by approximately 70%, 75%, 80%, 85%, 90%, 95% or 100% in a patient when taken with a moderate- or high-fat food or meal compared with fasted conditions.

In some instance, a compound of Formula II, or with an additional pharmaceutically acceptable salt thereof, $AUC_{(0-\infty)}$ is increased by 57% and 72% and $C_{max}$ by 89% and 117% with moderate- and high-fat meals respectively, compared with fasted conditions. In some instances, $AUC_{(0-\infty)}$ of a compound of Formula II, or with an additional pharmaceutically acceptable salt thereof is increased by approximately 50%, 55%, 60%, 65%, 70%, 75%, 80%, 85%, 90%, 95% or 100% in a patient when taken with a moderate- or high-fat food or meal compared with fasted conditions. In some instances, $C_{max}$ of a compound of Formula II, or with an additional pharmaceutically acceptable salt thereof is increased by approximately 70%, 75%, 80%, 85%, 90%, 95%, 100%, 105%, 110%, 115%, or 120% in a patient when taken with a moderate- or high-fat food or meal compared with fasted conditions. When a compound of Formula II, or with an additional pharmaceutically acceptable salt thereof, was taken with only a protein-rich nutritional drink, exposures were 50% lower than when taken with a meal.

In yet another embodiment, the $AUC_{(0-\infty)}$ of the compound of Formula II, or with an additional pharmaceutically acceptable salt thereof, is increased by at least 50% and $C_{max}$ of the compound of Formula II, or with an additional pharmaceutically acceptable salt thereof, is increased by at least 80% in a patient that takes a pharmaceutical composition of a compound of Formula I, or with an additional pharmaceutically acceptable salt thereof, and a compound of Formula II, or with an additional pharmaceutically acceptable salt thereof, with food that contains at least a moderate or higher fat content than compared with fasted conditions.

In an additional embodiment, Formula I is (4R,12aS)-9-{+[(2,4-difluorophenyl)methyl]carbamoyl}-4-methyl-6,8-dioxo-3,4,6,8,12,12a-hexahydro-2H-pyrido[1',2':4,5]pyrazino[2,1-b][1,3]oxazin-7-olate.

In another embodiment, Formula I is dolutegravir sodium (Formula Ia) and/or the equivalent to 50 mg. of dolutegravir free acid.

In an additional embodiment, Formula II is 4-[[4-[[4-[(E)-2-cyanoethenyl]-2,6-dimethylphenyl]amino]-2-pyrimidinyl]amino]benzonitrile.

In another embodiment, Formula II is rilpivirine hydrochloride (Formula IIa) and/or the equivalent to 25 mg. of rilpivirine free base.

In another embodiment, a compound of Formula I, or with an additional pharmaceutically acceptable salt thereof, does not statistically significantly alter $C_{max}$ value of Formula II, or with an additional pharmaceutically acceptable salt thereof, compared with the $C_{max}$ value of Formula II, or with an additional pharmaceutically acceptable salt thereof, when taken as monotherapy. As is understood in the art, pharmacokinetic parameters such as $C_{max}$ and AUC can be measured within a single human or patient or from baseline to a selected endpoint in a group of patients. By way of example, the $C_{max}$ value of a compound of Formula II can be compared in a single patient or as an average mean in a patient(s) receiving a compound of Formula II or with an additional pharmaceutically acceptable salt thereof as monotherapy or in combination with a compound of Formula I or with an additional pharmaceutically acceptable salt thereof. Statistical significance can be calculated by several methods know in the art including, but not limited to, calculating confidence interval (CI) and/or p-value.

Following oral administration of dolutegravir, peak plasma concentrations were observed 2 to 3 hours postdose. With once-daily dosing, pharmacokinetic steady state is achieved within approximately 5 days with average accumulation ratios for AUC, $C_{max}$, and $C_{24}$ hour ranging from 1.2 to 1.5. Dolutegravir is a P-gp substrate in vitro. The absolute bioavailability of dolutegravir has not been established.

After oral administration, the maximum plasma concentration ($C_{max}$) of rilpivirine is generally achieved within 4 to 5 hours. The absolute bioavailability of rilpivirine is unknown.

In another embodiment, the patient has received three or more antiviral agents prior to receiving the pharmaceutical composition of dolutegravir and rilpivirine. For example a patient might have received antiviral regimen (two nucleoside reverse transcriptase inhibitors [NRTIs]+a third agent). The third agent could be either integrase inhibitor (INI), non-nucleoside reverse transcriptase inhibitor (NNRTI), or protease inhibitor (PI). In one embodiment, the patient has received an antiretroviral regimen comprising bictegravir, tenofovir or tenofovir prodrug, such as tenofovir disoproxil fumarate (TDF) or TAF (including hemi-fumarate and mono-fumarate), or emtricitabine prior to receiving the pharmaceutical composition of dolutegravir and rilpvirine. In another embodiment, the patient has shown resistance to either bictegravir, tenofovir, and/or emtricitabine prior to receiving the pharmaceutical composition of dolutegravir and rilpvirine. In a more preferred embodiment, a patient is switched to a pharmaceutical composition of dolutegravir and rilpvirine from a regimen comprising bictegravir (e.g. a combination of bictegravir, TAF, and emtricitabine) when he/she is infected with bictegravir resistant strain having mutation(s) at Q148R and/or Q148K.

In one embodiment of the invention methods are provided of treating or preventing HIV-1 or HIV-2 (in particular for HIV-1) in a virologically suppressed patient in need thereof comprising switching the patient from an antiretroviral treatment regimen comprising at least three antiretroviral agents to a treatment regimen comprising only two antiretroviral agents.

In another embodiment of the invention is a method of treating HIV-1 or HIV-2 (in particular for HIV-1) in a virologically suppressed patient in need thereof comprising switching the patient from an antiretroviral treatment regimen comprising at least three antiretroviral agents to a treatment regimen comprising only two antiretroviral agents wherein the first antiviral agent is a therapeutically effective amount of a compound of Formula I, or with an additional pharmaceutically acceptable salt thereof; and the second antiviral agent is a therapeutically effective amount of a compound of Formula II, or with an additional pharmaceutically acceptable salt thereof. Thus, in one embodiment, methods are provided of treating HIV-1 or HIV-2 (in particular for HIV-1) in a virologically suppressed patient in need thereof comprising switching the patient from an antiretroviral treatment regimen comprising at least three antiretroviral agents to a treatment regimen comprising only two antiretroviral agents essentially consisting of dolutegravir sodium (or with other suitable cation) equivalent to 50 mg dolutegravir free acid and rilpivirine hydrochloride (or with other suitable acid) equivalent to 25 mg of rilpivirine free base and at least one inactive ingredient.

In another embodiment of the invention is a method of treating or preventing HIV-1 or HIV-2 (in particular for HIV-1) in a virologically suppressed patient in need thereof comprising switching the patient from an antiretroviral treatment regimen comprising at least three antiretroviral agents to a treatment regimen comprising only two antiretroviral agents essentially consisting of about 50 mg. per dose of a compound of Formula I, or with an additional pharmaceutically acceptable salt thereof, and about 25 mg. per dose of a compound of Formula II, or with an additional pharmaceutically acceptable salt thereof. In another embodiment, a method or composition comprises between about 1 mg. and 200 mg. of a compound of Formula I, or with an additional pharmaceutically acceptable salt thereof, and between about 1 mg. and 200 mg. of a compound of Formula II, or with an additional pharmaceutically acceptable salt thereof. In another embodiment, a method or composition comprises between 10 mg. and 100 mg. of a compound of Formula I, or with an additional pharmaceutically acceptable salt thereof, and between 10 mg. and 100 mg. of a compound of Formula II, or with an additional pharmaceutically acceptable salt thereof.

Yet another embodiment comprises such equivalents of 10 mg., 20 mg, 25 mg., 30, mg, 35 mg, 40 mg, 45 mg, 50 mg., 75 mg., 100 mg. of a compound of Formula I, or with an additional pharmaceutically acceptable salt thereof, and 10 mg., 20 mg, 25 mg., 30 mg, 35 mg, 40 mg, 45 mg, 50 mg., 75 mg., 100 mg. of a compound of Formula II, or with an additional pharmaceutically acceptable salt thereof. In a further embodiment, a tablet, or other composition may comprise with an additional pharmaceutically acceptable form of dolutegravir equivalent to 50 mg. dolutegravir free acid and comprise with an additional pharmaceutically acceptable form of rilpivirine equivalent to 25 mg. of rilpivirine free base.

Provided as an embodiment for any dose range of the invention is each integer dose amount between each end number of a dose range. For example, a dose range from 15 mg. to 50 mg. would also include 16 mg., 17 mg., and so on up to 49 mg (including all decimal points, fractions, and integers, in between each value). A value of about 50 mg. would include values greater than 45 mg. and also values less than 55 mg. Other therapeutically effective doses of dolutegravir and rilpivirine can be determined or optimized using known pharmaceutical or clinical practices.

In one embodiment, the antiviral regimens may each comprise any number of steps or undergo any number of manipulations and the compositions used in each regimen may comprise any number of components, such as excipients or biologically active compounds (e.g., non-antiviral pharmaceutical compounds); however, with regard to the number of antiviral agents in the first antiviral regimen and its composition that number is limited to three or more antiviral agents, but no fewer, and with regard to the number of antiviral agents in the second antiviral regimen and its composition that number is limited to two antiviral agents, no more nor fewer.

In one embodiment a treatment regimen is provided that comprises switching from an antiviral treatment regimen comprising at least three antiviral agents comprising of one or more antiviral compounds selected from the group of: an HIV protease inhibitor, an HIV non-nucleoside or non-nucleotide inhibitor of reverse transcriptase, an HIV nucleoside or nucleotide inhibitor of reverse transcriptase, an HIV integrase inhibitor, MK8591 (EFdA), an HIV non-catalytic site (or allosteric) integrase inhibitor, an HIV entry inhibitor (e.g., a CCR5 inhibitor, a gp41 inhibitor (i.e., a fusion inhibitor) or a CD4 attachment inhibitor (e.g., combinectin), a CXCR4 inhibitor, a gp120 inhibitor, a G6PD or an NADH-oxidase inhibitor, an HIV vaccine, a latency reversing agent (e.g., a histone deacetylase inhibitor, a proteasome inhibitor, a protein kinase C (PKC) activator, or a BRD4 inhibitor), a compound that targets HIV capsid (a "capsid inhibitor"; e.g., a capsid polymerization inhibitor or a capsid disrupting compound, an HIV nucleocapsid p7 (NCp7) inhibitor, an HIV p24 capsid protein inhibitor), a pharmacokinetic enhancer, an immune-based therapy (e.g., a Pd-1 modulator, a Pd-LI modulator, a CTLA4 modulator, an ICOS modulator, an OX40 modulator, or the like, a toll-like receptor modulator, an IL-15 agonist, an anti-HIV antibody, a bispecific antibody or an "antibody-like" therapeutic protein (e.g., a DART, a DUOBODY, a BITE, an XmAb, a TandAb, a Fab derivative) including those targeting a HIV gp120 or gp41, combination drug for HIV, an HIV p 17 matrix protein inhibitor, an IL-13 antagonist, a peptidylprolyl cis-trans isomerase A modulator, a protein disulfide isomerase inhibitor, a complement C5a receptor antagonist, a DNA methyltransferase inhibitor, an HIV vif gene modulator, a Vif dimerization antagonist, an HIV-1 viral infectivity factor inhibitor, a TAT protein inhibitor, an HIV-1 Nef modulator, an Hck tyrosine kinase modulator, a mixed lineage kinase-3 (MLK-3) inhibitor, an HIV-1 splicing inhibitor, aRev protein inhibitor, an integrin antagonist, a nucleoprotein inhibitor, a splicing factor modulator, a COMM domain containing protein 1 modulator, an HIV ribonuclease H inhibitor, a retrorocyclin modulator, a CDK-9 inhibitor, a dendritic ICAM-3 grabbing nonintegrin 1 inhibitor, an HIV GAG protein inhibitor, an HIV POL protein inhibitor, acomplement Factor H modulator, a ubiquitin ligase inhibitor, a deoxycytidine kinase inhibitor, a cyclin dependent kinase inhibitor, a proprotein convertase PC9 stimulator, an ATP-dependent RNA helicase DDX3X inhibitor, a reverse transcriptase priming complex inhibitor, an HIV gene therapy, a PI3K inhibitor, a compound, such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380 (Japan Tobacco), US 20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), W02014/100323 (Gilead Sciences), WO2012/145728 (Gilead Sciences), WO 2013/159064 (Gilead Sciences) and WO 2012/003498 (Gilead Sciences) and WO 2013/006792 (Pharma Resources), and other drugs for treating HIV.

In one embodiment a treatment regimen is provided that comprises switching from an antiviral treatment regimen comprising at least three antiviral agents. In another embodiment, a treatment regimen is provided that comprises switching from an antiviral treatment regimen comprising bictegravir, tenofovir or tenofovir prodrug, such as tenofovir disoproxil fumarate (TDF) or TAF (including hemi-fumarate and mono-fumarate), and/or emtricitabine.

In another embodiment the regimen comprises switching from using a composition of the invention to using a composition comprising a combination comprising one or more of the aforementioned antiviral compounds. Another embodiment provides a method comprising an antiretroviral regimen comprising two NRTIs and one or more of an antiretroviral agent selected from the group consisting of an INI, an NNRTI, or a PI.

In another embodiment of the method the human or patient is virologically suppressed. By way of example a patient is considered virologically suppressed if the patient has an HIV copy number of between 0 and 200 copies per mL, less than 20 copies per mL, 50 copies per mL, 100 copies per mL, and/or 200 copies per mL. Provided also as an embodiment for any copy number of the invention are each integer copy number between each end number of a copy number range. For example, a copy number range from 20 copies per mL to 50 copies per mL would also include 21, 22, 23 up to 49 copies per mL.

An embodiment of the invention provides a composition of the invention administered to a patient infected with wild-type HIV-1 or HIV-2 (in particular for HIV-1), an HIV clade B virus, an HIV of M clade A, B, C, D, E, F, G, or H or an HIV group O virus, or mutants thereof.

An embodiment of a regimen of the invention provides administering a composition of the invention to a patient infected with a certain mutant HIV-1 virus or HIV-2 (in particular for HIV-1) virus, such as a mutant virus comprising a single amino acid substitution or two or more substitutions. Certain of such regimens provide administering a composition of the invention to a patient infected with an INSTI substitution mutant, such as a raltegravir-resistant mutant, or an elvitegravir-resistant mutant.

HIV mutations showing NRTI resistance is well documented. Examples of HIV mutations which show resistance to TAF (tenofovir alafenamide fumarate) (TAF has the same resistance profile tenovofir and tenofovir disoproxil) and FTC (emtricitabine) are published, such as, in Characterization of HIV-1 Resistance to Tenofovir Alafenamide In vitro, Antimicrobial Agents and Chemotherapy, vN. A. Margot et al., Volume 59 Number 10 (2015). Also is published online at https://hivdb.stanford.edu/dr-summary/resistance-notes/NRTI/.

Also provided is an embodiment that is a regimen of the invention or composition of the invention administered to or used to treat an anti-retroviral treatment (ART) experienced patient. A certain embodiment provides that this patient is also virologically suppressed.

Regimens of the invention and compositions of the invention are used to treat patients with infected wild type or mutant HIV or virus comprising an HIV integrase homolog. In another embodiment, the invention provides a method to administer a composition of the invention to a treatment-experienced patient, such as a patient that is virologically-suppressed.

In another embodiment the patient has HIV-1 or HIV-2 (in particular for HIV-1) RNA less than 50 copies per mL prior to switching from an antiretroviral treatment regimen comprising at least three antiretroviral agents to a treatment regimen comprising only two antiretroviral agents. In another embodiment, the patient has HIV-1 or HIV-2 (in particular for HIV-1) RNA less than 50 copies per mL prior to switching from an antiretroviral treatment regimen comprising at least three antiretroviral agents to a treatment regimen comprising a compound of Formula I or with an additional pharmaceutically acceptable salt thereof; and a compound of Formula II, or with an additional pharmaceutically acceptable salt thereof. In another embodiment, the switching to a treatment regimen comprising a compound of Formula I or with an additional pharmaceutically acceptable salt thereof; and a compound of Formula II, or with an additional pharmaceutically acceptable salt thereof occurs after at least 6 months of virologically suppression (HIV-1 RNA less than 50 copies per mL) with no history of treatment failure and no known substitutions associated resistance with the compound of Formula I or compound of Formula II.

In another embodiment, the present invention provides a method of maintaining HIV-1 or HIV-2 (in particular for HIV-1) RNA less than 50 copies per mL by administering to the patient a pharmaceutical composition of the invention comprising a compound of Formula I, or with an additional pharmaceutically acceptable salt thereof; and a compound of Formula II, or with an additional pharmaceutically acceptable salt thereof. In another embodiment, the pharmaceutical composition comprises a compound of Formula I, or with an additional pharmaceutically acceptable salt thereof; and a compound of Formula II, or with an additional pharmaceutically acceptable salt thereof, and one or more pharmaceutically acceptable excipients, diluents or carriers. In an additional embodiment, HIV-1 or HIV-2 (in particular for HIV-1) RNA less than 50 copies per mL is maintained at 48 weeks after switching treatment regimens from a three or more antiretroviral regimen to treatment regimen consisting of a compound of Formula I, or with an additional pharmaceutically acceptable salt thereof, and a compound of Formula II, or with an additional pharmaceutically acceptable salt thereof, and at least one excipient, diluent or carrier.

In another embodiment, the treatment regimen comprising two antiretroviral agents is additionally supplemented with an additional 20 mg. to 30 mg. of a compound of Formula II, or with an additional pharmaceutically acceptable salt thereof, and rifabutin. Another embodiment comprises a method wherein the additional 20 mg. to 30 mg. of a compound of Formula II, or with an additional pharmaceutically acceptable salt thereof, is taken with food, such as a food that comprises at least a moderate or higher fat content. Another embodiment comprises a method wherein the additional 20 mg. to 30 mg. of a compound of Formula II, or with an additional pharmaceutically salt thereof, is administered for the duration of the rifabutin coadministration.

In yet another embodiment, the treatment regimen comprising two retroviral agents is supplemented with an additional 25 mg. of a compound of Formula II, or with an additional pharmaceutically acceptable salt thereof, and rifabutin. Another embodiment comprises a method wherein the additional 25 mg. of a compound of Formula II, or with an additional pharmaceutically acceptable salt thereof, is taken with food, such as a food that comprises at least a moderate or higher fat content. In yet another embodiment comprises a method wherein the additional 25 mg. of a compound of Formula II, or with an additional pharmaceutically acceptable salt thereof, is administered for the duration of the rifabutin coadministration.

In another embodiment, the patient's mean bone density increases after switching from an antiretroviral treatment regimen comprising at least three antiretroviral agents to a treatment regimen comprising only two antiretroviral agents. In another embodiment, wherein the patient was previously treated with tenofovir or tenofovir prodrug, such as tenofovir disoproxil fumarate (TDF) or TAF (including hemi-fumarate and mono-fumarate). In another embodiment, the patient's mean bone mineral density increases about 1.5% over 48 weeks. As is understood in the art, bone density can be measured as total hip and/or lumbar spine. In some aspects, a density increase of about 1.5% includes any increase in bone density of greater than about 1.0%, including but not limited to about 1.0%, 1.1%, 1.2%, 1.3%, 1.45, 1.5%, 1.6%, 17%, 1.8% 1.9%. and 2.0%. In another embodiment, the patient's total hip bone mineral density increases about 1.3% over 48 weeks. In another embodiment, the patient's total lumbar spine bone mineral density increases about 1.5% over 48 weeks. A further embodiment of the invention wherein the patient was switched from an ART regimen containing TDF to a regimen containing a compound of Formula I, or with an additional pharmaceutically acceptable salt, and a compound of Formula II, or with an additional pharmaceutically acceptable salt, increased mean bone mineral density from baseline to week 48 (1.34% total hip and 1.46% lumbar spine) compared with those who continued on treatment with a TDF-containing antiretroviral regimen (0.05% total hip and 0.15% lumbar spine) in a dual-energy X-ray absoroptiometry (DEXA) study.

In one embodiment, a method of treating a patient infected with a human immunodeficiency virus using a two-drug regimen comprising of an integrase inhibitor and a non-nucleoside reverse transcriptase inhibitor where the patient's current antiretroviral regimen comprises three or more antiviral agents. As is understood in the art an antiretroviral regimen comprising three or more antiviral agents may comprise three, four, five six, seven or more antiviral agents. In another embodiment, wherein the integrase inhibitor is a compound of Formula I:

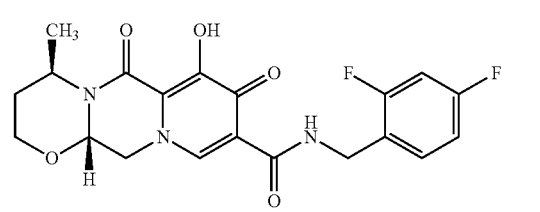

or with an additional pharmaceutically acceptable salt thereof. In another embodiment, wherein the non-nucleoside reverse transcriptase inhibitor is a compound of Formula II:

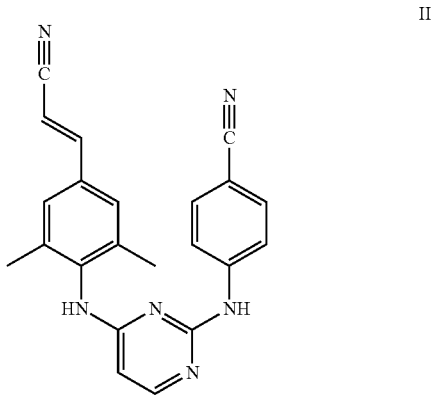 [SMILES: Cc1cc(/C=C/C#N)cc(C)c1Nc1ccnc(Nc2ccc(C#N)cc2)n1]

or with an additional pharmaceutically acceptable salt thereof.

In another embodiment, wherein the patient's current antiretroviral regimen comprises two nucleoside reverse transcriptase inhibitors (NRTIs) plus either an INSTI, an NNRTI, or a protease inhibitor (PI). In another embodiment, the patient's current antiretroviral regimen comprises an integrase inhibitor, such as bictegravir, or with an additional pharmaceutically acceptable salt thereof. In another embodiment, the patient's current antiretroviral regimen comprises at least three nucleoside reverse transcriptase inhibitors (NRTIs).

In one embodiment the present invention provides combinations of only two antiviral agents, those being a compound of Formula I, or a pharmaceutically acceptable salt thereof, and a compound of Formula II, or a pharmaceutically acceptable salt thereof, for use in treating HIV-1 or HIV-2 (in particular for HIV-1) in a virologically suppressed patient in need thereof comprising switching the patient from an antiretroviral treatment regimen comprising at least three antiretroviral agents to a treatment regimen comprising only two antiretroviral agents.

In one embodiment, kits comprising a compound of Formula I, or with an additional pharmaceutically acceptable salt thereof; and a compound of Formula II, or with an additional pharmaceutically acceptable salt thereof; and instructions for their coadministration are provided.

In a further embodiment, kits comprising a compound of Formula I, or with an additional pharmaceutically acceptable salt thereof; and a compound of Formula II, or with an additional pharmaceutically acceptable salt thereof, in oral dosage forms are provided. In one embodiment, the above-described compositions, kits or combinations for use in medical therapy are provided. In another embodiment, the above-described compositions kits or combinations for use in any of the above-described methods are provided.

The composition according to the present invention may be used as medicament or be used in making a medicament. It may be supplied in packs or kits.

Another embodiment provides a method for preventing an HIV infection or AIDS, comprising administering to a human a therapeutically effective amount of a compound of Formula I, or with an additional pharmaceutically acceptable salt thereof, and a therapeutically effective amount of a compound of Formula II, or with an additional pharmaceutically acceptable salt thereof, to a patient who is at risk of acquiring HIV infection. For example, methods may be prophylactic for an intravenous drug abuser, a person who contacts or has a likelihood of contacting bodily fluid from an HIV-infected individual, or a person who engages or may engage in a sexual or other activity associated with a risk of acquiring an HIV infection.

An embodiment of the invention provides a therapeutically effective regimen of the invention or a therapeutically effective composition of the invention. Any embodiment of the invention that comprises or relates to a patient also comprises or relates to a human. Any composition of the invention can be administered to a human. Any regimen of the invention can be used on a human, for example to treat a human, such as a human infected with HIV.

In one embodiment of this invention, combinations are provided of only two antiviral agents, those being a compound of Formula I, or a pharmaceutically acceptable salt thereof, and a compound of Formula II, or a pharmaceutically acceptable salt thereof, for use in treating HIV-1 or HIV-2 (in particular for HIV-1) in a virologically suppressed patient in need thereof comprising switching the patient from an antiretroviral treatment regimen comprising at least three antiretroviral agents to a treatment regimen comprising only two antiretroviral agents. In some embodiments the combination further comprises at least one pharmaceutically acceptable excipient, diluent, and/or carrier. Combinations of the present invention can comprise a first antiretroviral agent being dolutegravir, and the second antiretroviral agent being rilpivirine. Uses of these combinations include treating or preventing HIV-1 or HIV-2 (in particular for HIV-1) in a virologically suppressed patient in need thereof. The disclosed methods of treatment and uses can be used in connection with the combinations.

Exemplary Tablet

As part of the invention, there is provided a multilayer tablet comprising dolutegravir or a pharmaceutically acceptable salt thereof and rilpivirine or a pharmaceutically acceptable salt thereof.

In one embodiment, the dosage form comprises 50 mg of dolutegravir free acid equivalent and 25 mg of rilpivirine free base equivalent.

In one embodiment, the dosage form comprises 52.6 mg of dolutegravir sodium and 27.5 mg of rilpivirine hydrochloride.

It was found during early development compatibility studies that the interaction between dolutegravir sodium and rilpivirine hydrochloride led to disproportionation of both compounds. Storage of compacts with dolutegravir sodium and rilpivirine hydrochloride intimately mixed under stress conditions showed high levels of formation of dolutegravir as the free acid and rilpivirine as the free base. Disproportionation was also observed when initial monolayer tablets (with both drug substances formulated into a single layer tablet) were stored under open/exposed conditions.

FIGS. 1 and 2 show the dissolution profile of dolutegravir and rilpivirine following open/exposed storage of monolayer tablets for up to 4 weeks at 40° C./75% RH. Significant disproportionation of dolutegravir sodium and rilpivirine hydrochloride into the respective free acid and free base leads to the formulation not being consistent with reported salt quantities (with lack of control over what is being administered to the patient).

In order to assess the stability of monolayer formulations of dolutegravir sodium and rilpivirine hydrochloride, six monolayer formulations (Formulation #1 to Formulation #6; Table 17) were tested for stability using XRPD (X-ray powder diffraction) and $^{19}$F SSNMR (solid state nuclear magnetic resonance) spectroscopy.

TABLE 17

Monolayer RPV/DTG formulations #1 to #6
Formulation Details of DTG/RPV Monolayer Formulations

| Ingredient | Formulation #1 Mass (mg) | Formulation #2 Mass (mg) | Formulation #3 Mass (mg) | Formulaation #4 Mass (mg) | Formulation #5 Mass (mg) | Formulaation #6 Mass (mg) |
|---|---|---|---|---|---|---|
| Intragranular Dolutegravir Component | | | | | | |
| Dolutegravir sodium[1] | 52.62 | 52.62 | 52.62 | 52.62 | 52.62 | 52.62 |
| D-Mannitol (Mannitol Pearlitol 25C) | 145.38 | 145.38 | 145.38 | 145.38 | 145.38 | 145.38 |
| Microcrystalline cellulose (Avicel PH101) | 60.00 | 60.00 | 60.00 | 60.00 | 60.00 | 60.00 |

TABLE 17-continued

Monolayer RPV/DTG formulations #1 to #6
Formulation Details of DTG/RPV Monolayer Formulations

| Ingredient | Formulation #1 Mass (mg) | Formulation #2 Mass (mg) | Formulation #3 Mass (mg) | Formulaation #4 Mass (mg) | Formulation #5 Mass (mg) | Formulaation #6 Mass (mg) |
|---|---|---|---|---|---|---|
| Povidone K29/32 (Plasdone K29/32) | 15.00 | 15.00 | 15.00 | 15.00 | 15.00 | 15.00 |
| Sodium Starch Glycolate (SSG) | 15.00 | 15.00 | 15.00 | 15.00 | 15.00 | 15.00 |
| Rilpivirine Component | | | | | | |
| Rilpivirine Hydrochloride[2] | 27.50 | 27.50 | 27.50 | 27.50 | 27.50 | 27.50 |
| Lactose Monohydrate (Pharmatose 200M) | 45.848 | 105.86 | 172.54 | 45.848 | 55.145 | 55.145 |
| Microcrystalline cellulose (Avicel PH101) | 22.00 | 40.00 | 60.00 | 22.00 | n/a | n/a |
| Sodium Starch Glycolate (Glycols) | 5.50 | 10.00 | 15.00 | 5.50 | n/a | n/a |
| Croscarmellose Sodium (Ac-Di-Sol) | n/a | n/a | n/a | n/a | 1.10 | 1.10 |
| Povidone K29/32 (Plasdone K29/32) | 5.50 | 10.00 | 15.00 | 5.50 | n/a | n/a |
| Povidone K30 | n/a | n/a | n/a | n/a | 3.25 | 3.25 |
| Polysorbate 20 (Tween 20 HP) | 0.352 | 0.64 | 0.96 | 0.352 | 0.35 | 0.35 |
| Extragranular | | | | | | |
| Microcrystalline cellulose (Avicel PH102) | n/a | n/a | n/a | 38.00 | 16.605 | 55.11 |
| Lactose Anhydrous (Pharmatose DCL21) | n/a | n/a | n/a | 146.29 | n/a | 148.55 |
| Sodium Starch Glycolate (Glycols) | 8.14 | 9.94 | 11.94 | 11.94 | 8.08 | 12.00 |
| Magnesium stearate (Ligamed-MF-2-V) | 4.07 | 4.97 | 5.97 | 5.97 | 4.04 | 6.00 |
| Total Tablet Weight (Monolayer) | 406.91 | 496.91 | 596.91 | 596.90 | 404.07 | 597.01 |
| Film Coat | | | | | | |
| Opadry II Pink, 85F24022 | 12.21 | 14.91 | 17.91 | 17.91 | 12.12 | 17.91 |
| Total Tablet Weight (Film coated) | 419.12 | 511.82 | 614.82 | 614.81 | 416.19 | 614.91 |

[1]The salt conversion factor is 1.0524 (for example 52.62 mg dolutegravir sodium corresponds to 50 mg dolutegravir free acid equivalent)
[2]The salt conversion factor is 1.1 (For example 27.5 mg rilpivirine hydrochloride corresponds to 25 mg rilpivirine free base equivalent).

Solid state $^{19}$F NMR spectra and XRPD spectra of formulations 1, 4, 5 and 6 are shown in FIGS. 5 to 12. It can clearly be seen in these spectra that after 2 or 4 weeks storage, peaks associated with the salt forms of dolutegravir and rilpivirine are no longer visible and peaks associated with free acid or free base have appeared, showing that not only has disproportionation occurred, but that the dolutegravir sodium and rilpivirine hydrochloride are no longer evident. The disproportionation is not confined to a particular monolayer formulation, but was seen in all 4 monolayer formulations tested.

A solution to the problem of disproportionation is to separate the dolutegravir sodium and rilpivirine hydrochloride by formulating as a multilayer tablet.

Therefore, in one aspect there is provided a multilayer tablet comprising dolutegravir sodium and rilpivirine hydrochloride.

In one embodiment the multilayer tablet is a bilayer tablet.

In one embodiment, the multilayer tablet is a coated tablet.

In one embodiment, the multilayer tablet is a coated bilayer tablet.

To further study the potential for disproportionation, a $^{19}$F SSNMR method was developed and validated for quantification of dolutegravir free acid in DTG/RPV Tablets. This method was used to measure dolutegravir free acid in DTG/RPV Tablets after manufacture and to perform ad-hoc assessment of tablets during primary stability studies (for information purposes only). Data presented in Tables 18 and 19 demonstrate that dolutegravir free acid is not formed during the manufacture of DTG/RPV Tablets or when stored in the proposed commercial pack during in-use stability and for up to 6 months at 40° C./75% RH, and 12 months at 30° C./75% RH.

TABLE 18

Assessment of Dolutegravir Free Acid by ¹⁹F SSNMR after Manufacture of DTG/RPV Tablets

| Tablet Batch | Purpose | Material for Test | Dolutegravir Free Acid Content (% w/w) |
|---|---|---|---|
| 1 | Process Stretch Batch | DTG/RPV Film coated tablets | ND |
| 2 | Process Stretch Batch | DTG/RPV Film coated tablets | ND |
| 3 | Process Stretch Batch | DTG/RPV Film coated tablets | ND |
| 4 | Process Stretch Batch | DTG/RPV Film coated tablets | ND |

Notes:
ND = not detected (Detection Limit = 2% w/w)

TABLE 19

Dolutegravir Free Acid by ¹⁹F SSNMR in Primary Stability Batches of DTG/RPV Tablets

| Batch | Purpose | Condition | Timepoint (months) | Dolutegravir Free Acid Content (% w/w) |
|---|---|---|---|---|
| 5 | Stability | Initial | 0 | ND |
|   |   | 30° C./75% RH | 12 | ND |
|   |   | 40° C./75% RH | 6 | ND |
|   |   | In Use Study at 30° C./75% RH | 30 days | ND |
|   |   | In Use Study at 25° C./60% RH | 30 days | ND |
| 6 | Stability | Initial | 0 | ND |
|   |   | 30° C./75% RH | 12 | ND |
|   |   | 40° C./75% RH | 6 | ND |
| 7 | Stability | Initial | 0 | ND |
|   |   | 30° C./75% RH | 12 | ND |
|   |   | 40° C./75% RH | 6 | ND |

Notes:
ND = not detected (Detection Limit = 2% w/w)

From Tables 18 and 19 it can be seen that the dolutegravir free acid is not observed at detectable levels following manufacture, on long term/accelerated storage, and during in-use studies.

In conclusion, the analytical data demonstrated that the use of bilayer tablets minimises the potential for disproportionation of dolutegravir sodium in DTG/RPV Tablets.

To further study the potential for disproportionation, an XRPD method was developed and validated for quantification of rilpivirine free base in DTG/RPV Tablets with a quantitation limit of 10% w/w. This method was used to measure rilpivirine free base in DTG/RPV Tablets after manufacture and during stability studies.

In addition, in-use studies were conducted on primary stability batches to evaluate the stability of the drug product during patient use with one tablet removed from the pack each day.

Rilpivirine free base remains below the quantitation limit following long term storage for 12 months at 25° C./60% RH and at 30° C./75% RH (primary stability batches) and 18 months at 30° C./75% RH (relative bioavailability batch), after accelerated storage at 40° C./75% RH for 6 months (primary stability batches) and during in-use studies at 25° C./60% RH for 30 days.

The rilpivirine layer in the initial bilayer formulation was smaller than the dolutegravir layer (110 mg rilpivirine versus 300 mg dolutegravir compression weights). The smaller rilpivirine layer made it more difficult to control its weight, and hence drug content, with a 15 mg deviation from the target weight corresponding to 5% for the dolutegravir layer, but 13.6% for the rilpivirine layer. If the overall target weight for the bilayer is maintained throughout, any dolutegravir layer weight deviation would hence cause a nearly 3-fold higher weight deviation for the rilpivirine layer.

The solution was to increase the size of the rilpivirine layer, which consists of a rilpivirine granule formulation and extra-granular excipients. It was decided to maintain the rilpivirine granulation unchanged and blend it with a larger proportion of additional excipients.

The process parameter acceptance ranges for the rilpivirine granulation had to be reduced in order to avoid producing elevated granule sizes, as shown in FIG. 13, since larger granules are associated with demixing of the rilpivirine layer formulation when feeding the compression machine via a vacuum transfer system. The effect of demixing is loss of homogeneity of the affected layer (separation of layer components), potentially resulting in inconsistent drug content.

From FIG. 13 it can be seen that above peak LOD (loss on drying) of 12.3% w/w, a minor change in LOD has a profound effect on mean particle size. Below peak LOD of 12.3% w/w, a minor change in LOD has a considerably lesser effect on mean particle size ("x50" or "d50"), and hence a lower risk of loss of homogeneity. During manufacture of the rilpivirine layer it is important to keep the peak LOD to below 12.3% w/w. Therefore during the fluid bed granulation processing, water spraying cannot continue beyond the point at which LOD is greater than 12.3% w/w.

To measure loss on drying, a fixed sample size of known mass is weighed before drying and at various timepoints when drying until equilibrium is reached.

Therefore in one embodiment there is provided a method of manufacture of a rilpivirine formulation wherein the peak LOD is less than 12.3% w/w.

It has been found that the use of a fixed dose combination may assist in achieving appropriate pharmacokinetic parameters and/or adequate tablet stability. Additionally, the use of a multilayer tablet as a fixed dose combination may also provide pharmacokinetic and/or stability benefits.

In one embodiment, there is provided a multilayer tablet comprising (a) dolutegravir or a pharmaceutically acceptable salt thereof, and (b) rilpivirine or a pharmaceutically acceptable salt thereof. In one embodiment, the tablet comprises a first layer comprising (a) dolutegravir or a pharmaceutically acceptable salt thereof and (b) a second layer comprising rilpivirine or a pharmaceutically acceptable salt thereof. In one embodiment, the tablet comprises (a) a first layer comprising 50 mg of dolutegravir free acid equivalent, and (b) a second layer comprising 25 mg of rilpivirine free base equivalent. In one embodiment, the tablet comprises (a) a first layer comprising 52.6 mg of dolutegravir sodium, and (b) a second layer comprising 27.5 mg of rilpivirine hydrochloride. In one embodiment, the tablet comprises (a) a first layer comprising 52.6 mg of dolutegravir sodium, and (b) a second layer comprising 27.5 mg of rilpivirine hydrochloride, wherein the first layer has a total weight of less than about 350 mg, such as 300 mg, and the second layer has a total weight of less than about 250 mg, such as 200 mg.

Unless otherwise specified, the terms "first layer", "second layer" and so forth do not specify a particular order or orientation of the multilayer tablet formulations disclosed herein. Rather, these terms are used to distinguish the sections of the composition from each other and to specify the characteristics or components of each layer or section or component. The first layer may be synthesised first or may be synthesised second. The first layer may be on the top or may be on the bottom or may encapsulate the second layer. The term "first layer" is not limiting as to order or orientation.

Tablets disclosed herein will generally have a hardness within the range 14-21 kP, and in certain specific embodiments, have a hardness of 17 kP. Hardness can typically be assessed by driving a platen to compress a tablet at a constant loading rate until it fractures, operating in accordance with USP 1217.

Tablets of the invention will typically include one or more excipients. Excipients should be compatible with the other ingredients of the formulation and physiologically innocuous to the recipient thereof. Examples of suitable excipients are well known to the person skilled in the art of tablet formulation and may be found in, inter alia, "Handbook of Pharmaceutical Excipients", $7^{th}$ Ed, 2012. As used herein the term "excipients" is intended to refer to, inter alia, basifying agents, solubilisers, glidants, fillers, binders, lubricants, surface active agents, dispersing agents and the like. The term also includes agents such as sweetening agents, flavouring agents, colouring agents, preserving agents and coating agents. Such excipients will generally be present in admixture within the tablet.

Examples of solubilisers include, but are not limited to, ionic surfactants (including both ionic and non-ionic surfactants) such as sodium lauryl sulphate, cetyltrimethylammonium bromide, polysorbates (such as polysorbate 20 or 80), poloxamers (such as poloxamer 188 or 207), and macrogols. In one embodiment, the solubiliser is polysorbate 20.

Examples of lubricants, glidants and flow aids include, but are not limited to, magnesium stearate, calcium stearate, stearic acid, hydrogenated vegetable oil, glyceryl palmitostearate, glyceryl behenate, sodium stearyl fumarate, colloidal silicon dioxide, and talc. The amount of lubricant in a tablet is generally between about 0.5-5% by weight. In one embodiment, the lubricant is sodium stearyl fumarate or magnesium stearate.

Examples of disintegrants include, but are not limited to, starches, celluloses, cross-linked PVP (crospovidone), sodium starch glycolate, croscarmellose sodium, etc. In one embodiment the disintegrant is sodium starch glycolate.

Examples of fillers (also known as bulking agents or diluents) include, but are not limited to, starches, maltodextrins, polyols (such as lactose), and celluloses. In one embodiment, the filler is selected from D-mannitol, microcrystalline cellulose, silicified microcrystalline cellulose, lactose monohydrate.

Examples of binders include, but are not limited to, cross-linked PVP, HPMC, sucrose, starches, etc. In one embodiment, the binder is a povidone. In one embodiment, the binder is selected from povidone K29/32 and povidone K30.

In one embodiment, tablets provided herein are uncoated. In one embodiment, tablets provided herein are coated (in which case they include a coating). Although uncoated tablets may be used, it is more usual in the clinical setting to provide a coated tablet, in which case a conventional non-enteric coating may be used. Film coatings are known in the art and can be composed of hydrophilic polymer materials, but are not limited to, polysaccharide materials, such as hydroxypropyl methylcellulose (HPMC), methylcellulose, hydroxyethyl cellulose (HEC), hydroxypropyl cellulose (HPC), poly(vinylalcohol-co-ethylene glycol) and other water soluble polymers. Though in one embodiment the water soluble material included in the film coating of the embodiments disclosed herein includes a single polymer material, in certain other embodiments it is formed using a mixture of more than one polymer. In one embodiment, the coating is pink. Suitable coatings include, but are not limited to, polymeric film coatings such as those comprising polyvinyl alcohol e.g. OPADRY II (which includes part-hydrolysed PV A, titanium dioxide, macrogol 3350 (PEG) and talc, with optional colouring such as iron oxide (e.g., iron oxide red or iron oxide black) or indigo carmine or iron oxide yellow or FD&C yellow #6). In one embodiment, the coating is OPADRY 11 Pink (which includes polyvinyl alcohol, titanium dioxide, macrogol/PEG, talc, yellow iron oxide and red iron oxide). The amount of coating is generally between about 2-4% of the core's weight, and in certain specific embodiments, about 3%. Unless specifically stated otherwise, where the dosage form is coated, it is to be understood that a reference to % weight of the tablet means that of the total tablet, i.e. including the coating.

To make the formulation of the invention, it is preferred to first separately prepare granulations of dolutegravir and rilpivirine, prior to formulating the final dolutegravir-rilpivirine tablets.

To make the dolutegravir granulation, the active is first mixed with one or more of the aforementioned excipients in a suitable blender to blend the materials. In one embodiment, dolutegravir (as dolutegravir sodium) is admixed with a first amount of excipients by high shear granulation. This mixture is wet granulated and wet milled and the granules are then dried and then dry milled. Thereafter, a second amount of excipients are added to the granules and further blended. The final dolutegravir granulation is collected in a suitable container. The Flow Diagram for dolutegravir manufacture is shown in FIG. 14.

In one embodiment the amount of dolutegravir utilised will be such as to deliver 50 mg of dolutegravir (as the free acid) in the final tablet formulation. In one embodiment, the amount of dolutegravir sodium is 52.6 mg of dolutegravir sodium (equivalent to 50 mg of dolutegravir as the free acid).

To prepare the rilpivirine granulation as part of the dolutegravir-rilipivirine tablets, the rilpivirine (as rilpivirine hydrochloride) is pre-mixed with a first amount of excipients. This mixture is granulated by fluid bed granulation and the granules are then dried and then dry milled. The granules are blended and thereafter a second amount of excipients are added to the granules and further blended. A glidant is added to aid lubrication and the final rilpivirine granulation is collected in a suitable container.

In one embodiment the amount of rilpivirine utilised will be such as to deliver 25 mg of rilpivirine (as the free base) in the final tablet formulation. In one embodiment, the amount of rilpivirine hydrochloride is 27.5 mg of rilpivirine hydrochloride (equivalent to 25 mg of rilpivirine as the free base)

To prepare the final tablets containing dolutegravir and rilpivirine, both the dolutegravir granulation mixture and the rilpivirine granulation mixture are compressed into bilayer tablets using equipment available in the art. In one embodiment, a bilayer tooling process is utilised to make the tablets herein. In one embodiment, the tablets of the invention are not monolayer tablets.

Bilayer tablets of the invention are prepared using automated tabletting machinery, whereby the first layer material blend is filled into the compression die, analogous to single layer tablet compression, and compressed to a low hardness.

The second layer material blend is then filled on top of the first layer and the resulting 2-layer system is compressed into the bilayer tablet.

In one embodiment, the multilayer tablet comprises 50±13 mg of dolutegravir free acid equivalent. In one embodiment, the multilayer tablet comprises 25±7 mg of rilpivirine free base equivalent.

In one embodiment, the multilayer tablet comprises 50±5 mg of dolutegravir free acid equivalent. In one embodiment, the multilayer tablet comprises 25±3 mg of rilpivirine free base equivalent.

In one embodiment, the multilayer tablet comprises 50±16 mg of dolutegravir sodium. In one embodiment, the multilayer tablet comprises 25±7 mg of rilpivirine hydrochloride.

In one embodiment, the multilayer tablet comprises 50±5 mg of dolutegravir sodium. In one embodiment, the multilayer tablet comprises 25±3 mg of rilpivirine hydrochloride.

In one embodiment, a first layer of the multilayer tablet comprises one or more excipients.

In one embodiment, the first layer of the multilayer tablet comprises:

| Ingredient | Mass (mg) |
| --- | --- |
| Dolutegravir sodium | 52.62 |
| D-mannitol | 145.38 |
| Microcrystalline cellulose | 60.00 |
| Povidone K29/32 | 15.00 |
| Sodium starch glycolate | 21.00 |
| Purified water | q.s. |
| Sodium stearyl fumarate | 6.00 |

In one embodiment, the first layer of the multilayer tablet consists of:

| Ingredient | Mass (mg) |
| --- | --- |
| Dolutegravir sodium | 52.62 |
| D-mannitol | 145.38 |
| Microcrystalline cellulose | 60.00 |
| Povidone K29/32 | 15.00 |
| Sodium starch glycolate | 21.00 |
| Purified water | q.s. |
| Sodium stearyl fumarate | 6.00 |

In one embodiment the first layer of the multilayer tablet comprises:

| Ingredient | Mass (mg) |
| --- | --- |
| Intragranular | |
| Dolutegravir sodium | 52.62 |
| D-mannitol | 145.38 |
| Microcrystalline cellulose | 60.00 |
| Povidone K29/32 | 15.00 |
| Sodium starch glycolate | 15.00 |
| Purified water | q.s. |
| Extragranular | |
| Sodium starch glycolate | 6.00 |
| Sodium stearyl fumarate | 6.00 |

In one embodiment the first layer of the multilayer tablet consists of:

| Ingredient | Mass (mg) |
| --- | --- |
| Intragranular | |
| Dolutegravir sodium | 52.62 |
| D-mannitol | 145.38 |
| Microcrystalline cellulose | 60.00 |
| Povidone K29/32 | 15.00 |
| Sodium starch glycolate | 15.00 |
| Purified water | q.s. |
| Extragranular | |
| Sodium starch glycolate | 6.00 |
| Sodium stearyl fumarate | 6.00 |

In one embodiment, the second layer of the multilayer tablet comprises one or more excipients.

In one embodiment, the second layer of the multilayer tablet comprises:

| Ingredient | Mass (mg) |
| --- | --- |
| Rilpivirine hydrochloride | 27.50 |
| Lactose monohydrate | 55.145 |
| Croscarmellose sodium | 1.10 |
| Povidone K30 | 3.25 |
| Polysorbate 20 | 0.35 |
| Purified water | q.s. |
| D-mannitol | 57.755 |
| Silicified microcrystalline cellulose | 40.00 |
| Sodium starch glycolate | 12.90 |
| Magnesium stearate | 2.00 |

In one embodiment, the second layer of the multilayer tablet consists of:

| Ingredient | Mass (mg) |
| --- | --- |
| Rilpivirine hydrochloride | 27.50 |
| Lactose monohydrate | 55.145 |
| Croscarmellose sodium | 1.10 |
| Povidone K30 | 3.25 |
| Polysorbate 20 | 0.35 |
| Purified water | q.s. |
| D-mannitol | 57.755 |
| Silicified microcrystalline cellulose | 40.00 |
| Sodium starch glycolate | 12.90 |
| Magnesium stearate | 2.00 |

In one embodiment the second layer of the multilayer tablet comprises:

| Ingredient | Mass (mg) |
| --- | --- |
| Intergranular | |
| Rilpivirine hydrochloride | 27.50 |
| Lactose monohydrate | 55.145 |
| Croscarmellose sodium | 1.10 |
| Povidone K30 | 3.25 |
| Polysorbate 20 | 0.35 |
| Purified water | q.s. |
| Extragranular | |
| D-mannitol | 57.755 |
| Silicified microcrystalline cellulose | 40.00 |
| Sodium starch glycolate | 12.90 |
| Magnesium stearate | 2.00 |

In one embodiment the second layer of the multilayer tablet consists of:

| Ingredient | Mass (mg) |
|---|---|
| Intergranular | |
| Rilpivirine hydrochloride | 27.50 |
| Lactose monohydrate | 55.145 |
| Croscarmellose sodium | 1.10 |
| Povidone K30 | 3.25 |
| Polysorbate 20 | 0.35 |
| Purified water | q.s. |
| Extragranular | |
| D-mannitol | 57.755 |
| Silicified microcrystalline cellulose | 40.00 |
| Sodium starch glycolate | 12.90 |
| Magnesium stearate | 2.00 |

In one embodiment the first layer of the multilayer tablet consists of:

| Ingredient | Mass (mg) |
|---|---|
| Dolutegravir sodium | 61.9-64.5 |
| D-mannitol | 123.6-181.7 |
| Microcrystalline cellulose | 51-75 |
| Povidone | 12.8-18.8 |
| Sodium starch glycolate | 17.9-26.3 |
| Sodium stearyl fumarate | 5.1-7.5 |

In one embodiment the second layer of the multilayer tablet consists of:

| Ingredient | Mass (mg) |
|---|---|
| Rilpivirine hydrochloride | 23.4-34.4 |
| Lactose monohydrate | 46.9-68.9 |
| Croscarmellose sodium | 0.93-1.3 |
| Povidone K30 | 2.76-4.06 |
| Polysorbate 20 | 0.30-0.44 |
| Purified water | q.s. |
| D-mannitol | 49.1-72.2 |
| Silicified microcrystalline cellulose | 34.0-50.0 |
| Sodium starch glycolate | 11.0-16.1 |
| Magnesium stearate | 1.7-2.5 |

In one embodiment of the multilayer tablet formulation, the first layer is in contact with the second layer.

In one embodiment, the first layer is produced first, followed by the second layer. That is, in one embodiment, the first layer is prepared and pressed into a first layer, followed by the second layer being prepared and being pressed with the first layer into a multilayer tablet. In one embodiment, the second layer is produced first, followed be the first layer. That is, in one embodiment, the second layer is prepared and pressed into a second layer, followed by the first layer being prepared and being pressed with the second layer into a multilayer tablet. As used herein, when describing the multilayer tablets disclosed herein, the terms "first layer" and "second layer" are not intended to indicate the method by which the tablets are produced, in particular the order in which the layers are obtained.

In one embodiment, the multilayer tablet further comprises additional layers. In one embodiment, the additional layer or layers are located between the first and second layers. In one embodiment, the additional layer or layers are located on either side of the first and/or second layer, such that they are an outside layer of the tablet and/or are disposed between the first and/or second layer and a coating layer. In some embodiments, the additional layer or layers encapsulate the first and second layers.

In one embodiment, the multilayer tablet further comprises a film coating. In one embodiment, the multilayer tablet further comprises about 1 mg to about 30 mg of a film coating. In one embodiment, the multilayer tablet further comprises about 10 mg to about 20 mg of a film coating. In one embodiment, the multilayer tablet further comprises about 15 mg of a film coating. In one embodiment the film coating comprises polyvinyl alcohol, titanium dioxide, macrogol/PEG, talc, yellow and red iron oxide.

In one embodiment, the multilayer tablet further includes a film coating. In one embodiment, the multilayer tablet further comprises about 0.2% to about 6% w/w of a film coating. In one embodiment, the multilayer tablet further comprises about 2% to about 4% w/w of a film coating. In one embodiment, the multilayer tablet further comprises about 3% w/w of a film coating.

In one embodiment, a tablet is provided comprising a first layer consisting of:

| Ingredient | % w/w in tablet |
|---|---|
| Dolutegravir sodium | 10.52 |
| D-mannitol | 29.08 |
| Microcrystalline cellulose | 12.00 |
| Povidone K29/32 | 3.00 |
| Sodium starch glycolate | 4.20 |
| Purified water | q.s. |
| Sodium stearyl fumarate | 1.20 | and a second layer consisting of:

| Ingredient | % w/w in tablet |
|---|---|
| Rilpivirine hydrochloride | 5.5 |
| Lactose monohydrate | 11.03 |
| Croscarmellose sodium | 0.22 |
| Povidone K30 | 0.65 |
| Polysorbate 20 | 0.07 |
| Purified water | q.s. |
| D-mannitol | 11.55 |
| Silicified microcrystalline cellulose | 8.00 |
| Sodium starch glycolate | 2.58 |
| Magnesium stearate | 0.40 | and optionally a film coating. In one embodiment the tablet is film coated.

In one embodiment, the layer is as any of the above embodiments but D-mannitol is partially or completely substituted by lactose. In one embodiment, the layer is as any of the above embodiments but D-mannitol is partially or completely substituted by dibasic calcium phosphate. In one embodiment, the layer is as any of the above embodiments but D-mannitol is partially or completely substituted by calcium sulfate dihydrate.

In one embodiment, the layer is as any of the above embodiments but microcrystalline cellulose is partially or completely substituted by pregelatinized starch.

In one embodiment, the layer is as any of the above embodiments but povidone is partially or completely substituted by hypromellose.

In one embodiment, the layer is as any of the above embodiments but sodium starch glycoate is partially or completely substituted by crospovidone. In one embodiment, the layer is as any of the above embodiments but sodium starch glycoate is partially or completely substituted by croscarmellose sodium.

In one embodiment, the layer is as any of the above embodiments but sodium stearyl fumarate is partially or completely substituted by one or a combination of magnesium stearate, calcium stearate, zinc stearate, stearic acid, glyceryl dibehenate, or hydrogenated vegetable oil In one embodiment, the tablet is a pink, film coated, oval, biconvex tablet.

Manufacturing Methods

Methods for producing the compositions and dosage forms (in particular tablets) disclosed herein are also provided. In some embodiments, the method comprises (a) mixing dolutegravir sodium, D-mannitol, microcrystalline cellulose, Povidone K29/32, sodium starch glycolate, purified water, and sodium stearyl fumarate to afford a dolutegravir layer mix; and (b) mixing rilpivirine hydrochloride, lactose monohydrate, croscamellose sodium, povidone K30, polysorbate 20, purified water, D-mannitol, silicified microcrystalline cellulose, sodium starch glycolate, and magnesium stearate to afford a rilpivirine layer mix; followed by (c) compressing the dolutegravir layer mix as a first layer, and (d) compressing the rilpivirine layer mix as a second layer. In one embodiment, the method comprises the steps (a) and (b) as hereinbefore described, followed by (c) compressing the rilpivirine layer mix followed by (d) compressing the dolutegravir layer mix as a second layer. In other embodiments, the method comprises the steps (a) and (b) as hereinbefore described, followed by (c) compressing the dolutegravir layer mix as one layer followed by (d) compressing the rilpivirine layer mix as a second layer. The first layer and second layer may be compressed separately and subsequently combined. However, more typically, a first layer is formed by compression and subsequently a second layer is compressed directly onto the first layer. In one embodiment, the choice of layer order in the tableting of multilayer tablets may have an impact on the properties of the tablets (e.g. the adhesion of the layers within the tablet).

In some embodiments, a tablet is provided wherein the first layer is obtainable by a method of (a) compressing the dolutegravir layer mix as a first layer, and (b) compressing the rilpivirine layer mix as a second layer. In other embodiments, a tablet is provided wherein the second layer is obtainable by a method of (a) compressing the dolutegravir layer mix as a first layer, and (b) compressing the rilpivirine layer mix as a second layer.

In one embodiment, the methods will include a step of coating the tablet cores after compression, e.g. with a film coating as described above.

In general, tableting methods are well known in the art of pharmacy. Techniques and formulations generally are found in Remington's Pharmaceutical Sciences (Mack Publishing Co., Easton, Pa.), which is hereby incorporated by reference herein in its entirety.

A tablet can be made by compression or moulding, optionally with one or more excipients. Compressed tablets may be prepared by compressing in a suitable machine the active ingredient in a free-flowing form such as a powder or granules, optionally mixed with excipients.

Pharmacokinetics $C_{max}$ is the maximum observed plasma/serum concentration of drug and is reflective of the peak systemic exposure $AUC_{(0-t)}$ is the observed exposure to drug at time t after administration circulating in the plasma/serum.

$AUC_{(0-\infty)}$ is the observed total drug exposure over time.

CV or coefficient of variation is a measure of the variability of a sample dataset expressed as a percentage of the mean. It is calculated as the ratio of the standard deviation of the sample to the mean of the sample, expressed as a percentage.

$AUC_{last}$ (also referred to $AUC_{(0-t)}$ when t is tlast) is the area under the plasma/serum concentration versus time curve from time zero to the last measurable timepoint. This values represents the total drug exposure over time.

Tables 20 and 21 summarise the pharmacokinetic parameters for rilpivirine and dolutegravir for a bilayer tablet of the invention compared to coadministration of dolutegravir and rilpivirine single dose formulations. It can be seen that the bilayer formulation displays equivalent pharmacokinetic parameters to the coadministration of rilpivirine and dolutegravir.

TABLE 20

Summary of Selected Dolutegravir Pharmacokinetic Parameters Following a High-fat Meal[a] (Part 1) or a Moderate-fat Meal[b] (Part 2) and Fasted (Part 2)

| Parameter | Geometric LS (least square) Mean | | GLS Means Ratio (90% CI) | % CVw |
|---|---|---|---|---|
| | Test | Reference | | |
| Formulation A: High Fat | A (Fed) Part 1 (N = 25) | A (Fasted) Part 2 (N = 36) | | |
| AUC(0-t) (µg · h/mL)[c] | 60.22 | 38.78 | 1.553 (1.340, 1.800) | 22.1 |
| AUC(0-∞) (µg · h/mL) | 61.67 | 39.91 | 1.545 (1.337, 1.786) | 21.7 |
| Cmax (µg/mL) | 3.429 | 2.267 | 1.513 (1.313, 1.743) | 21.5 |
| Formulation AM: High Fat | AM (Fed) Part 1 (N = 12) | AM (Fasted) Part 2 (N = 12) | | |
| AUC(0-t) (µg · h/mL)[c] | 63.68 | 33.61 | 1.895 (1.545, 2.324) | 22.1 |
| AUC(0-∞) (µg · h/mL) | 65.03 | 34.72 | 1.873 (1.533, 2.289) | 21.7 |
| Cmax (µg/mL) | 3.397 | 1.977 | 1.718 (1.411, 2.092) | 21.5 |
| Formulation AM: Moderate Fat | AM (Fed) Part 2 (N = 12) | AM (Fasted) Part 2 (N = 12) | | |
| AUC(0-t) (µg · h/mL)[c] | 62.94 | 33.56 | 1.875 (1.547, 2.274) | 27.9 |
| AUC(0-∞) (µg · h/mL) | 64.62 | 34.64 | 1.865 (1.542, 2.257) | 27.6 |
| Cmax (µg/mL) | 3.395 | 1.941 | 1.749 (1.403, 2.181) | 32.1 |

[a]High-fat breakfast contained ~900 total calories: 150 calories from protein, 250 calories from carbohydrate, and 500 calories from fat.
[b]Moderate-fat meal contained ~625 total calories: 125 calories from protein, 300 calories from carbohydrate, and 200 calories from fat.
ct = tlast. Median tlast ~72 h for all treatments.
Treatment A: DTG 50 mg tablet (clinical image) plus a single RPV 25 mg tablet (EDURANT).
Treatment AM: DTG/RPV 50 mg/25 mg FDC tablet.

TABLE 21

Summary of Selected Rilpivirine Pharmacokinetic Parameters Following a High-fat Meal[a] (Part 1) or a Moderate-fat Meal[b] (Part 2) and Fasted (Part 2)

| Parameter | Geometric LS (least square) Mean | | GLS Means Ratio | |
|---|---|---|---|---|
| | Test | Reference | (90% CI) | % CVw |
| Formulation A: High Fat | A (Fed) Part 1 (N = 25) | A (Fasted) Part 2 (N = 36) | | |
| AUC(0-t) (ng · h/mL)[c] | 3090 | 1902 | 1.625 (1.364, 1.934) | 21.7 |
| AUC(0-∞) (ng · h/mL)[d,e] | 3643 | 2168 | 1.680 (1.400, 2.016) | 20.7 |
| Cmax (ng/mL) | 101.3 | 53.12 | 1.907 (1.541, 2.360) | 31.4 |
| Formulation AM: High Fat | AM (Fed) Part 1 (N = 12) | AM (Fasted) Part 2 (N = 12) | | |
| AUC(0-t) (ng · h/mL)[c] | 3542 | 1911 | 1.853 (1.480, 2.321) | 21.7 |
| AUC(0-∞) (ng · h/mL)[d,e] | 3886 | 2265 | 1.716 (1.360, 2.164) | 20.7 |
| Cmax (ng/mL) | 114.2 | 52.66 | 2.168 (1.619, 2.902) | 31.4 |
| Formulation AM: Moderate Fat | AM (Fed) Part 2 (N = 12) | AM (Fasted) Part 2 (N = 12) | | |
| AUC(0-t) (ng · h/mL)[c] | 2907 | 1843 | 1.577 (1.241, 2.004) | 35.1 |
| AUC(0-∞) (ng · h/mL)[e] | 3508 | 2236 | 1.569 (1.244, 1.980) | 33.8 |
| Cmax (ng/mL) | 95.08 | 50.29 | 1.891 (1.339, 2.669) | 52.1 |

[a]High-fat breakfast contained ~900 total calories: 150 calories from protein, 250 calories from carbohydrate, and 500 calories from fat.
[b]Moderate-fat meal contained ~625 total calories: 125 calories from protein, 300 calories from carbohydrate, and 200 calories from fat.
[c]t = tlast. Median tlast ~168 h for all treatments.
[d]4 subjects (2 fed, 2 fasted) were excluded from the statistical analysis of AUC(0-∞) because >40% of AUC(0-∞) extrapolated and λz time duration <2x calculated t½.
[e]Interpret with caution as large number of profiles (~20% across study) have AUC(0-∞) with % extrapolated >20% or poorly estimated t½.
Treatment A: DTG 50 mg tablet (clinical image) plus a single RPV 25 mg tablet (EDURANT).
Treatment AM: DTG/RPV 50 mg/25 mg FDC tablet.

$C_{max}$, $AUC_{0-t}$, $AUC_{0-\infty}$ and $AUC_{last}$ are standard pharmacokinetic parameters that can be estimated manually or by using modelling software well known in the art, such as the Pharsight WinNonlin package using a non-compartmental model. The general basis for calculation of these quantities is well-known (e.g. see Rowland & Tozer (2010) *Clinical Pharmacokinetics and Pharmacodynamics: Concepts and Applications* ISBN 978-0781750097, or Jambhekar & Breen (2012) *Basic Pharmacokinetics* ISBN 978-0853699804). Typically the parameters will be assessed as the average (e.g. geometric or arithmetic mean) from within a group of at least 12 (and normally between 24 and 36) healthy human adults. Parameters should be measured in accordance with standards and practices which would be acceptable to a pharmaceutical regulatory agency such as FDA, EMA, MHLW, or WHO. The values may be based on measurements taken at appropriate intervals following the time of tablet ingestion, such as every hour, or at increasingly sparse sampling intervals, such as 1, 3, 5, 7, 9, 11, 13, 15, 20, and 24 hours after ingestion. They can be assessed either following a single-dose of drug or at steady state, but will typically be assessed following a single-dose.

It is well known in the bioavailability and bioequivalence arts how to determine whether any particular tablet meets regulatory requirements for equivalent bioavailability and pharmacokinetic bioequivalence e.g. see: Niazi (2014) *Handbook of Bioequivalence Testing*, 2nd Edition, ISBN 978-1482226379; *Guidance for Industry Bioavailability and Bioequivalence Studies for Orally Administered Drug Products—General Considerations* FDA March 2003; and *Guideline On The Investigation Of Bioequivalence*, EMEA 2010 CPMP/EWP/QWP/1401/98 Rev. 11 Corr \*\*. To ensure statistical power a study to measure the $C_{max}$ and $AUC_{last}$ values will be performed in multiple subjects e.g. in a group of at least 12 (and normally between 24 and 36) healthy human adults.

Because determining the $C_{max}$ and $AUC_{last}$ values is necessarily destructive these parameters will not be determined directly for the dosage form (in particular the tablet) in question, but rather for a dosage form made by the same manufacturing process with the same components. Thus a batch of a dosage form (e.g. tablets) can be made by a particular process, and the 90% confidence interval of $C_{max}$ and $AUC_{last}$ will be assessed on a sample of those tablets. If these values meet the 80-125% requirement noted above then tablets made by the manufacturing process in question are tablets of the present invention.

In one embodiment, there is provided a pharmaceutical composition comprising dolutegravir or a pharmaceutically acceptable salt thereof and rilpivirine or a pharmaceutically acceptable salt thereof wherein the composition provides a $C_{max}$ of dolutegravir in fed patients on a standardized moderate fat breakfast of from about 2800 ng/mL to about 4200 ng/mL. In one embodiment, there is provided a pharmaceutical composition comprising dolutegravir or a pharmaceutically acceptable salt thereof and rilpivirine or a pharmaceutically acceptable salt thereof wherein the composition provides a $C_{max}$ of dolutegravir in fed patients on a standardized moderate fat breakfast of from about 2900 ng/mL to about 4000 ng/mL. In one embodiment, there is provided a pharmaceutical composition comprising dolutegravir or a pharmaceutically acceptable salt thereof and rilpivirine or a pharmaceutically acceptable salt thereof wherein the composition provides a $C_{max}$ of dolutegravir in fed patients on a standardized moderate fat breakfast of from about 3000 ng/mL to about 3900 ng/mL. In one embodiment, there is provided a pharmaceutical composition comprising dolutegravir or a pharmaceutically acceptable salt thereof and rilpivirine or a pharmaceutically acceptable salt thereof wherein the composition provides a $C_{max}$ of dolutegravir in fed patients on a standardized moderate fat breakfast of from about 3500 ng/mL to about 3900 ng/mL. In one embodiment, there is provided a pharmaceutical composition comprising dolutegravir or a pharmaceutically acceptable salt thereof and rilpivirine or a pharmaceutically acceptable salt thereof wherein the composition provides a $C_{max}$ of dolutegravir in fed patients on a standardized moderate fat breakfast of from about 3600 ng/mL to about 3800 ng/mL.

In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-t}$ of dolutegravir in fed patients on a standardized moderate fat breakfast of from about 56 h·µg/mL to about 72 h·µg/mL. In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-t}$ of dolutegravir in fed patients on a standardized moderate fat breakfast of from about 53 h. µg/mL to about 75 h·µg/mL. In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-t}$ of dolutegravir in fed patients on a standardized moderate fat breakfast of from about 51 h. µg/mL to about 77 h·µg/mL. In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-t}$ of dolutegravir in fed patients on a standardized moderate fat breakfast of from about 61 h. µg/mL to about 72 h. µg/mL. In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-t}$ of dolutegravir in fed patients on a standardized moderate fat breakfast of from about 62 h. µg/mL to about 71 h. µg/mL. In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-t}$ of dolutegravir in fed patients on a standardized moderate fat breakfast of from about 63 h. µg/mL to about 70 h. µg/mL.

In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-\infty}$ of dolutegravir in fed patients on a standardised moderate fat diet of from about 51 h·µg/mL to about 80 h·µg/mL.

In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-\infty}$ of dolutegravir in fed patients on a standardised moderate fat diet of from about 54 h·µg/mL to about 77 h·µg/mL. In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-\infty}$ of dolutegravir in fed patients on a standardised moderate fat diet of from about 57 h·µg/mL to about 74 h·µg/mL. In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-\infty}$ of dolutegravir in fed patients on a standardised moderate fat diet of from about 61 h·µg/mL to about 72 h·µg/mL. In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-\infty}$ of dolutegravir in fed patients on a standardised moderate fat diet of from about 63 h·µg/mL to about 72 h·µg/mL. In one embodiment, there is provided a pharmaceutical composition comprising dolutegravir or a pharmaceutically acceptable salt thereof and rilpivirine or a pharmaceutically acceptable salt thereof wherein the composition provides a $AUC_{0-\infty}$ of dolutegravir in fed patients on a standardised moderate fat diet of from about 63 h·µg/mL to about 71 h·µg/mL.

Therapeutic Methods

There is also provided a method of treatment of a patient infected with HIV comprising administration of a multilayer tablet comprising dolutegravir or a pharmaceutically acceptable salt thereof and rilpivirine or a pharmaceutically acceptable salt thereof. In one embodiment, there is provided a method of treatment of a patient infected with HIV comprising administration of a multilayer tablet comprising dolutegravir sodium and rilpivirine hydrochloride. In one embodiment, there is provided a method of treatment of a patient infected with HIV comprising administration of a multilayer tablet comprising (a) 50 mg of dolutegravir free acid equivalent and (b) 25 mg of rilpivirine free base equivalent, wherein (a) and (b) are present within separate layers in the multilayer tablet. In one embodiment, there is provided a method of treatment of a patient infected with HIV comprising administration of a multilayer tablet comprising (a) 52.6 mg of dolutegravir sodium and (b) 27.5 mg of rilpivirine hydrochloride, wherein (a) and (b) are present within separate layers in the multilayer tablet.

In one embodiment there is provided a method of treatment of a patient infected with HIV comprising administration of a bilayer tablet comprising dolutegravir or a pharmaceutically acceptable salt thereof and rilpivirine or a pharmaceutically acceptable salt thereof.

There is also provided a multilayer tablet comprising dolutegravir or a pharmaceutically acceptable salt thereof and rilpivirine or a pharmaceutically acceptable salt thereof for use in the treatment of HIV infection. In one embodiment there is provided a bilayer tablet comprising dolutegravir or a pharmaceutically acceptable salt thereof and rilpivirine or a pharmaceutically acceptable salt thereof for use in the treatment of HIV infection.

Accordingly, methods for treating a patient infected with HIV are provided, comprising administering a multilayer tablet as disclosed herein to the patient. Similarly, a multilayer tablet as disclosed herein is provided for use in the treatment of HIV infection. Also provided is the use of dolutegravir or a pharmaceutically acceptable salt thereof, and rilpivirine or a pharmaceutically acceptable salt thereof, in the manufacture of a multilayer tablet disclosed herein for treatment of HIV infection.

In one embodiment, the multilayer tablets disclosed herein are used for pre-exposure prophylaxis (PrEP) to reduce the risk of sexually acquired HIV-1. Accordingly, methods for preventing infection in a patient at risk of infection with HIV-1 are provided, comprising administering a multilayer tablet as disclosed herein to the patient. Similarly, a multilayer tablet as disclosed herein is provided for use in preventing HIV infection in a patient at risk of infection with HIV-1. The invention also provides the use of dolutegravir or a pharmaceutically acceptable salt thereof, and rilpivirine or a pharmaceutically acceptable salt thereof, in the manufacture of a multilayer tablet disclosed herein for prevention of HIV-1 infection in a patient at risk of infection.

The methods herein disclosed involve administering a multilayer tablet to the patient, typically a human, and will generally involve repeated administrations, typically once daily. The treatment may be prophylactic or therapeutic treatment.

In one embodiment the multilayer tablet is taken orally once daily with a meal.

EXAMPLES

The following examples illustrate various non-limiting aspects of this invention.

Example 1

Rilpivirine is primarily metabolized by CYP3A, and drugs that induce or inhibit CYP3A may thus affect the clearance of rilpivirine. Co-administration of a composition of the invention and drugs that induce CYP3A may result in decreased plasma concentrations of rilpivirine and loss of virologic response and possible resistance to rilpivirine or to the class of NNRTIs. Co-administration of a composition of the invention and drugs that inhibit CYP3A may result in increased plasma concentrations of rilpivirine. Co-administration of a composition of the invention with drugs that increase gastric pH may result in decreased plasma concentrations of rilpivirine and loss of virologic response and possible resistance to rilpivirine or to the class of NNRTIs. Rilpivirine 25 mg. once daily is not likely to have a clinically relevant effect on the exposure of medicinal products metabolized by CYP enzymes.

Dolutegravir is metabolized by UGT1A1 with some contribution from CYP3A. Dolutegravir is also a substrate of UGT1A3, UGT1A9, BCRP, and P-gp in vitro. Co-administration of a composition of the invention with drugs that induce those enzymes and transporters may result in a decreased plasma concentration of dolutegravir and reduce the therapeutic effect of dolutegravir. Co-administration of a composition of the invention with drugs that inhibit those enzymes and transporters may result in increased plasma concentrations of dolutegravir.

Information regarding potential drug-drug interactions with dolutegravir, rilpivirine or a composition of the invention are provided in Tables 1-5. To use this composition of the invention, certain information is provided for reference or to indicate drug-drug interactions to be avoided. A further embodiment of the invention is a regimen of the invention wherein a composition of the invention comprises a compound of Formula I, or with an additional pharmaceutically acceptable form thereof, that is used at a higher or lower dose or is administered more or less frequently when one or more of the compounds in Table 1 or Table 2 is administered to a patient as compared to when none are administered to a patient.

A further embodiment of the invention is a regimen of the invention wherein a composition of the invention comprises rilpivirine, or with an additional pharmaceutically acceptable form thereof, that is used at a higher or lower dose or is administered more or less frequently when one or more of the compounds in Tables 1-5 is administered to a patient as compared to when none are administered to a patient.

Dolutegravir is primarily metabolized via UGT1A1 with some contribution from CYP3A. After a single oral dose of [14C] dolutegravir, 53% of the total oral dose is excreted unchanged in the feces. Thirty-one percent of the total oral dose is excreted in the urine, represented by an ether glucuronide of dolutegravir (18.9% of total dose), a metabolite formed by oxidation at the benzylic carbon (3.0% of total dose), and its hydrolytic N-dealkylation product (3.6% of total dose). Renal elimination of unchanged drug was less than 1% of the dose. Dolutegravir has a terminal half-life of approximately 14 hours and an apparent clearance (CL/F) of 1.0 L per hour based on population pharmacokinetic analyses.

The pharmacokinetic properties of dolutegravir have been evaluated in healthy adult subjects and HIV 1-infected adult subjects. Exposure to dolutegravir was generally similar between healthy subjects and HIV 1-infected subjects.

In vitro experiments indicate that rilpivirine primarily undergoes oxidative metabolism mediated by the cytochrome P450 CYP3A system. The terminal elimination half-life of rilpivirine is approximately 50 hours. After single dose oral administration of [14C] rilpivirine, on average 85% and 6.1% of the radioactivity could be retrieved in feces and urine, respectively. In feces, unchanged rilpivirine accounted for on average 25% of the administered dose. Only trace amounts of unchanged rilpivirine (<1% of dose) were detected in urine. The pharmacokinetic properties of rilpivirine have been evaluated in adult healthy subjects and in adult antiretroviral treatment-naïve HIV-1-infected subjects. Exposure to rilpivirine was generally lower in HIV-1 infected subjects than in healthy subjects.

A further embodiment provides discontinuing the use of a composition of the invention where a patient develops a severe skin or hypersensitivity reaction including, but not limited to, severe rash or rash accompanied by fever malaise, fatigue, muscle or joint aches, blisters or peeling of the skin, mucosal involvement [oral blisters or lesions], conjunctivitis, facial edema, hepatitis, eosinophilia, angioedema, difficulty breathing).

Established and Other Potentially Significant Drug Interactions

Information regarding potential drug interactions with dolutegravir and rilpivirine are provided in Tables 1-5. These recommendations are based on either drug interaction trials of individual components or predicted interactions due to the expected magnitude of interaction and potential for serious adverse events or loss of efficacy.

TABLE 1

Established and Other Potentially Significant Drug Interactions: Alterations in Dose or Regimen May Be Recommended Based on Drug Interaction Trials or Predicted Interactions[a]

| Concomitant Drug Class: Drug Name | Effect on Concentration | Clinical Comment |
|---|---|---|
| Antiarrhythmic: Dofetilide | ↑Dofetilide | Coadministration is contraindicated with JULUCA[b]. |
| Anticonvulsants: Carbamazepine Oxcarbazepine Phenobarbital Phenytoin | ↓Rilpivirine | Coadministration is contraindicated with JULUCA. |
| Antimycobacterials: Rifampin Rifapentine | ↓Rilpivirine | Coadministration is contraindicated with JULUCA. |
| Glucocorticoid (systemic): Dexamethasone (more than a single-dose treatment) | ↓Rilpivirine | Coadministration is contraindicated with JULUCA. |
| Herbal Products: St John's wort (*Hypericum perforatum*) | ↓Rilpivirine | Coadministration is contraindicated with JULUCA. |
| Proton Pump Inhibitors: e.g., Esomeprazole Lansoprazole Omeprazole Pantoprazole Rabeprazole | ↓Rilpivirine | Coadministration is contraindicated with JULUCA. |

TABLE 1-continued

Established and Other Potentially Significant Drug Interactions: Alterations in Dose or Regimen May Be Recommended Based on Drug Interaction Trials or Predicted Interactions[a]

| Concomitant Drug Class: Drug Name | Effect on Concentration | Clinical Comment |
|---|---|---|
| Macrolide or ketolide antibiotics: Clarithromycin Erythromycin Telithromycin | ↔Dolutegravir ↑Rilpivirine | Where possible, consider alternatives, such as azithromycin. |
| Antacids (e.g., aluminum or magnesium hydroxide, calcium carbonate) | ↓Rilpivirine | Administer JULUCA 4 hours before or 6 hours after taking antacids. |
| Medications containing polyvalent cations (e.g., Mg or Al): Cation-containing products[b] or laxatives Sucralfate Buffered medications | ↓Dolutegravir | Administer JULUCA 4 hours before or 6 hours after taking products containing polyvalent cations. |
| Oral calcium and iron supplements, including multivitamins containing calcium or iron[b] (non-antacid) | ↓Dolutegravir | Administer JULUCA and supplements containing calcium or iron together with a meal or take these supplements 4 hours before or 6 hours after taking JULUCA. |
| $H_2$-Receptor Antagonists: Famotidine Cimetidine Nizatidine Ranitidine | ↔Dolutegravir ↓Rilpivirine | JULUCA should only be administered at least 4 hours before or 12 hours after taking $H_2$-receptor antagonists. |
| Antidiabetics: Metformin[b] | ↑Metformin | With concomitant use, limit the total daily dose of metformin to 1,000 mg either when starting metformin or JULUCA. When starting or stopping JULUCA, the metformin dose may require an adjustment. Monitoring of blood glucose when initiating concomitant use and after withdrawal of JULUCA is recommended. |
| Narcotic analgesics: Methadone[b] | ↔Dolutegravir ↓Methadone ↔Rilpivirine | No dose adjustments are required when starting coadministration of methadone with JULUCA. However, clinical monitoring is recommended as methadone maintenance therapy may need to be adjusted in some patients. |
| Antimycobacterials: Rifabutin[b] | ↔Dolutegravir ↔Rifabutin ↓Rilpivirine | An additional rilpivirine 25-mg tablet should be taken with JULUCA once daily with a meal when rifabutin is coadministered. |

↑ = Increase, ↓ = Decrease, ↔ = No change.
[a]This table is not all inclusive.
[b]JULUCA is trademark for tablet containing: 50 mg of dolutegravir (equivalent to 52.6 mg dolutegravir sodium) and 25 mg of rilpivirine (equivalent to 27.5 mg rilpivirine hydrochloride).

TABLE 2

Summary of Effect of Dolutegravir on the Pharmacokinetics of Coadministered Drugs

| Coadministered Drug(s) and Dose(s) | Dose of Dolutegravir | n | Geometric Mean Ratio (90% CI) of Pharmacokinetic Parameters of Coadministered Drug with/without Dolutegravir No Effect = 1.00 | | |
|---|---|---|---|---|---|
| | | | $C_{max}$ | AUC | $C_\tau$ or $C_{24}$ |
| Daclatasvir 60 mg once daily | 50 mg once daily | 12 | 1.03 (0.84 to 1.25) | 0.98 (0.83 to 1.15) | 1.06 (0.88 to 1.29) |
| Ethinyl estradiol 0.035 mg | 50 mg twice daily | 15 | 0.99 (0.91 to 1.08) | 1.03 (0.96 to 1.11) | 1.02 (0.93 to 1.11) |
| Metformin 500 mg twice daily | 50 mg once daily | 15[a] | 1.66 (1.53 to 1.81) | 1.79 (1.65 to 1.93) | — |
| Metformin 500 mg twice daily | 50 mg twice daily | 15[a] | 2.11 (1.91 to 2.33) | 2.45 (2.25 to 2.66) | — |
| Methadone 16 to 150 mg | 50 mg twice daily | 11 | 1.00 (0.94 to 1.06) | 0.98 (0.91 to 1.06) | 0.99 (0.91 to 1.07) |
| Midazolam 3 mg | 25 mg once daily | 10 | — | 0.95 (0.79 to 1.15) | — |
| Norelgestromin 0.25 mg | 50 mg twice daily | 15 | 0.89 (0.82 to 0.97) | 0.98 (0.91 to 1.04) | 0.93 (0.85 to 1.03) |

[a]The number of subjects represents the maximum number of subjects that were evaluated.

TABLE 3

Summary of Effect of Coadministered Drugs on the Pharmacokinetics of Dolutegravir

| Coadministered Drug(s) and Dose(s) | Dose of Dolutegravir | n | Geometric Mean Ratio (90% CI) of Dolutegravir Pharmacokinetic Parameters with/without Coadministered Drugs No Effect = 1.00 | | |
|---|---|---|---|---|---|
| | | | $C_{max}$ | AUC | $C_\tau$ or $C_{24}$ |
| Antacid (Maalox) simultaneous administration | 50 mg single dose | 16 | 0.28 (0.23 to 0.33) | 0.26 (0.22 to 0.32) | 0.26 (0.21 to 0.31) |

TABLE 3-continued

Summary of Effect of Coadministered Drugs
on the Pharmacokinetics of Dolutegravir

| Coadministered Drug(s) and Dose(s) | Dose of Dolutegravir | n | Geometric Mean Ratio (90% CI) of Dolutegravir Pharmacokinetic Parameters with/without Coadministered Drugs No Effect = 1.00 | | |
|---|---|---|---|---|---|
| | | | $C_{max}$ | AUC | $C_\tau$ or $C_{24}$ |
| Antacid (Maalox) 2 h after dolutegravir | 50 mg single dose | 16 | 0.82 (0.69 to 0.98) | 0.74 (0.62 to 0.90) | 0.70 (0.58 to 0.85) |
| Calcium carbonate 1,200 mg simultaneous administration (fasted) | 50 mg single dose | 12 | 0.63 (0.50 to 0.81) | 0.61 (0.47 to 0.80) | 0.61 (0.47 to 0.80) |
| Calcium carbonate 1,200 mg simultaneous administration (fed) | 50 mg single dose | 11 | 1.07 (0.83 to 1.38) | 1.09 (0.84 to 1.43) | 1.08 (0.81 to 1.42) |
| Calcium carbonate 1,200 mg 2 h after dolutegravir | 50 mg single dose | 11 | 1.00 (0.78 to 1.29) | 0.94 (0.72 to 1.23) | 0.90 (0.68 to 1.19) |
| Carbamazepine 300 mg twice daily | 50 mg once daily | 16[c] | 0.67 (0.61 to 0.73) | 0.51 (0.48 to 0.55) | 0.27 (0.24 to 0.31) |
| Daclatasvir 60 mg once daily | 50 mg once daily | 12 | 1.29 (1.07 to 1.57) | 1.33 (1.11 to 1.59) | 1.45 (1.25 to 1.68) |
| Ferrous fumarate 324 mg simultaneous administration (fasted) | 50 mg single dose | 11 | 0.43 (0.35 to 0.52) | 0.46 (0.38 to 0.56) | 0.44 (0.36 to 0.54) |
| Ferrous fumarate 324 mg simultaneous administration (fed) | 50 mg single dose | 11 | 1.03 (0.84 to 1.26) | 0.98 (0.81 to 1.20) | 1.00 (0.81 to 1.23) |
| Ferrous fumarate 324 mg 2 h after dolutegravir | 50 mg single dose | 10 | 0.99 (0.81 to 1.21) | 0.95 (0.77 to 1.15) | 0.92 (0.74 to 1.13) |
| Multivitamin (One-A-Day) simultaneous administration | 50 mg single dose | 16 | 0.65 (0.54 to 0.77) | 0.67 (0.55 to 0.81) | 0.68 (0.56 to 0.82) |
| Omeprazole 40 mg once daily | 50 mg single dose | 12 | 0.92 (0.75 to 1.11) | 0.97 (0.78 to 1.20) | 0.95 (0.75 to 1.21) |
| Prednisone 60 mg once daily with taper | 50 mg once daily | 12 | 1.06 (0.99 to 1.14) | 1.11 (1.03 to 1.20) | 1.17 (1.06 to 1.28) |
| Rifampin[a] 600 mg once daily | 50 mg twice daily | 11 | 0.57 (0.49 to 0.65) | 0.46 (0.38 to 0.55) | 0.28 (0.23 to 0.34) |
| Rifampin[b] 600 mg once daily | 50 mg twice daily | 11 | 1.18 (1.03 to 1.37) | 1.33 (1.15 to 1.53) | 1.22 (1.01 to 1.48) |
| Rifabutin 300 mg once daily | 50 mg once daily | 9 | 1.16 (0.98 to 1.37) | 0.95 (0.82 to 1.10) | 0.70 (0.57 to 0.87) |

[a]Comparison is rifampin taken with dolutegravir 50 mg twice daily compared with dolutegravir 50 mg twice daily.
[b]Comparison is rifampin taken with dolutegravir 50 mg twice daily compared with dolutegravir 50 mg once daily.
[c]The number of subjects represents the maximum number of subjects that were evaluated.

TABLE 4

Summary of Effect of Rilpivirine on the Pharmacokinetics
of Coadministered Drugs

| Coadministered Drug(s) and Dose(s) | Dose of Rilpivirine | n | Geometric Mean Ratio (90% CI) of Coadministered Drug Pharmacokinetic Parameters with/without EDURANT No Effect = 1.00 | | |
|---|---|---|---|---|---|
| | | | $C_{max}$ | AUC | $C_{min}$ |
| Acetaminophen 500 mg single dose | 150 mg once daily[a] | 16 | 0.97 (0.86 to 1.10) | 0.91 (0.86 to 0.97) | NA |
| Atorvastatin 40 mg once daily | 150 mg once daily[a] | 16 | 1.35 (1.08 to 1.68) | 1.04 (0.97 to 1.12) | 0.85 (0.69 to 1.03) |
| 2-hydroxy-atorvastatin | | | 1.58 (1.33 to 1.87) | 1.39 (1.29 to 1.50) | 1.32 (1.10 to 1.58) |
| 4-hydroxy-atorvastatin | | | 1.28 (1.15 to 1.43) | 1.23 (1.13 to 1.33) | NA |

TABLE 4-continued

Summary of Effect of Rilpivirine on the Pharmacokinetics of Coadministered Drugs

| Coadministered Drug(s) and Dose(s) | Dose of Rilpivirine | n | Geometric Mean Ratio (90% CI) of Coadministered Drug Pharmacokinetic Parameters with/without EDURANT No Effect = 1.00 | | |
|---|---|---|---|---|---|
| | | | $C_{max}$ | AUC | $C_{min}$ |
| Chlorzoxazone 500 mg single dose taken 2 hours after rilpivirine | 150 mg once daily[a] | 16 | 0.98 (0.85 to 1.13) | 1.03 (0.95 to 1.13) | NA |
| Digoxin 0.5 mg single dose | 25 mg once daily | 22 | 1.06 (0.97 to 1.17) | 0.98 (0.93 to 1.04)[c] | NA |
| Ethinylestradiol 0.035 mg once daily | 25 mg once daily | 17 | 1.17 (1.06 to 1.30) | 1.14 (1.10 to 1.19) | 1.09 (1.03 to 1.16) |
| Norethindrone 1 mg once daily | | | 0.94 (0.83 to 1.06) | 0.89 (0.84 to 0.94) | 0.99 (0.90 to 1.08) |
| Ketoconazole 400 mg once daily | 150 mg once daily[a] | 14 | 0.85 (0.80 to 0.90) | 0.76 (0.70 to 0.82) | 0.34 (0.25 to 0.46) |
| Methadone 60-100 mg once daily, individualized dose | 25 mg once daily | 13 | | | |
| R(−) methadone | | | 0.86 (0.78 to 0.95) | 0.84 (0.74 to 0.95) | 0.78 (0.67 to 0.91) |
| S(+) methadone | | | 0.87 (0.78 to 0.97) | 0.84 (0.74 to 0.96) | 0.79 (0.67 to 0.92) |
| Metformin 850 mg single dose | 25 mg once daily | 20 | 1.02 (0.95 to −1.10) | 0.97 (0.90 to 1.06)[b] | NA |
| Omeprazole 20 mg once daily | 150 mg once daily[a] | 15 | 0.86 (0.68 to 1.09) | 0.86 (0.76 to 0.97) | NA |
| Rifampin 600 mg once daily | 150 mg once daily[a] | 16 | 1.02 (0.93 to 1.12) | 0.99 (0.92 to 1.07) | NA |
| 25-desacetylrifampin | | | 1.00 (0.87 to 1.15) | 0.91 (0.77 to 1.07) | NA |
| Sildenafil 50 mg single dose | 75 mg once daily[a] | 16 | 0.93 (0.80 to 1.08) | 0.97 (0.87 to 1.08) | NA |
| N-desmethyl-sildenafil | | | 0.90 (0.80 to 1.02) | 0.92 (0.85 to 0.99)[c] | NA |
| Simeprevir 150 mg once daily | 25 mg once daily | 21 | 1.10 (0.97 to 1.26) | 1.06 (0.94 to 1.19) | 0.96 (0.83 to 1.11) |

CI = Confidence Interval; n = Maximum number of subjects with data; NA = Not available.
[a] This interaction study has been performed with a dose higher than the recommended dose for rilpivirine (25 mg once daily) assessing the maximal effect on the coadministered drug.
[b] N (maximum number of subjects with data) for $AUC_{(0-\infty)}$ = 15.
[c] $AUC_{(0-last)}$.

TABLE 5

Summary of Effect of Coadministered Drugs on the Pharmacokinetics of Rilpivirine

| Coadministered Drug(s) and Dose(s) | Dose of Rilpivirine | n | Geometric Mean Ratio (90% CI) of Rilpivirine Pharmacokinetic Parameters with/without Coadministered Drugs No Effect = 1.00 | | |
|---|---|---|---|---|---|
| | | | $C_{max}$ | AUC | $C_{min}$ |
| Acetaminophen 500 mg single dose | 150 mg once daily[a] | 16 | 1.09 (1.01 to 1.18) | 1.16 (1.10 to 1.22) | 1.26 (1.16 to 1.38) |
| Atorvastatin 40 mg once daily | 150 mg once daily[a] | 16 | 0.91 (0.79 to 1.06) | 0.90 (0.81 to 0.99) | 0.90 (0.84 to 0.96) |
| Chlorzoxazone 500 mg single dose taken 2 hours after rilpivirine | 150 mg once daily[a] | 16 | 1.17 (1.08 to 1.27) | 1.25 (1.16 to 1.35) | 1.18 (1.09 to 1.28) |
| Ethinylestradiol/ Norethindrone 0.035 mg once daily/ 1 mg once daily | 25 mg once daily | 15 | ↔[b] | ↔[b] | ↔[b] |
| Famotidine 40 mg single dose taken 12 hours before rilpivirine | 150 mg single dose[a] | 24 | 0.99 (0.84 to 1.16) | 0.91 (0.78 to 1.07) | NA |

TABLE 5-continued

Summary of Effect of Coadministered Drugs on the Pharmacokinetics of Rilpivirine

| Coadministered Drug(s) and Dose(s) | Dose of Rilpivirine | n | Geometric Mean Ratio (90% CI) of Rilpivirine Pharmacokinetic Parameters with/without Coadministered Drugs No Effect = 1.00 | | |
|---|---|---|---|---|---|
| | | | $C_{max}$ | AUC | $C_{min}$ |
| Famotidine 40 mg single dose taken 2 hours before rilpivirine | 150 mg single dose[a] | 23 | 0.15 (0.12 to 0.19) | 0.24 (0.20 to 0.28) | NA |
| Famotidine 40 mg single dose taken 4 hours after rilpivirine | 150 mg single dose[a] | 24 | 1.21 (1.06 to 1.39) | 1.13 (1.01 to 1.27) | NA |
| Ketoconazole 400 mg once daily | 150 mg once daily[b] | 15 | 1.30 (1.13 to 1.48) | 1.49 (1.31 to 1.70) | 1.76 (1.57 to 1.97) |
| Methadone 60-100 mg once daily, individualised dose | 25 mg once daily | 12 | ↔[b] | ↔[b] | ↔[b] |
| Omeprazole 20 mg once daily | 150 mg once daily[a] | 16 | 0.60 (0.48 to 0.73) | 0.60 (0.51 to 0.71) | 0.67 (0.58 to 0.78) |
| Rifabutin 300 mg once daily | 25 mg once daily | 18 | 0.69 (0.62 to 0.76) | 0.58 (0.52 to 0.65) | 0.52 (0.46 to 0.59) |
| Rifabutin 300 mg once daily | 50 mg once daily | 18 | 1.43 (1.30 to 1.56) | 1.16 (1.06 to 1.26) | 0.93 (0.85 to 1.01) (reference arm for comparison was 25-mg-once-daily rilpivirine administered alone) |
| Rifampin 600 mg once daily | 150 mg once daily[a] | 16 | 0.31 (0.27 to 0.36) | 0.20 (0.18 to 0.23) | 0.11 (0.10 to 0.13) |
| Sildenafil 50 mg single dose | 75 mg once daily[a] | 16 | 0.92 (0.85 to 0.99) | 0.98 (0.92 to 1.05) | 1.04 (0.98 to 1.09) |
| Simeprevir 150 mg once daily | 25 mg once daily | 23 | 1.04 (0.95 to 1.13) | 1.12 (1.05 to 1.19) | 1.25 (1.16 to 1.35) |

CI = Confidence Interval; n = Maximum number of subjects with data; NA = Not available; ↔ = No change.
[a]This interaction study has been performed with a dose higher than the recommended dose for rilpivirine (25 mg once daily) assessing the maximal effect on the coadministered drug.
[b]Comparison based on historic controls.

Contraindications

JULUCA is contraindicated in patients:

with previous hypersensitivity reaction to dolutegravir or rilpivirine receiving coadministered drugs in Table 1 for which elevated plasma concentrations are associated with serious and/or life-threatening events or that significantly decrease rilpivirine plasma concentrations

TABLE 6

Drugs That are Contraindicated with JULUCA

| Drug Class | Contraindicated Drugs in Class | Clinical Comment |
|---|---|---|
| Antiarrhythmic | Dofetilide | Potential for serious and/or life-threatening events due to the potential for increased dofetilide plasma concentrations. |
| Anticonvulsants | Carbamazepine Oxcarbazepine Phenobarbital Phenytoin | Potential for significant decreases in rilpivirine plasma concentrations due to CYP3A enzyme induction, which may result in loss of virologic response. |
| Antimycobacterials | Rifampin Rifapentine | |
| Glucocorticoid (systemic) | Dexamethasone (more than a single-dose treatment) | |
| Herbal Products | St John's wort (*Hypericum perforatum*) | |
| Proton Pump Inhibitors | e.g., Esomeprazole Lansoprazole Omeprazole Pantoprazole Rabeprazole | Potential for significant decreases in rilpivirine plasma concentrations due to gastric pH increase, which may result in loss of virologic response. |

Example 2

Descriptions for Examples 2-5 are included below in Table 7.

TABLE 7

Measure Descriptions

| Measure Name | Measure Description |
| --- | --- |
| Number of participants with plasma human immunodeficiency virus (HIV) 1 ribonucleic acid (RNA) < 50 copies/milliliter (c/mL) at Week 48 using snapshot algorithm | Number of participants with plasma HIV 1 RNA < 50 c/mL at Week 48 using the Food and Drug Administration (FDA) snapshot algorithm was assessed to demonstrate the non-inferior antiviral activity of switching to DTG + RPV once daily compared to continuation of CAR over 48 weeks in HIV-1 infected antiretroviral therapy (ART)-experienced participants. Virologic success or failure was determined by the last available HIV-1 RNA assessment while the participant was on-treatment within the window of the visit of interest. Plasma samples were collected for HIV-1 RNA at Week 0 (Day 1), Week 4, 8, 12, 24, 36 and 48. Treatment with DTG + RPV were declared non-inferior to CAR if the lower end of a two-sided 95% confidence interval for the difference between the two groups in response rates at Week 48 lies above −10% by Cochran-Mantel Haenszel test. The Intent-to-Treat Exposed (ITT-E) population consisted of all randomly assigned participants who received at least one dose of study drug. |
| Changes from Baseline in cluster designation (CD)4+ lymphocyte count at Weeks 24 and 48 | Blood was collected and CD4+ cell count assessment by flow cytometry was carried out at Baseline (Day 1), Week 4, 8, 12, 24, 36 and 48 to evaluate the immunological activity of DTG + RPV once daily compared to continuation of CAR. The full set of lymphocyte sub sets was not evaluated. Change from Baseline was calculated as value at indicated time point minus Baseline value. Only those participants with data available at the specified time points were analyzed (represented by n = X, X in the category titles). |
| Number of participants with maximum post-baseline emergent chemistry toxicities over 48 weeks | Blood samples were collected at Baseline (Day 1) and at Week 4, 8, 12, 24, 36 and 48 to evaluate alanine aminotransferase (ALT), albumin, alkaline phosphatase (ALP), aspartate aminotransferase (AST), total bilirubin, chloride, creatinine, glucose, potassium, phosphate, sodium, blood urea nitrogen (BUN), total carbon dioxide, lipase, creatine phosphokinase and creatinine clearance. Value obtained at Day 1 was considered as Baseline value. Change from Baseline was calculated as value at indicated time point minus Baseline value. Number of participants who experienced maximum grade toxicity post-baseline in clinical chemistry over 48 weeks was summarized. |
| Number of participants with maximum post-baseline emergent hematology toxicities over 48 weeks | Blood samples were collected at Baseline (Day 1) and at Week 4, 8, 12, 24, 36 and 48 to evaluate hemoglobin, hematocrit, basophils, eosinophils, lymphocytes, monocytes, neutrophils, mean corpuscular volume (MCV), red blood cell (RBC) count, white blood cell (WBC) count and platelet count. Change from Baseline was calculated as value at indicated time point minus Baseline value. Number of participants who experienced maximum grade toxicity post-baseline in hematology over 48 weeks was summarized. |
| Mean change from Baseline in high-sensitivity C-reactive protein (hs-CRP) at Week 48 | Blood biomarker samples were collected at Baseline (Day 1) and 48 to assess hs-CRP. Change from Baseline was calculated as value at indicated time point minus Baseline value. |
| Mean change from Baseline in cystatin C at Week 48 | Blood biomarker samples were collected at Baseline (Day 1) and Week 48 to assess cystatin C. Change from Baseline was calculated as value at indicated time point minus Baseline value. |
| Mean change from Baseline in D-Dimer at Week 48 | Blood biomarker samples were collected at Baseline (Day 1) and Week 48 to assess D-Dimer. Change from Baseline was calculated as value at indicated time point minus Baseline value. |
| Mean change from Baseline in fatty acid binding protein 2 (FABP) and soluble CD14 at Week 48 | Blood biomarker samples were collected at Baseline (Day 1) and Week 48 to assess FABP and soluble CD14. Change from Baseline was calculated as value at indicated time point minus Baseline value. Only those participants with data available at the specified time points were analyzed (represented by n = X, X in the category titles). |
| Mean change from Baseline in Soluble CD163 | Blood biomarker samples were collected at Baseline (Day 1) and Week 48 to assess soluble CD163 and oxidized LDL. Change from Baseline was calculated as value at indicated time point minus |

TABLE 7-continued

Measure Descriptions

| Measure Name | Measure Description |
|---|---|
| and oxidized low density lipoprotein (LDL) at Week 48 | Baseline value. Only those participants with data available at the specified time points were analyzed (represented by n = X, X in the category titles). |
| Mean change from Baseline in retinol binding protein (RBP), serum creatinine and glucose at Week 48 | Blood biomarker samples were collected at Baseline (Day 1) and Week 48 to assess RBP, serum creatinine and glucose. Change from Baseline was calculated as value at indicated time point minus Baseline value. Only those participants with data available at the specified time points were analyzed (represented by n = X, X in the category titles). |
| Mean change from Baseline in urine phosphate at Week 48 | Urine biomarker samples were collected to at Baseline (Day 1) and Week 48 to assess urine phosphate. Change from Baseline was calculated as value at indicated time point minus Baseline value. |
| Mean change from Baseline in beta-2-microglobulin (B2M) (blood and urine), urine RBP and 25 hydroxy-vitamin D at Week 48 | Blood biomarker samples were collected at Baseline (Day 1) and Week 48 to assess B2M and 25 hydroxy-vitamin D. Urine biomarker samples were collected to at Baseline (Day 1) and Week 48 to assess urine B2M and urine RBP. Change from Baseline was calculated as value at indicated time point minus Baseline value. Only those participants with data available at the specified time points were analyzed (represented by n = X, X in the category titles). For 25 hydroxy-vitamin D, analysis of changes from Baseline was performed on log-transformed data. Results were transformed back via exponential transformation such that treatment comparisons are assessed via odds ratios. |
| Mean change from Baseline in urine albumin/creatinine ratio and urine protein/creatinine ratio at Week 48 | Urine biomarker samples were collected at Baseline (Day 1) and Week 48 to assess urine albumin/creatinine ratio and urine protein/creatinine ratio. Change from Baseline was calculated as value at indicated time point minus Baseline value. Only those participants with data available at the specified time points were analyzed (represented by n = X, X in the category titles). |
| Mean change from Baseline in bone-specific alkaline phosphatase, procollagen 1 N-terminal propeptide, osteocalcin, Type 1 Collagen C-telopeptides and soluble vascular cell adhesion molecule (sVCAM) at Week 48 | Blood biomarker samples were collected at Baseline (Day 1) and Week 48 to assess bone-specific alkaline phosphatase, procollagen 1 N-terminal propeptide, osteocalcin, Type 1 Collagen C-telopeptides and sVCAM. Change from Baseline was calculated as value at indicated time point minus Baseline value. Only those participants with data available at the specified time points were analyzed (represented by n = X, X in the category titles). For bone-specific alkaline phosphatase, procollagen 1-N-propeptide, osteocalcin and type 1 collagen C-telopeptide, analyses of changes from Baseline were performed on log-transformed data. Results were transformed back via exponential transformation such that treatment comparisons are assessed via odds ratios. |
| Mean change from Baseline in interleukin 6 (IL-6) at Week 48 | Blood biomarker samples were collected at Baseline (Day 1) and Week 48 to assess IL-6. Change from Baseline was calculated as value at indicated time point minus Baseline value. |
| Mean change from Baseline in insulin resistance based on homeostasis model assessment of insulin resistance (HOMA-IR) at Week 48 | Blood biomarker samples were collected at Baseline (Day 1) and Week 48 to assess insulin resistance. Change from Baseline was calculated as value at indicated time point minus Baseline value. |
| Mean change from Baseline in fasting lipids at Weeks 24 and 48 | Blood samples were collected at Baseline (Day 1), Week 24 and Week 48 to assess fasting lipids which included total cholesterol, low density lipoprotein (LDL) cholesterol, high density lipoprotein (HDL) cholesterol and triglycerides. Change from Baseline was calculated as value at indicated time point minus Baseline value. Only those participants with data available at the specified time points were analyzed (represented by n = X, X in the category titles). |

TABLE 7-continued

Measure Descriptions

| Measure Name | Measure Description |
| --- | --- |
| Pre-dose concentrations of DTG and RPV at Weeks 4, 24 and 48 or withdrawal in participants switching to DTG + RPV | Two separate blood samples for DTG and RPV were collected pre-dose at Weeks 4, 24 and 48. Pre-dose concentrations of DTG and RPV at Weeks 4, 24 and 48 or withdrawal were summarized for the participants switching to DTG + RPV in the early switch phase. Pharmacokinetic (PK) Parameter Population consisted of all participants who received DTG + RPV and provided at least one evaluable estimate of predose concentration (C0). Only those participants with data available at the specified time points were analyzed (represented by n = X, X in the category titles). |
| Pre-dose concentrations of DTG and RPV at Weeks 2, 4 and 8 in the first 20 participants who switch from efavirenz (EFV) or nevirapine (NVP) to DTG + RPV | Two blood samples were collected pre-dose for DTG and RPV at Weeks 2 and 8 only for the first 20 participants who switch from EFV or NVP to DTG + RPV. One blood sample was collected pre-dose for EFV or NVP at Week 2 for the first 20 participants who switch from EFV or NVP to DTG + RPV. PK Parameter NNRTI Subset Extra Sampling Population consisted of the first approximately 20 participants in the PK Parameter NNRTI Subset population who have extra PK samples at weeks 2 and 8. Only those participants with data available at the specified time points were analyzed (represented by n = X, X in the category titles). |
| Number of participants with plasma HIV 1 RNA < 50 c/mL at Week 48 using snapshot algorithm by Baseline third agent treatment class | Number of participants with plasma HIV 1 RNA < 50 c/mL at Week 48 using the FDA snapshot algorithm was assessed by Baseline third agent class to assess the impact of Baseline third agent class on efficacy, safety and tolerability of DTG + RPV compared to continuation of CAR. Plasma samples were collected for HIV-1 RNA at Baseline (Day 1), Week 4, 8, 12, 24, 36 and 48. The analysis was done using cochran-mantel haenszel test stratified by current antiretroviral third-agent class. Only those participants with data available at the specified time points were analyzed (represented by n = X, X in the category titles). |
| Changes from Baseline in cluster designation (CD)4+ lymphocyte count at Week 48 by Baseline third agent treatment class | Blood for CD4 cell count assessment by flow cytometery was carried out at Baseline (Day 1), Week 4, 8, 12, 24, 36 and 48 to assess the impact of Baseline third agent class (INSTI, NNRTI, or PI) on efficacy, safety and tolerability of DTG + RPV compared to continuation of CAR. The full set of lymphocyte sub sets was not evaluated. Change from Baseline was calculated as value at indicated time point minus Baseline value. Only those participants with data available at the specified time points were analyzed (represented by n = X, X in the category titles). |
| Number of participants with any AE, AELD or AE with grade 1, 2, 3 or 4 toxicity over 48 weeks Baseline third agent treatment class | An AE is any untoward medical occurrence in a participant or clinical investigation participant, temporally associated with the use of a medicinal product, whether or not considered related to the medicinal product. Number of participants with any AE, AELD or AE with maximum grade toxicity experienced by any one participant by over 48 weeks by Baseline third agent class (INSTI, NNRTI, or PI) was summarized. Only those participants with data available at the specified time points were analyzed (represented by n = X, X in the category titles). |
| Number of participants with maximum post-baseline emergent chemistry toxicities over 48 weeks by Baseline third agent treatment class | Blood samples were collected at Baseline (Day 1) and at Week 4, 8, 12, 24, 36 and 48 to evaluate ALT, albumin, ALP, AST, total bilirubin, chloride, creatinine, glucose, potassium, phosphate, sodium, BUN, total carbon dioxide, lipase, creatine phosphokinase and creatinine clearance. Change from Baseline was calculated as value at indicated time point minus Baseline value. Number of participants who experienced maximum toxicity grade post-baseline in chemistry parameters over 48 weeks by Baseline third agent treatment class was summarized. Only those participants with data available at the specified time points were analyzed (represented by n = X, X in the category titles). |
| Change from Baseline in fasting lipids at Weeks 24 and 48 by Baseline third agent treatment class | Blood samples were collected at Baseline (Day 1), 24 and 48 to assess fasting lipids which included total cholesterol (CHO), LDL cholesterol, HDL cholesterol and triglycerides. Change from Baseline was calculated as value at indicated time point minus Baseline value. Only those participants with data available at the specified time points were analyzed (represented by n = X, X in the category titles). |
| Change from Baseline in fasting lipids at Weeks 24 and 48 by Baseline third agent treatment class | Blood samples were collected at Baseline (Day 1), 24 and 48 to assess fasting lipids which included total cholesterol (CHO), LDL cholesterol, HDL cholesterol and triglycerides. Change from Baseline was calculated as value at indicated time point minus Baseline value. Only those participants with data available at the specified time points were analyzed (represented by n = X, X in the category titles). |

TABLE 7-continued

Measure Descriptions

| Measure Name | Measure Description |
| --- | --- |
| Change from Baseline in pre-specified treatment symptoms using the Symptom Distress Module at Weeks 4, 24 and 48 or withdrawal from the study | The Symptom Distress Module, also called the HIV Symptom Index or Symptoms Impact Questionnaire, is a 20-item self-reported measure that addresses the presence and perceived distress linked to symptoms commonly associated with HIV or its treatment. Between and within treatment group comparisons were assessed on change from Baseline in pre-specified treatment symptoms using the Symptom Distress Module at Weeks 4, 24 and 48 or withdrawal from the study. Change from Baseline in Symptom count and symptom bother score have been summarized. The symptom bother score is based on the score for each symptom present ranging from 1 (it doesn't bother me) to 4 (it bothers me a lot). The symptom bother score ranges from 0 to 80. Last observation carried forward (LOCF) was used as primary method of analysis. Only those participants with data available at the specified time points were analyzed (represented by n = X, X in the category titles). |
| Change from Baseline treatment satisfaction using the HIV treatment satisfaction questionnaire (HIV TSQ) at Weeks 4, 24 and 48 or withdrawal from the study | The HIV TSQ is a 10-item self-reported scale that measures overall satisfaction with treatment and by specific domains e.g., convenience, flexibility. Each item is scored 0-6 where a higher score indicates the greater improvement in the past few weeks. These items are summed up to produce a treatment satisfaction total score (0 to 60) and 2 subscales: general satisfaction/clinical and lifestyle/ease subscales (0 to 30). The HIV TSQ was administered as a paper questionnaire. Between and within treatment group comparisons were assessed on change from Baseline treatment satisfaction using the HIV TSQ at Weeks 4, 24 and 48 or withdrawal from the study. Total score, lifestyle/ease score and General satisfaction/clinical sub-score (CS) have been summarized. LOCF was used as primary method of analysis. Only those participants with data available at the specified time points were analyzed (represented by n = X, X in the category titles). |

First set of participants received DTG 50 milligrams (mg)+RPV 25 mg together once daily at approximately the same time, with a meal, in an open-label fashion up to Week 52 during early switch phase. Second set of participants continued to receive their current antiretroviral regimen (two nucleoside reverse transcriptase inhibitors [NRTIs]+a third agent). A third agent included either integrase inhibitor (INI), non-nucleoside reverse transcriptase inhibitor (NNRTI), or protease inhibitor (PI). CAR was administered according to the approved labeling in an open-label fashion up to Week 52 during early switch phase.

Results are as indicated below in Table 8 and Table 9.

TABLE 8

| Measure Name | Type of Statistical Test | 95% Confidence Interval |
| --- | --- | --- |
| Number of participants with plasma human immunodeficiency virus (HIV) 1 ribonucleic acid (RNA) < 50 copies/milliliter (c/mL) at Week 48 using snapshot algorithm | Non-Inferiority | −4.3 to 3.0 |

TABLE 9

| Measure Name | Additional Info | DTG + RPV Number of Participants | DTG + RPV Mean ± Standard Deviation (if applicable) | Current antiretroviral regimen (CAR) Number of Participants | Current antiretroviral regimen (CAR) Mean ± Standard Deviation (if applicable) |
| --- | --- | --- | --- | --- | --- |
| Changes from Baseline in cluster designation (CD)4+ lymphocyte count at Weeks 24 and 48. Units: Cells per millimeter (mm)³ | Week 24 Week 48 | 247 239 | 16.2 ± 150.34 32.3 ± 149.52 | 249 245 | 47.4 ± 179.68 41.8 ± 185.53 |
| Number of participants with maximum post-baseline emergent chemistry toxicities over 48 weeks. Units: Participant Number | Grade 1 Grade 2 Grade 3 Grade 4 | 252 252 252 252 | 95 61 22 5 | 256 256 256 256 | 78 86 23 9 |
| Number of participants with maximum post-baseline emergent hematology toxicities over 48 weeks Units: Participant Number | Grade 1 Grade 2 Grade 3 Grade 4 | 252 252 252 252 | 11 3 3 0 | 256 256 256 256 | 11 2 1 1 |
| Mean change from Baseline in high-sensitivity C-reactive protein (hs-CRP) at Week 48 Units: mg/Liter (L) | N/A | 234 | 0.11 ± 5.379 | 243 | 0.15 ± 4.944 |
| Mean change from Baseline in cystatin C at Week 48 Units: mg/L | N/A | 237 | −0.00 ± 0.113 | 245 | −0.01 ± 0.106 |
| Mean change from Baseline in D-Dimer at Week 48. Units: Nanomole (nmol)/L FEU | N/A | 224 | −0.02 ± 2.651 | 238 | 0.02 ± 2.501 |
| Mean change from Baseline in fatty acid binding protein 2 (FABP) and soluble CD14 at Week 48. Units: Nanogram/milliliter | FABP Soluble CD14 | 233 234 | −2.79 ± 3.007 379.72 ± 634.053 | 242 242 | −1.93 ± 2.150 754.54 ± 656.462 |
| Mean change from Baseline in Soluble CD163 and oxidized low density lipoprotein (LDL) at Week 48. Units: Microgram (ug)/Liter | CD163 Oxidized LDL | 232 234 | 50.18 ± 188.772 9.49 ± 745.962 | 241 242 | 54.26 ± 238.900 −41.30 ± 726.014 |
| Mean change from Baseline in retinol binding protein (RBP), serum creatinine and glucose at Week 48. Units: mg/deciliter (dL) | RBP Serum creatinine Glucose | 235 238 227 | −0.13 ± 1.023 0.087 ± 0.1074 0.762 ± 13.6194 | 243 243 227 | 0.03 ± 0.974 0.011 ± 0.0876 2.492 ± 12.1674 |
| Mean change from Baseline in urine phosphate at Week 48. Units: Millimoles (mmol)/L | N/A | 218 | −1.079 ± 16.9226 | 224 | −1.511 ± 15.8515 |
| Mean change from Baseline in beta-2-microglobulin (B2M) (blood and urine), urine RBP and 25 hydroxy-vitamin D at Week 48. Units: Nanomoles (nmol)/L | B2M 25 hydroxy-vitamin D Urine B2M Urine RBP | 233 235 89 221 | −15.1452 ± 44.55903 −13.9 ± 22.76 −128.2045 ± 726.38825 −8.8395 ± 28.83977 | 241 244 96 231 | 4.5995 ± 38.90474 −8.2 ± 24.43 39.8394 ± 253.43025 −0.5851 ± 27.56405 |

TABLE 9-continued

| Measure Name | Additional Info | DTG + RPV | | Current antiretroviral regimen (CAR) | |
|---|---|---|---|---|---|
| | | Number of Participants | Mean ± Standard Deviation (if applicable) | Number of Participants | Mean ± Standard Deviation (if applicable) |
| Mean change from Baseline in urine albumin/creatinine ratio and urine protein/creatinine ratio at Week 48. Units: Grams (g)/mol | Urine albumin/creatinine | 166 | −1.19 ± 3.916 | 171 | −2.59 ± 28.878 |
| | Urine protein/creatinine | 176 | −5.63 ± 17.219 | 182 | −1.43 ± 42.832 |
| Mean change from Baseline in bone-specific alkaline phosphatase, procollagen 1 N-terminal propeptide, osteocalcin, Type 1 Collagen C-telopeptides and soluble vascular cell adhesion molecule (sVCAM) at Week 48. Units: ug/L | Bone-specific alkaline phosphatase | 234 | −2.89 ± 4.024 | 244 | 0.90 ± 4.129 |
| | Procollagen type 1 N-propeptide | 234 | −9.1 ± 20.34 | 242 | −1.4 ± 18.95 |
| | Osteocalcin | 233 | −4.40 ± 7.605 | 242 | −0.68 ± 6.579 |
| | Type I Collagen C-Telopeptides | 234 | −0.18 ± 0.307 | 241 | −0.04 ± 1.160 |
| | sVCAM | 234 | −2.21 ± 1291.994 | 243 | 89.07 ± 1239.465 |
| Mean change from Baseline in interleukin 6 (IL-6) at Week 48. Units: Nanograms (ng)/L | N/A | 233 | 0.17 ± 2.736 | 243 | −0.18 ± 2.944 |
| Mean change from Baseline in insulin resistance based on homeostasis model assessment of insulin resistance (HOMA-IR) at Week 48. Units: Scores on a scale | N/A | 229 | −0.30 ± 5.740 | 237 | 0.51 ± 3.530 |
| Mean change from Baseline in fasting lipids at Weeks 24 and 48 Units: Millimoles (mmol)/L | Total cholesterol (Week 24) | 228 | 0.076 ± 0.8398 | 223 | 0.061 ± 0.7368 |
| | Total cholesterol (Week 48) | 221 | 0.089 ± 0.8488 | 218 | 0.064 ± 0.7197 |
| | LDL cholesterol calculation (Week 24) | 224 | 0.165 ± 0.7065 | 217 | 0.103 ± 0.6503 |
| | LDL cholesterol calculation (Week 48) | 215 | 0.108 ± 0.7178 | 211 | 0.029 ± 0.6134 |
| | HDL cholesterol direct (Week 24) | 228 | −0.030 ± 0.2601 | 223 | −0.044 ± 0.2394 |
| | HDL cholesterol direct (Week 48) | 221 | 0.023 ± 0.2757 | 218 | 0.018 ± 0.2722 |
| | Triglycerides (Week 24) | 228 | −0.154 ± 0.7324 | 223 | −0.001 ± 0.7712 |
| | Triglycerides (Week 48) | 221 | −0.093 ± 0.9767 | 218 | 0.046 ± 0.8274 |
| Number of participants with plasma HIV 1 RNA < 50 c/mL at Week 48 using snapshot algorithm by Baseline third agent treatment class. Units: Participants Number | NNRTI | 131 | 124 | 134 | 131 |
| | INSTI | 46 | 45 | 48 | 46 |
| | PI | 75 | 71 | 74 | 68 |

TABLE 9-continued

| | | DTG + RPV | | Current antiretroviral regimen (CAR) | |
|---|---|---|---|---|---|
| Measure Name | Additional Info | Number of Participants | Mean ± Standard Deviation (if applicable) | Number of Participants | Mean ± Standard Deviation (if applicable) |
| Changes from Baseline in cluster designation (CD)4+ lymphocyte count at Week 48 by Baseline third agent treatment class. Units: Cells per mm^3 | NNRTI | 124 | 47.9 ± 142.90 | 130 | 25.0 ± 151.27 |
| | INSTI | 45 | 19.9 ± 148.63 | 46 | 39.9 ± 200.38 |
| | PI | 70 | 12.5 ± 160.27 | 69 | 74.7 ± 227.78 |
| Number of participants with any AE, AELD or AE with grade 1, 2, 3 or 4 toxicity over 48 weeks by Baseline third agent treatment class. Units: Participant Number | Any AE, NNRTI | 131 | 102 | 134 | 98 |
| | Any AE, INSTI | 46 | 38 | 48 | 34 |
| | Any AE, PI | 75 | 60 | 74 | 58 |
| | NNRTI, Maximum toxicity Grade 1 AE | 131 | 69 | 134 | 72 |
| | NNRTI, Maximum toxicity Grade 2 AE | 131 | 27 | 134 | 23 |
| | NNRTI, Maximum toxicity Grade 3 AE | 131 | 5 | 134 | 2 |
| | NNRTI, Maximum toxicity Grade 4 AE | 131 | 1 | 134 | 1 |
| | INSTI, Maximum toxicity Grade 1 AE | 46 | 28 | 48 | 20 |
| | INSTI, Maximum toxicity Grade 2 AE | 46 | 7 | 48 | 12 |
| | INSTI, Maximum toxicity Grade 3 AE | 46 | 2 | 48 | 2 |
| | INSTI, Maximum toxicity Grade 4 AE | 46 | 1 | 48 | 0 |
| | PI, Maximum toxicity Grade 1 AE | 75 | 31 | 74 | 30 |
| | PI, Maximum toxicity Grade 2 AE | 75 | 23 | 74 | 18 |
| | PI, Maximum toxicity Grade 3 AE | 75 | 4 | 74 | 9 |
| | PI, Maximum toxicity Grade 4 AE | 75 | 2 | 74 | 1 |
| | AELD, NNRTI | 131 | 3 | 134 | 0 |
| | AELD, INSTI | 46 | 2 | 48 | 0 |
| | AELD, PI | 75 | 4 | 74 | 2 |

TABLE 9-continued

| Measure Name | Additional Info | DTG + RPV | | Current antiretroviral regimen (CAR) | |
|---|---|---|---|---|---|
| | | Number of Participants | Mean ± Standard Deviation (if applicable) | Number of Participants | Mean ± Standard Deviation (if applicable) |
| Number of participants with maximum post-baseline emergent chemistry toxicities over 48 weeks by Baseline third agent treatment class. Units: Participant Number | NNRTI, Grades 1 | 131 | 47 | 134 | 42 |
| | NNRTI, Grades 2 | 131 | 32 | 134 | 48 |
| | NNRTI, Grades 3 | 131 | 13 | 134 | 13 |
| | NNRTI, Grades 4 | 131 | 2 | 134 | 3 |
| | INSTI, Grades 1 | 46 | 13 | 48 | 11 |
| | INSTI, Grades 2 | 46 | 19 | 48 | 15 |
| | INSTI, Grades 3 | 46 | 1 | 48 | 1 |
| | INSTI, Grades 4 | 46 | 3 | 48 | 2 |
| | PI, Grades 1 | 75 | 35 | 74 | 25 |
| | PI, Grades 2 | 75 | 10 | 74 | 23 |
| | PI, Grades 3 | 75 | 8 | 74 | 9 |
| | PI, Grades 4 | 75 | 0 | 74 | 4 |
| Change from Baseline in fasting lipids at Weeks 24 and 48 by Baseline third agent treatment class. Units: mmol/L | CHO, Week 24, Overall | 228 | 3.239 ± 18.1556 | 223 | 2.375 ± 14.8357 |
| | CHO, Week 48, Overall | 221 | 3.596 ± 18.7072 | 218 | 2.472 ± 14.7202 |
| | HDL CHO direct, Overall, Week 24 | 228 | 0.017 ± 18.7575 | 223 | −2.478 ± 16.6754 |
| | HDL CHO direct, Overall, Week 48 | 221 | 3.975 ± 21.1039 | 218 | 3.095 ± 18.8909 |
| | LDL CHO calculation, Overall, Week 24 | 224 | 11.504 ± 36.9087 | 217 | 6.196 ± 24.0104 |
| | LDL CHO calculation, Overall, Week 48 | 215 | 8.257 ± 33.0405 | 211 | 3.258 ± 22.3644 |
| | Triglycerides, Overall, Week 24 | 228 | 0.096 ± 55.6357 | 223 | 8.649 ± 48.8249 |
| | Triglycerides, Overall, Week 48 | 221 | 3.605 ± 54.4914 | 218 | 11.068 ± 54.6321 |
| Change from Baseline in pre-specified treatment symptoms using the Symptom Distress Module at Weeks 4, 24 and 48 or withdrawal from the study. Units: Scores on a scale | Symptom count, Week 4 | 212 | −1.6 ± 4.19 | 197 | 0.2 ± 4.26 |
| | Symptom count, Week 24 | 214 | −0.8 ± 5.19 | 201 | −0.2 ± 4.06 |
| | Symptom count, Week 48 | 214 | −0.4 ± 5.52 | 201 | 0.0 ± 4.49 |
| | Symptom Bother Score, Week 4 | 212 | −3.0 ± 7.25 | 197 | −0.8 ± 7.82 |
| | Symptom Bother Score, Week 24 | 214 | −1.7 ± 8.47 | 201 | −1.3 ± 8.53 |
| | Symptom Bother Score, Week 48 | 214 | −1.4 ± 8.32 | 201 | −0.7 ± 9.03 |
| Change from Baseline treatment satisfaction using the HIV treatment satisfaction questionnaire (HIV TSQ) at Weeks 4, 24 and 48 or withdrawal | Total score, Week 4 | 250 | 0.0 (−16 to 33) | 249 | 0.0 (−25 to 21) |
| | Total score, Week 24 | 252 | 1.0 (−18 to 33) | 254 | 0.0 (−28 to 28) |
| | Total score, Week 48 | 252 | 0.5 (−24 to 33) | 254 | 0.0 (−28 to 20) |

TABLE 9-continued

| Measure Name | Additional Info | DTG + RPV | | Current antiretroviral regimen (CAR) | |
|---|---|---|---|---|---|
| | | Number of Participants | Mean ± Standard Deviation (if applicable) | Number of Participants | Mean ± Standard Deviation (if applicable) |
| from the study. Units: Score on a scale Median (Full Range) | lifestyle/ease Sub-score, Week 4 | 248 | 0.0 (−7 to 15) | 249 | 0.0 (−9 to 13) |
| | lifestyle/ease Sub-score, Week 24 | 252 | 0.0 (−11 to 15) | 254 | 0.0 (−14 to 12) |
| | lifestyle/ease Sub-score, Week 48 | 252 | 0.0 (−13 to 16) | 254 | 0.0 (−14 to 13) |
| | General Satisfaction/ CS, Week 4 | 249 | 0.0 (−10 to 18) | 249 | 0.0 (−16 to 13) |
| | General Satisfaction/ CS, Week 24 | 252 | 0.0 (−7 to 18) | 254 | 0.0 (−14 to 17) |
| | General Satisfaction/ CS, Week 48 | 252 | 0.0 (−14 to 18) | 254 | 0.0 (−14 to 10) |

Example 3

First set of participants (DTG 50 mg) received DIG 50 mg+RPV 25 mg together once daily, with a meal, in an open-label fashion up to Week 52 during early switch phase.

Second set of participants (RPV 25 mg) also received DTG 50 mg+RPV 25 mg together once daily, with a meal, in an open-label fashion up to Week 52 during early switch phase.

Results are indicated below in Table 10.

TABLE 10

| Measure Name | Week Number | DTG 50 mg | | RPV 25 mg | |
|---|---|---|---|---|---|
| | | Number of Participants | Mean ± Standard Deviation | Number of Participants | Mean ± Standard Deviation |
| Pre-dose concentrations of DTG and RPV at Weeks 4, 24 and 48 or withdrawal in participants switching to DTG + RPV. Units: ug/L | Week 4 | 130 | 1581.06 ± 1146.860 | 130 | 92.046 ± 138.2880 |
| | Week 24 | 210 | 1835.68 ± 1120.539 | 210 | 87.875 ± 39.1412 |
| | Week 48 | 215 | 1915.11 ± 1304.238 | 211 | 95.405 ± 48.2978 |
| Pre-dose concentrations of DTG and RPV at Weeks 2, 4 and 8 in the first 20 participants who switch from efavirenz (EFV) or nevirapine (NVP) to DTG + RPV. Units: ug/L | Week 2 | 16 | 821.25 ± 574.607 | 15 | 65.360 ± 31.2965 |
| | Week 4 | 19 | 994.00 ± 581.201 | 19 | 67.374 ± 27.5663 |
| | Week 8 | 19 | 1561.34 ± 1096.381 | 19 | 77.416 ± 37.7129 |

Example 4

First set of Participants (DTG+RPV) received DTG 50 milligrams (mg)+RPV 25 mg together once daily at approximately the same time, with a meal, in an open-label fashion up to Week 52 during early switch phase. Second set of participants (CAR) continued to receive their current antiretroviral regimen (two nucleoside reverse transcriptase inhibitor [NRTIs]+a third agent). A third agent included either of integrase strand transfer inhibitor integrase inhibitor (INSTI), non-nucleoside reverse transcriptase inhibitor (NNRTI), or protease inhibitor (PI). CAR was administered according to the approved labeling in an open-label fashion up to Week 52 during early switch phase.

Results are as indicated below in Table 11 and 12.

TABLE 11

| Measure Name | Type of Statistical Test | 95% Confidence Interval |
|---|---|---|
| Number of participants with plasma human immunodeficiency virus (HIV) 1 ribonucleic acid (RNA) < 50 copies/milliliter (c/mL) at Week 48 using snapshot algorithm | Non-Inferiority | −3.9 to 4.2 |

TABLE 12

| Measure Name | Additional Info/Clarification | DTG + RPV | | Current antiretroviral regimen (CAR) | |
|---|---|---|---|---|---|
| | | Number of Participants | Mean ± Standard Deviation (if applicable) | Number of Participants | Mean ± Standard Deviation |
| Changes from Baseline in cluster designation (CD)4+ lymphocyte count at Weeks 24 and 48. Units: Cells per millimeter (mm)^3 | Week 24 | 251 | 42.0 ± 172.29 | 250 | 42.4 ± 164.85 |
| | Week 48 | 245 | 28.0 ± 169.35 | 241 | 18.4 ± 159.34 |
| Number of participants with maximum post-baseline emergent chemistry toxicities over 48 weeks. Units: Number of participants | Grade 1 | 261 | 92 | 255 | 80 |
| | Grade 2 | 261 | 72 | 255 | 79 |
| | Grade 3 | 261 | 11 | 255 | 16 |
| | Grade 4 | 261 | 1 | 255 | 10 |
| Number of participants with maximum post-baseline emergent hematology toxicities over 48 weeks. Units: Number of participants. | Grade 1 | 261 | 11 | 11255255 | 11 |
| | Grade 2 | 261 | 2 | 255 | 2 |
| | Grade 3 | 261 | 3 | 255 | 0 |
| | Grade 4 | 261 | 1 | 255 | 0 |
| Mean change from Baseline in high-sensitivity C-reactive protein (hs-CRP) at Week 48. Units: mg/Liter (L) | N/A | 246 | 0.10 ± 5.383 | 239 | 0.80 ± 8.527 |
| Mean change from Baseline in cystatin C at Week 48. Units: mg/L | N/A | 246 | −0.02 ± 0.110 | 237 | −0.01 ± 0.108 |
| Mean change from Baseline in D-Dimer at Week 48. Units: Nanomole (nmol)/L FEU | N/A | 239 | 0.01 ± 1.629 | 228 | −0.13 ± 2.932 |
| Mean change from Baseline in fatty acid binding protein 2 (FABP) and soluble CD14 at Week 48. Units: Nanogram/milliliter | FABP | 245 | −1.50 ± 1.278 | 236 | −0.99 ± 1.441 |
| | Soluble CD14 | 245 | 456.69 ± 731.833 | 237 | 802.26 ± 878.304 |

TABLE 12-continued

| Measure Name | Additional Info/Clarification | DTG + RPV | | Current antiretroviral regimen (CAR) | |
|---|---|---|---|---|---|
| | | Number of Participants | Mean ± Standard Deviation (if applicable) | Number of Participants | Mean ± Standard Deviation |
| Mean change from Baseline in Soluble CD163 and oxidized low density lipoprotein (LDL) at Week 48. Units: Microgram/Liter | CD163 | 245 | 65.38 ± 180.869 | 236 | 53.94 ± 215.621 |
| | Oxidized LDL | 245 | 60.87 ± 504.345 | 237 | 13.92 ± 575.305 |
| Mean change from Baseline in retinol binding protein (RBP), serum creatinine and glucose at Week 48. Units: mg/deciliter (dL) | RBP | 245 | −0.13 ± 0.825 | 237 | 0.00 ± 0.872 |
| | Serum creatinine | 245 | 0.100 ± 0.1053 | 241 | −0.003 ± 0.0847 |
| | Glucose | 242 | 0.187 ± 19.5808 | 235 | 3.220 ± 10.0987 |
| Mean change from Baseline in urine phosphate at Week 48. Units: Millimoles (mmol)/L | N/A | 235 | 1.335 ± 16.7211 | 229 | −0.798 ± 15.3771 |
| Mean change from Baseline in beta-2-microglobulin (B2M) (blood and urine), urine RBP and 25 hydroxy-vitamin D at Week 48. Units: Nanomoles (nmol)/L | B2M | 245 | −16.8800 ± 34.89330 | 238 | −4.7501 ± 43.04355 |
| | 25 hydroxy-vitamin D | 243 | −13.9 ± 25.30 | 239 | −9.2 ± 19.55 |
| | Urine B2M | 72 | −173.2820 ± 1311.24142 | 78 | 62.3209 ± 391.32049 |
| | Urine RBP | 232 | −6.8123 ± 24.09650 | 224 | −0.0631 ± 11.99886 |
| Mean change from Baseline in urine albumin/creatinine ratio and urine protein/creatinine ratio at Week 48. Units: Grams (g)/mol | Urine albumin/creatinine ratio | 178 | −0.78 ± 5.116 | 181 | −0.64 ± 9.538 |
| | Urine protein/creatinine ratio | 192 | −2.73 ± 12.683 | 193 | 1.23 ± 5.088 |
| Mean change from Baseline in bone-specific alkaline phosphatase, procollagen 1 N-terminal propeptide, osteocalcin, Type 1 Collagen C-telopeptides and soluble vascular cell adhesion molecule (sVCAM) at Week 48. Units: Microgram (ug)/L | Bone-specific alkaline phosphatase | 246 | −3.18 ± 5.678 | 236 | 0.92 ± 4.634 |
| | Procollagen type 1 N-propeptide | 245 | −5.8 ± 20.00 | 237 | 0.3 ± 19.28 |
| | Osteocalcin | 245 | −5.11 ± 7.334 | 235 | −1.14 ± 6.017 |
| | Type I Collagen C-Telopeptides | 243 | −0.15 ± 0.31 | 238 | −0.09 ± 0.344 |
| | sVCAM | 245 | −2.63 ± 571.182 | 237 | 37.42 ± 617.486 |
| Mean change from Baseline in interleukin 6 (IL-6) at Week 48. Units: Nanograms (ng)/L | N/A | 245 | −0.08 ± 2.373 | 237 | −0.07 ± 2.761 |
| Mean change from Baseline in insulin resistance based on homeostasis model assessment of insulin resistance (HOMA-IR) at Week 48. Units: Scores on a scale. | | 237 | 0.50 ± 4.780 | 224 | 0.80 ± 3.938 |

TABLE 12-continued

| Measure Name | Additional Info/Clarification | DTG + RPV Number of Participants | Mean ± Standard Deviation (if applicable) | Current antiretroviral regimen (CAR) Number of Participants | Mean ± Standard Deviation |
|---|---|---|---|---|---|
| Mean change from Baseline in fasting lipids at Weeks 24 and 48 Units: Millimoles (mmol)/L | Total cholesterol (Week 24) | 237 | −0.015 ± 0.7539 | 229 | 0.020 ± 0.5777 |
| | Total cholesterol (Week 48) | 237 | −0.079 ± 0.7926 | 230 | −0.038 ± 0.6148 |
| | LDL cholesterol calculation (Week 24) | 231 | 0.085 ± 0.5940 | 221 | 0.055 ± 0.5232 |
| | LDL cholesterol calculation (Week 48) | 229 | −0.049 ± 0.6276 | 220 | −0.076 ± 0.5280 |
| | HDL cholesterol direct (Week 24) | 237 | −0.024 ± 0.2365 | 229 | −0.051 ± 0.2258 |
| | HDL cholesterol direct (Week 48) | 237 | 0.051 ± 0.2386 | 230 | 0.049 ± 0.2489 |
| | Triglycerides (Week 24) | 237 | −0.184 ± 1.0102 | 229 | 0.040 ± 0.9164 |
| | Triglycerides (Week 48) | 237 | −0.169 ± 1.0062 | 230 | −0.021 ± 1.0156 |
| Number of participants with plasma HIV 1 RNA < 50 c/mL at Week 48 using snapshot algorithm by Baseline third agent treatment class. Units: Participants Number | NNRTI | 144 | 139 | 144 | 134 |
| | INSTI | 59 | 54 | 49 | 46 |
| | PI | 58 | 53 | 62 | 60 |
| Changes from Baseline in cluster designation (CD)4+ lymphocyte count at Week 48 by Baseline third agent treatment class. Units: Cells per mm^3 | NNRTI | 139 | 49.7 ± 166.40 | 133 | 24.3 ± 160.32 |
| | INSTI | 53 | −11.2 ± 176.56 | 46 | 10.3 ± 155.53 |
| | PI | 53 | 10.5 ± 163.67 | 61 | 12.2 ± 163.32 |
| Number of participants with any AE, AELD or AE with grade 1, 2, 3 or 4 toxicity over 48 weeks by Baseline third agent treatment class. Units: Participant Number | Any AE, NNRTI | 144 | 106 | 144 | 96 |
| | Any AE, INSTI | 59 | 47 | 49 | 36 |
| | Any AE, PI | 58 | 42 | 62 | 42 |
| | NNRTI, Maximum toxicity Grade 1 AE | 144 | 68 | 144 | 76 |
| | NNRTI, Maximum toxicity Grade 2 AE | 144 | 30 | 144 | 19 |
| | NNRTI, Maximum toxicity Grade 3 AE | 144 | 8 | 144 | 0 |
| | NNRTI, Maximum toxicity Grade 4 AE | 144 | 0 | 144 | 1 |
| | INSTI, Maximum toxicity Grade 1 AE | 59 | 27 | 49 | 20 |
| | INSTI, Maximum toxicity Grade 2 AE | 59 | 15 | 49 | 15 |
| | INSTI, Maximum toxicity Grade 3 AE | 59 | 5 | 49 | 1 |
| | INSTI, Maximum toxicity Grade 4 AE | 59 | 0 | 49 | 0 |
| | PI, Maximum toxicity Grade 1 AE | 58 | 24 | 62 | 26 |
| | PI, Maximum toxicity Grade 2 AE | 58 | 14 | 62 | 13 |

TABLE 12-continued

| Measure Name | Additional Info/Clarification | DTG + RPV | | Current antiretroviral regimen (CAR) | |
|---|---|---|---|---|---|
| | | Number of Participants | Mean ± Standard Deviation (if applicable) | Number of Participants | Mean ± Standard Deviation |
| | PI, Maximum toxicity Grade 3 AE | 58 | 3 | 62 | 3 |
| | PI, Maximum toxicity Grade 4 AE | 58 | 1 | 62 | 0 |
| | AELD, NNRTI | 144 | 5 | 144 | 1 |
| | AELD, INSTI | 59 | 4 | 49 | 0 |
| | AELD, PI | 58 | 3 | 62 | 0 |
| Number of participants with maximum post-baseline emergent chemistry toxicities over 48 weeks by Baseline third agent treatment class. Units: Participant Number | NNRTI, Grades 1 | 144 | 51 | 144 | 52 |
| | NNRTI, Grades 2 | 144 | 31 | 144 | 40 |
| | NNRTI, Grades 3 | 144 | 7 | 144 | 4 |
| | NNRTI, Grades 4 | 144 | 1 | 144 | 5 |
| | INSTI, Grades 1 | 59 | 19 | 49 | 11 |
| | INSTI, Grades 2 | 59 | 23 | 49 | 18 |
| | INSTI, Grades 3 | 59 | 3 | 49 | 3 |
| | INSTI, Grades 4 | 59 | 0 | 49 | 2 |
| | PI, Grades 1 | 58 | 22 | 62 | 17 |
| | PI, Grades 2 | 58 | 18 | 62 | 21 |
| | PI, Grades 3 | 58 | 1 | 62 | 9 |
| | PI, Grades 4 | 58 | 0 | 62 | 3 |
| Change from Baseline in fasting lipids at Weeks 24 and 48 by Baseline third agent treatment class. Units: mmol/L | CHO, Week 24, overall | 237 | 1.015 ± 15.7472 | 229 | 1.300 ± 12.2269 |
| | CHO, Week 48, overall | 237 | −0.165 ± 15.9301 | 230 | 0.194 ± 13.1071 |
| | HDL CHO direct, Overall, Week 24 | 237 | 0.557 ± 19.4929 | 229 | −2.533 ± 16.3641 |
| | HDL CHO direct, Overall, Week 48 | 237 | 6.384 ± 20.9244 | 230 | 4.723 ± 18.3253 |
| | LDL CHO calculation, Overall | 231 | 5.838 ± 22.9614 | 221 | 4.395 ± 21.6685 |
| | LDL CHO calculation, Overall, Week 48 | 229 | 1.137 ± 23.3849 | 220 | −0.598 ± 20.6931 |
| | Triglycerides, Overall, Week 24 | 237 | −0.825 ± 42.5565 | 229 | 9.379 ± 45.5529 |
| | Triglycerides, Overall, Week 48 | 237 | 1.169 ± 51.9844 | 230 | 7.183 ± 44.7044 |
| Change from Baseline in pre-specified treatment symptoms using the Symptom Distress Module at Weeks 4, 24 and 48 or withdrawal from the study. Units: Scores on a scale | Symptom count, Week 4 | 224 | −1.1 ± 4.11 | 229 | −0.8 ± 4.02 |
| | Symptom count, Week 24 | 228 | −0.7 ± 4.31 | 232 | −0.8 ± 4.64 |
| | Symptom count, Week 48 | 228 | −0.5 ± 4.33 | 231 | −0.4 ± 4.82 |
| | Symptom Bother Score, Week 4 | 224 | −2.8 ± 7.44 | 229 | −1.8 ± 7.24 |
| | Symptom Bother Score, Week 24 | 228 | −1.8 ± 8.40 | 232 | −1.7 ± 8.72 |
| | Symptom Bother Score, Week 48 | 228 | −1.5 ± 7.97 | 231 | −0.7 ± 9.30 |
| Change from Baseline treatment satisfaction using the HIV treatment satisfaction questionnaire (HIV TSQ) at Weeks 4, 24 and 48 or withdrawal from the study. Units: Score on a scale Median (Full Range) | Total score, Week 4 | 253 | 0.0 (−21 to 23) | 250 | 0.0 (−22 to 22) |
| | Total score, Week 24 | 257 | 0.0 (−27 to 23) | 252 | 0.0 (−24 to 24) |
| | Total score, Week 48 | 257 | 0.0 (−27 to 25) | 251 | 0.0 (−50 to 23) |
| | lifestyle/ease Sub-score, Week 4 | 252 | 0.0 (−11 to 15) | 249 | 0.0 (−11 to 7) |
| | lifestyle/ease Sub-score, Week 24 | 257 | 0.0 (−18 to 14) | 251 | 0.0 (−17 to 10) |
| | lifestyle/ease Sub-score, Week 48 | 257 | 0.0 (−18 to 12) | 250 | 0.0 (−21 to 11) |
| | General Satisfaction/CS, Week 4 | 253 | 0.0 (−13 to 14) | 250 | 0.0 (−17 to 15) |
| | General Satisfaction/CS, Week 24 | 257 | 0.0 (−12 to 12) | 252 | 0.0 (−15 to 15) |

TABLE 12-continued

| Measure Name | Additional Info/Clarification | DTG + RPV | | Current antiretroviral regimen (CAR) | |
|---|---|---|---|---|---|
| | | Number of Participants | Mean ± Standard Deviation (if applicable) | Number of Participants | Mean ± Standard Deviation |
| | General Satisfaction/CS, Week 48 | 257 | 0.0 (−13 to 14) | 251 | 0.0 (−29 to 14) |

Example 5

First set of participants (DTG 50 mg) received DTG 50 mg+RPV 25 mg together once daily, with a meal, in an open-label fashion up to Week 52 during early switch phase. Second set of participants (RPV 25 mg) also received DTG 50 mg+RPV 25 mg together once daily, with a meal, in an open-label fashion up to Week 52 during early switch phase.

Results are indicated below in Table 13.

TABLE 13

| Measure Name | Week Number | DTG 50 mg | | RPV 25 mg | |
|---|---|---|---|---|---|
| | | Number of Participants | Mean ± Standard Deviation | Number of Participants | Mean ± Standard Deviation |
| Pre-dose concentrations of DTG and RPV at Weeks 4, 24 and 48 or withdrawal in participants switching to DTG + RPV. Units: ug/L | Week 4 | 176 | 1578.88 ± 1170.967 | 175 | 79.504 ± 38.2305 |
| | Week 24 | 207 | 1447.23 ± 917.677 | 207 | 90.207 ± 46.3022 |
| | Week 48 | 215 | 1384.36 ± 889.829 | 215 | 91.799 ± 47.1371 |
| Pre-dose concentrations of DTG and RPV at Weeks 2, 4 and 8 in the first 20 participants who switch from efavirenz (EFV) or nevirapine (NVP) to DTG + RPV Units: ug/L | Week 2 | 19 | 834.58 ± 639.622 | 19 | 57.342 ± 29.5436 |
| | Week 4 | 22 | 1218.23 ± 842.703 | 21 | 78.338 ± 31.4825 |
| | Week 8 | 26 | 1472.50 ± 818.774 | 26 | 79.652 ± 40.7546 |

Example 6

Clinical Studies

Clinical Trials in Adult Subjects Switching to JULUCA

The efficacy of JULUCA is supported by data from 2 open-label, controlled trials [SWORD-1 (NCT02429791) and SWORD-2 (NCT02422797)] in virologically suppressed patients switching from their current antiretroviral regimen to dolutegravir plus rilpivirine.

SWORD-1 and SWORD-2 are identical 148-week, Phase 3, randomized, multicenter, parallel-group, non-inferiority trials. A total of 1,024 adult HIV-1-infected subjects who were on a stable suppressive antiretroviral regimen (containing 2 NRTIs plus either an INSTI, an NNRTI, or a PI) for at least 6 months (HIV-1 RNA less than 50 copies per mL), with no history of treatment failure and no known substitutions associated with resistance to dolutegravir or rilpivirine received treatment in the trials. Subjects were randomized 1:1 to continue their current antiretroviral regimen or be switched to dolutegravir plus rilpivirine administered once daily. The primary efficacy endpoint for the SWORD trials was the proportion of subjects with plasma HIV-1 RNA less than 50 copies per mL at Week 48.

At baseline, in the pooled analysis, the median age of subjects was 43 years (range: 21 to 79), 22% female, 20% non-white, 11% were CDC Class C (AIDS), and 11% had CD4+ cell count less than 350 cells per mm3; these characteristics were similar between treatment arms. In the pooled analysis, 54%, 26%, and 20% of subjects were receiving an NNRTI, PI, or INSTI (respectively) as their baseline third-treatment-agent class prior to randomization. This distribution was similar between treatment arms.

The primary endpoint and other outcomes (including outcomes by key baseline covariates) for the pooled SWORD-1 and SWORD-2 trials are shown in Table 14. The virologic outcome results for SWORD-1 and SWORD-2 were similar to the pooled SWORD-1 and SWORD-2 virologic outcome results.

TABLE 14

Pooled Virologic Outcomes of Randomized Treatment in SWORD-1 and SWORD-2 Trials at Week 48 in Virologically-Suppressed Subjects Who Switched to JULUCA (Snapshot Algorithm)

| | Pooled Data | |
|---|---|---|
| | Dolutegravir plus Rilpivirine (n = 513) | Current Antiretroviral Regimen (n = 511) |
| HIV-1 RNA < 50 copies/mL | 95% | 95% |
| Treatment Difference | -0.2% | |
| | (95% CI: -3.0%, 2.5%) | |
| HIV-1 RNA ≥ 50 copies/mL | <1% | 1% |
| Treatment Difference | -0.6% | |
| | (95% CI: -1.7%, 0.6%) | |
| Data in window not < 50 copies/mL | 0 | <1% |
| Discontinued for lack of efficacy | <1% | <1% |
| Discontinued for other reasons while not < 50 copies/mL | <1% | <1% |
| Change in ART | 0 | <1% |
| No virologic data at Week 48 window | 5% | 4% |
| Discontinued due to adverse event or death | 3% | <1% |
| Discontinued for other reasons[a] | 1% | 3% |
| Missing data during window but on study | 0 | <1% |

TABLE 14-continued

Pooled Virologic Outcomes of Randomized Treatment in SWORD-1 and SWORD-2 Trials at Week 48 in Virologically-Suppressed Subjects Who Switched to JULUCA (Snapshot Algorithm)

| | Pooled Data | |
|---|---|---|
| | Dolutegravir plus Rilpivirine (n = 513) | Current Antiretroviral Regimen (n = 511) |
| Proportion (%) of Subjects with HIV-1 RNA < 50 copies/mL by Baseline Category | | |
| Baseline CD4+ (cells/mm³) | | |
| <350 | 88% (n = 58) | 88% (n = 52) |
| ≥350 | 96% (n = 455) | 96% (n = 459) |
| Baseline Third-Treatment-Agent Class | | |
| INSTI | 94% (n = 105) | 95% (n = 97) |
| NNRTI | 96% (n = 275) | 95% (n = 278) |
| PI | 93% (n = 133) | 94% (n = 136) |
| Gender | | |
| Male | 95% (n = 393) | 96% (n = 403) |
| Female | 93% (n = 120) | 91% (n = 108) |
| Race | | |
| White | 94% (n = 421) | 95% (n = 400) |
| African-America/African Heritage/Other | 99% (n = 92) | 95% (n = 111) |
| Age (years) | | |
| <50 | 96% (n = 366) | 94% (n = 369) |
| ≥50 | 93% (n = 147) | 96% (n = 142) |

[a]Other includes reasons such as withdrew consent, loss to follow-up, moved, and protocol deviation.

Treatment differences were maintained across baseline characteristics including, CD4+ cell count, age, gender, race, and baseline third-treatment-agent class.

Example 7—Dolutegravir/Rilpivirine Bilayer Tablets

A bilayer formulation tablet of dolutegravir and rilpivirine was prepared using the tabletting procedure hereinbefore described. The composition of the formulation is summarised in the table below:

| | Tablet Formulation (mg/tablet) | |
|---|---|---|
| Component | Dolutegravir Layer | Rilpivirine Layer |
| Dolutegravir sodium | 52.62* | |
| Rilpivirine hydrochloride | | 27.5** |
| D-mannitol | 145.38 | 57.755 |
| Microcrystalline cellulose | 60.00 | |
| Povidone K29/32 | 15.00 | |
| Sodium starch glycolate | 21.00 | 12.90 |
| Sodium stearyl fumarate | 6.00 | |
| Lactose monohydrate | | 55.145 |
| Croscarmellose sodium | | 1.10 |

-continued

| Component | Tablet Formulation (mg/tablet) | |
|---|---|---|
| | Dolutegravir Layer | Rilpivirine Layer |
| Povidone K30 | | 3.25 |
| Polysorbate 20 | | 0.35 |
| Silicified mycrocrystalline cellulose | | 40.00 |
| Magnesium stearate | | 2.00 |
| Total Weight | 300.00 | 200.00 |

*Equivalent to 50 mg of dolutegravir
**Equivalent to 25 mg of rilpivirine.

In the bioequivalence studies of Example 8, the tablets of Example 7 were film coated by Opadry II Pink 85.

Example 8—Bioequivalence Studies

The bioequivalence of the fixed dose combination (FDC) tablets of Example 7 were evaluated versus co-administration of separate tablet formulations of Dolutegravir (DTG) 50 mg (Tivicay) and Rilpivirine (RPV) 25 mg (Edurant) in the fed state, as referenced in FIG. 17. The study was conducted as an open-label, randomized, 2-way crossover design at a single center, using healthy subjects.

One hundred and eighteen subjects were enrolled and randomized to receive a single dose of each of the two treatments. The details of the study treatments are provided below:

| Treatment | Dosing |
|---|---|
| A (Test) (FDC Tablet formulation of DTG/RPV 50 mg/25 mg) | One FDC Tablet of DTG 50 mg and RPV 25 mg was administered with 240 mL of water 30 minutes after moderate fat breakfast |
| B (Reference) (DTG 50 mg plus RPV 25 mg) | Separate tablets of DTG 50 mg and RPV 25 mg were administered together with 240 mL of water 30 minutes after moderate fat breakfast |

A total of one hundred and thirteen subjects completed both periods/treatments of the study.

A summary of the statistical analysis of Dolutegravir $C_{max}$ (maximum drug concentration), $AUC_{(0-t)}$ (area under the plasma concentration time curve from time 0 to the last measurable time point), $AUC_{(0-\infty)}$ (area under the plasma concentration time curve from time 0 extrapolated to infinity) and $C_{24}$ derived (drug concentration at 24 hours postdose) using actual sampling times is presented below (Table 22). For all 0.4 Dolutegravir PK parameters, derived using actual times, the ratios of the adjusted geometric means were close to 1 and the 90% CIs of the ratios were all contained within (0.80, 1.25) bioequivalence limits.

TABLE 22

Summary of the Statistical Analysis of Log-transformed DTG PK Parameters Based on Actual Sampling Times.

| PK Parameter | Test vs. Reference[1] | n | Test | n | Reference | Ratio | 90% CI of the Ratio | Adjusted Geometric Means | | |
|---|---|---|---|---|---|---|---|---|---|---|
| $C_{max}$ (μg/mL) | A vs B | 113 | 3.646 | 113 | 3.474 | 1.050 | (1.022, 1.078) | | | |
| $AUC_{(0-t)}$ (h * μg/mL) | A vs B | 113 | 63.583 | 113 | 61.265 | 1.038 | (1.011, 1.066) | | | |
| $AUC_{(0-\infty)}$ (h * μg/mL) | A vs B | 113 | 64.968 | 113 | 62.655 | 1.037 | (1.010, 1.064) | | | |
| $C_{24}$ (μg/mL)[1] | A vs B | 112 | 1.001 | 112 | 0.958 | 1.044 | (1.012, 1.077) | | | |
| | A vs B[1] | 113 | 1.003 | 112 | 0.960 | 1.045 | (1.012, 1.078) | | | |

[1]For $C_{24}$, subject 761082 was excluded due to no result for Period 2; in a separate supportive analysis this subject's Period 1 $C_{24}$ was included.
A = FDC Tablet formulation of DTG/RPV 50 mg/25 mg
B = DTG 50 mg plus RPV 25 mg
n = number of subjects per treatment with non-missing value.

A summary of the statistical analysis of Rilpivirine $C_{max}$, $AUC_{(0-t)}$, $AUC_{(0-\infty)}$ and $C_{24}$ derived using actual sampling times is presented below (Table 23). For all 4 Rilpivirine PK parameters, derived using actual times, the ratios of the adjusted geometric means were close to 1 and the 90% CIs of the ratios were all contained within the (0.80, 1.25) bioequivalence limits.

TABLE 23

Summary of the Statistical Analysis of Log-transformed RPV PK Parameters Based on Actual Sampling Times

| PK Parameter | Test vs. Reference[1] | Adjusted Geometric Means | | | | | 90% CI of the Ratio |
|---|---|---|---|---|---|---|---|
| | | n | Test | n | Reference | Ratio | |
| $C_{max}$ (μg/mL) | A vs B | 113 | 0.093 | 113 | 0.083 | 1.124 | (1.047, 1.207) |
| $AUC_{(0-t)}$ (h * μg/mL) | A vs B | 113 | 3.062 | 113 | 2.767 | 1.107 | (1.042, 1.176) |
| $AUC_{(0-\infty)}$ (h * μg/mL)[1] | A vs B | 112 | 3.248 | 112 | 2.933 | 1.108 | (1.045, 1.174) |
| | A vs B[1] | 113 | 3.254 | 112 | 2.936 | 1.108 | (1.046, 1.175) |
| $C_{24}$ (μg/mL) | A vs B | 113 | 0.031 | 113 | 0.028 | 1.101 | (1.034, 1.173) |

[1]For $AUC_{(0-\infty)}$, subject 761038 was excluded due to a result "not determined" in Period 1 because AUCextrap > 20%, $R^2$ < 0.85 in estimation of terminal phase rate constant, and range of time over which $t_{1/2}$ calculated was <2 × $t_{1/2}$; in a separate supportive analysis this subject's Period 1 $AUC_{(0-\infty)}$ was included.
A = FDC DTG/RPV 50 mg/25 mg
B = DTG 50 mg plus RPV 25 mg
n = number of subjects per treatment with non-missing value.

TABLE 24

Summary of Additional Pharmacokinetic Parameters Based on Actual Sampling Times

| | DTG (n = 113) | | RPV (n = 113) | |
|---|---|---|---|---|
| Pharmacokinetic parameter | Test (DTG/RPV FDC tablet) | Reference (DTG + RPV separate tablets) | Test (DTG/RPV FDC tablet) | Reference (DTG + RPV separate tablets) |
| $T_{max}$, median (range), h | 3.02 (0.50, 6.00) | 3.00 (0.50, 8.00) | 4.00 (1.00, 9.00) | 4.00 (1.50, 9.00) |
| $AUC_{0-24}$, adjusted geometric mean (95% CI), h · µg/mL | 43.9 (42.3, 45.6) | 42.4 (40.9, 44.1) | 0.946 (0.885, 1.01) | 0.860 (0.806, 0.919) |
| $C_t$, adjusted geometric mean (95% CI), µg/mL | 0.0576 (0.0522, 0.0636) | 0.0572 (0.0521, 0.0628) | 0.0020 (0.0018, 0.0022) | 0.0019 (0.0018, 0.0021) |
| $T_{last}$, median (range), h | 72.1 (48.0, 122) | 72.2 (48.0, 123) | 263.0 (119.0, 271.0) | 263.0 (73.1, 288.0) |
| $T_{lag}$, median (range), h | 0.00 (0.00, 1.03) | 0.00 (0.00, 1.00) | 0.50 (0.00, 2.50) | 0.50 (0.00, 2.57) |
| CL/F, adjusted geometric mean (95% CI), L/h | 0.77 (0.74, 0.81) | 0.80 (0.76, 0.84) | 7.68 (7.12, 8.29) | 8.53 (7.88, 9.22) |
| $t_{1/2}$, adjusted geometric mean (95% CI), h | 14.5 (14.0, 15.1) | 14.8 (14.2, 15.3) | 51.7 (48.1, 55.7) | 52.5 (48.8, 56.5) |

AUC, area under the concentration-time curve;
$AUC_{0-24}$, AUC from time 0 to 24 h;
CI, confidence interval;
CL/F, apparent oral clearance;
$C_{max}$, maximum concentration of drug in plasma;
$C_t$, last quantifiable concentration;
DTG, dolutegravir;
FDC, fixed-dose combination;
RPV, rilpivirine;
$t_{1/2}$, half-life;
$T_{lag}$, absorption lag time;
$T_{last}$, time of last quantifiable concentration;
$T_{max}$, time to $C_{max}$.

CL/F (apparent oral clearance) is the apparent total plasma clearance of drug after oral administration. $t_{1/2}$ (half-life) is the time the drug concentration in plasma needs to decrease by 50%. $T_{lag}$ (absorption lag time) is the time delay between drug administration and first observed concentration above LOQ (Limit Of Quantification) in plasma. $T_{last}$ (time of last quantifiable concentration) is the time of last observed concentration above LOQ (Limit Of Quantification) in plasma.

The median concentration-time curves associated with either DTG or RPV analytes were similar between the reference and test treatments (FIG. 16). The $AUC_{0-\infty}$, $AUC_{0-t}$, $C_{max}$, and plasma concentration at 24 hours post-dose ($C_{24}$) for both DTG and RPV analytes yielded adjusted geometric means ratios that were close to 1, with 90% CIs that were within the prespecified bioequivalence range of 0.80 to 1.25 (Tables 22 and 23). Additional pharmacokinetic parameters are summarized with descriptive statistics in Table 24 and were consistent with similar pharmacokinetic profiles between the DTG+RPV separate-tablet and the DTG/RPV FDC-tablet regimens.

The results of this study confirmed that the FDC formulation of Dolutegravir-Rilpivirine is bioequivalent to separate tablet formulations of Dolutegravir 50 mg and Rilpivirine 25 mg when administered after a moderate fat meal.

Fixed-dose combination tablets containing complete ART regimens have become widely available and are considered an important option to support treatment simplification and patient convenience. Therefore, the availability of a complete, NRTI-sparing DTG/RPV FDC tablet that is bioequivalent to DTG+RPV separate tablets under fed conditions will provide a valuable new option in the treatment of HIV-1 infection. This study served as a pharmacokinetic bridge from the DTG/RPV FDC tablet to the ongoing phase III SWORD trials in which participants took DTG+RPV as separate tablets with a meal.

Under certain circumstances, any information provided herein or derived herefrom that relates to regimen of the invention or composition of the invention may be included in a product label. Such circumstances may include, for example, requirements of a regulatory body, outcomes or data from clinical studies, or a decision of a manufacturer or other company.

Other embodiments may be utilized and logical and other changes may be made without departing from the scope of the invention. Therefore, the above detailed description is not to be taken in a limiting sense, and the scope of the invention is defined only by the appended claims, along with the full scope of equivalents to which such claims are entitled.

We claim:
1. A bilayer tablet comprising
   a) a first layer comprising dolutegravir sodium; and
   b) a second layer comprising rilpivirine hydrochloride;
   wherein said first layer and said second layer are in direct contact, and wherein the first layer consists of:

| Ingredient | Mass (mg) |
|---|---|
| Intragranular | |
| Dolutegravir sodium | 52.62 |
| D-mannitol | 145.38 |
| Microcrystalline cellulose | 60.00 |
| Povidone K29/32 | 15.00 |
| Sodium starch glycolate | 15.00 |
| Purified water | q.s. |
| Extragranular | |
| Sodium starch glycolate | 6.00 |
| Sodium stearyl fumarate | 6.00 | and the second layer consists of:

| Ingredient | Mass (mg) |
|---|---|
| Intragranular | |
| Rilpivirine hydrochloride | 27.50 |
| Lactose monohydrate | 55.145 |
| Croscarmellose sodium | 1.10 |
| Povidone K30 | 3.25 |
| Polysorbate 20 | 0.35 |
| Purified water | q.s. |
| Extragranular | |
| D-mannitol | 57.755 |
| Silicified microcrystalline cellulose | 40.00 |
| Sodium starch glycolate | 12.90 |
| Magnesium stearate | 2.00. |

2. The bilayer tablet of claim 1 wherein the bilayer tablet further comprises a coating.

3. The bilayer tablet of claim 2, wherein the coating comprises polyvinyl alcohol, titanium dioxide, macrogol/PEG, talc, yellow and red iron oxide.

4. The bilayer tablet of claim 2, wherein the bilayer tablet comprises about 1 mg to about 30 mg of the coating.

5. The bilayer tablet of claim 2, wherein the bilayer tablet comprises about 0.2% to about 6% w/w of the coating.

6. The bilayer tablet of claim 5, wherein the bilayer tablet comprises about 2% to about 4% w/w of the coating.

7. The bilayer tablet of claim 5, wherein the bilayer tablet comprises about 3% w/w of the coating.

8. The tablet of claim 2, the multilayer tablet comprises about 15 mg of the film coating.

* * * * *